(12) United States Patent
Kishi et al.

(10) Patent No.: US 12,227,795 B2
(45) Date of Patent: Feb. 18, 2025

(54) MOLECULAR PROGRAMMING TOOLS

(71) Applicant: President and Fellows of Harvard College, Cambridge, MA (US)

(72) Inventors: Jocelyn Yoshiko Kishi, Cambridge, MA (US); Thomas E. Schaus, Cambridge, MA (US); Peng Yin, Cambridge, MA (US); Feng Xuan, Cambridge, MA (US); Nikhil Gopalkrishnan, Cambridge, MA (US); Sungwook Woo, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 478 days.

(21) Appl. No.: 17/592,435

(22) Filed: Feb. 3, 2022

(65) Prior Publication Data
US 2022/0348990 A1 Nov. 3, 2022

Related U.S. Application Data

(62) Division of application No. 15/999,245, filed as application No. PCT/US2017/018086 on Feb. 16, 2017, now Pat. No. 11,286,517.

(60) Provisional application No. 62/432,017, filed on Dec. 9, 2016, provisional application No. 62/429,149, filed on Dec. 2, 2016, provisional application No. 62/299,206, filed on Feb. 24, 2016, provisional application No. 62/296,310, filed on Feb. 17, 2016.

(51) Int. Cl.
| | |
|---|---|
| *C12Q 1/68* | (2018.01) |
| *C12N 15/113* | (2010.01) |
| *C12N 15/64* | (2006.01) |
| *C12P 19/34* | (2006.01) |
| *C12Q 1/6806* | (2018.01) |
| *C12Q 1/6809* | (2018.01) |
| *C12Q 1/6811* | (2018.01) |
| *C12Q 1/6825* | (2018.01) |
| *C12Q 1/6853* | (2018.01) |

(52) U.S. Cl.
CPC .......... *C12Q 1/6811* (2013.01); *C12N 15/113* (2013.01); *C12N 15/64* (2013.01); *C12P 19/34* (2013.01); *C12Q 1/6806* (2013.01); *C12Q 1/6809* (2013.01); *C12Q 1/6825* (2013.01); *C12Q 1/6853* (2013.01); *C12N 2310/122* (2013.01); *C12N 2310/127* (2013.01); *C12N 2330/50* (2013.01)

(58) Field of Classification Search
None
See application file for complete search history.

(56) References Cited

U.S. PATENT DOCUMENTS

| | | |
|---|---|---|
| 5,030,566 A | 7/1991 | Son et al. |
| 5,543,507 A | 8/1996 | Cook et al. |
| 5,866,336 A | 2/1999 | Nazarenko et al. |
| 8,962,241 B2 | 2/2015 | Yin et al. |
| 9,284,602 B2 | 3/2016 | Zhang et al. |
| 10,024,796 B2 | 7/2018 | Lin et al. |
| 10,036,059 B2 | 7/2018 | Zhang et al. |
| 10,876,971 B2 | 12/2020 | Lin et al. |
| 11,286,517 B2 * | 3/2022 | Kishi .................. C12N 15/113 |
| 2002/0064772 A1 | 5/2002 | Gildea et al. |
| 2004/0166520 A1 | 8/2004 | Connolly |
| 2005/0045063 A1 | 3/2005 | Niggemann et al. |
| 2005/0112610 A1 | 5/2005 | Lee et al. |
| 2006/0063196 A1 | 3/2006 | Akeson et al. |
| 2006/0188902 A1 | 8/2006 | Narayanan et al. |
| 2006/0199216 A1 | 9/2006 | Su et al. |
| 2006/0286569 A1 | 12/2006 | Bar-Or et al. |
| 2007/0048759 A1 | 3/2007 | Luo et al. |
| 2007/0048761 A1 | 3/2007 | Reep et al. |
| 2007/0117109 A1 | 5/2007 | Rothemund |
| 2008/0287668 A1 | 11/2008 | Toth-Fejel et al. |
| 2008/0299559 A1 | 12/2008 | Kwok et al. |
| 2009/0011956 A1 | 1/2009 | Yin et al. |
| 2009/0042191 A1 | 2/2009 | Hayward et al. |
| 2010/0015607 A1 | 1/2010 | Geiss et al. |
| 2010/0069621 A1 | 3/2010 | Maune et al. |
| 2010/0105052 A1 * | 4/2010 | Drmanac ............. C12Q 1/6874 435/6.12 |
| 2010/0216978 A1 | 8/2010 | Shih |
| 2011/0129834 A1 | 6/2011 | Chen et al. |
| 2011/0300640 A1 | 12/2011 | Josten et al. |
| 2012/0021410 A1 | 1/2012 | Yin et al. |
| 2012/0022243 A1 | 1/2012 | Yin |

(Continued)

FOREIGN PATENT DOCUMENTS

| | | |
|---|---|---|
| CN | 1432061 A | 7/2003 |
| CN | 1836050 A | 9/2006 |

(Continued)

OTHER PUBLICATIONS

Byrom et al., 2014. Exquisite allele discrimination by toehold hairpin primers. Nucleic acids research, 42(15), e120, pp. 1-12. (Year: 2014).*

(Continued)

*Primary Examiner* — Stephanie K Mummert
*Assistant Examiner* — Olayinka A Oyeyemi
(74) *Attorney, Agent, or Firm* — Wolf, Greenfield & Sacks, P.C.

(57) ABSTRACT

The present disclosure provides, in some aspects, nucleic acid-based molecular tools that enable the recording of molecular structure and soluble signals as well as the programmed assembly of molecular structures.

16 Claims, 38 Drawing Sheets

Specification includes a Sequence Listing.

(56) References Cited

U.S. PATENT DOCUMENTS

| | | | |
|---|---|---|---|
| 2012/0022244 | A1 | 1/2012 | Yin |
| 2012/0178081 | A1 | 7/2012 | Nguyen et al. |
| 2013/0072390 | A1 | 3/2013 | Wang et al. |
| 2013/0244894 | A1 | 9/2013 | Mercolino |
| 2013/0261019 | A1 | 10/2013 | Lin et al. |
| 2014/0081665 | A1 | 3/2014 | Holmes et al. |
| 2014/0087377 | A1 | 3/2014 | Park et al. |
| 2014/0141984 | A1 | 5/2014 | Swartz et al. |
| 2014/0255921 | A1 | 9/2014 | Moysey et al. |
| 2014/0349288 | A1 | 11/2014 | Church et al. |
| 2015/0111780 | A1 | 4/2015 | Mercolino |
| 2016/0024558 | A1 | 1/2016 | Hardenbol et al. |
| 2016/0312272 | A1* | 10/2016 | Barish ................ C12Q 1/6834 |
| 2017/0327888 | A1 | 11/2017 | Ong et al. |
| 2018/0010174 | A1* | 1/2018 | Schaus ................ C12Q 1/6804 |
| 2019/0003973 | A1 | 1/2019 | Lin et al. |
| 2019/0106733 | A1* | 4/2019 | Kishi ................ C12Q 1/6806 |
| 2020/0362398 | A1 | 11/2020 | Kishi et al. |
| 2021/0019973 | A1 | 1/2021 | Yin et al. |
| 2022/0348990 | A1* | 11/2022 | Kishi ................ C12Q 1/6825 |

FOREIGN PATENT DOCUMENTS

| | | |
|---|---|---|
| CN | 101048505 A | 10/2007 |
| CN | 101541975 A | 9/2009 |
| CN | 102317471 A | 1/2012 |
| CN | 102782158 A | 11/2012 |
| CN | 103014168 A | 4/2013 |
| CN | 104164488 A | 11/2014 |
| JP | 2008-017853 A | 1/2008 |
| JP | 2013-540451 A | 11/2013 |
| JP | 2014-504153 A | 2/2014 |
| JP | 2015-523864 A | 8/2015 |
| WO | WO 2004/046321 A2 | 6/2004 |
| WO | WO 2007/002016 A2 | 1/2007 |
| WO | WO 2007/117256 A1 | 10/2007 |
| WO | WO 2010/146349 A1 | 12/2010 |
| WO | WO 2011/156434 A2 | 12/2011 |
| WO | WO 2012/058638 A2 | 3/2012 |
| WO | WO 2012/057689 A1 | 5/2012 |
| WO | WO 2012/071428 A2 | 5/2012 |
| WO | WO-2012058488 A1 * | 5/2012 ............ C07H 21/02 |
| WO | WO 2012/078312 A2 | 6/2012 |
| WO | WO 2013/012434 A1 | 1/2013 |
| WO | WO 2013/140107 A1 | 9/2013 |
| WO | WO 2013/188912 A1 | 12/2013 |
| WO | WO 2014/074648 A2 | 5/2014 |
| WO | WO 2014/164958 A1 | 10/2014 |
| WO | WO 2015/095633 A1 | 6/2015 |
| WO | WO 2015/114469 A2 | 8/2015 |
| WO | WO-2015178978 A2 * | 11/2015 ........... C12Q 1/6844 |
| WO | WO 2016/011089 A1 | 1/2016 |
| WO | WO-2016123419 A1 * | 8/2016 ........... C12Q 1/6804 |
| WO | WO 2018/057502 A2 | 3/2018 |
| WO | WO 2018/132392 A2 | 7/2018 |
| WO | WO 2019/147945 A1 | 8/2019 |
| WO | WO 2019/183359 A1 | 9/2019 |

OTHER PUBLICATIONS

Fujimo, K., Konishi-Hiratsuka, K. and Sakamoto, T., 2013. Quick, Selective and reversible photocrosslinking Reaction between 5-methylcytosine and 3-cyanovinylcarbazole in DNA double strand. International journal of molecular sciences, 14(3), pp. 5765-5774. (Year: 2013).*

Kishi JY, Schaus TE, Gopalkrishnan N, Xuan F, Yin P. Programmable autonomous synthesis of single-stranded DNA. Nat Chem. Feb. 2018; 10(2):155-164. Epub Nov. 6, 2017. (Year: 2018).*

Zhu, J., Ding, Y., Liu, X., Wang, L. and Jiang, W., 2014. Toehold-mediated strand displacement reaction triggered isothermal DNA amplification for highly sensitive and selective fluorescent detection of single-base mutation. Biosensors and Bioelectronics, 59, pp. 276-281. (Year: 2014).*

U.S. Appl. No. 13/882,231, filed Jul. 1, 2013, Granted, U.S. Pat. No. 9,284,602.
U.S. Appl. No. 14/553,165, filed Nov. 25, 2014, Granted, U.S. Pat. No. 10,036,059.
U.S. Appl. No. 17/169,145, filed Feb. 5, 2021, Published, 2021-0388430.
U.S. Appl. No. 13/882,223, filed Jun. 11, 2013, Granted, U.S. Pat. No. 10,024,796.
U.S. Appl. No. 16/008,719, filed Jun. 14, 2018, Granted, U.S. Pat. No. 10,876,971.
U.S. Appl. No. 15/542,953, filed Dec. 4, 2017, Published, 2018-0010174.
U.S. Appl. No. 15/999,245, filed Aug. 17, 2018, Granted, U.S. Pat. No. 11,286,517.
U.S. Appl. No. 16/334,643, filed Mar. 19, 2019, Allowed, 2021-0277452.
U.S. Appl. No. 16/464,170, filed May 24, 2019, Published, 2020-0362398.
U.S. Appl. No. 16/964,527, filed Jul. 23, 2020, Published, 2021-0147902.
U.S. Appl. No. 17/040,041, filed Sep. 21, 2020, Published, 2021-0019973.
EP 17753794.1, Sep. 25, 2019, Extended European Search Report.
EP 21171977.8, Sep. 30, 2021, Extended European Search Report.
PCT/US2017/018086, Apr. 17, 2017, Invitation to Pay Additional Fees.
PCT/US2017/018086, Jun. 15, 2017, International Search Report and Written Opinion.
PCT/US2017/018086, Aug. 30, 2018, International Preliminary Report on Patentability.
Extended European Search Report mailed Sep. 25, 2019 for Application No. 17753794.1.
Extended European Search Report for Application No. EP 21171977.8, mailed Sep. 30, 2021.
International Preliminary Report on Patentability mailed Aug. 30, 2018 for PCT/US2017/018086.
Invitation to Pay Additional Fees for PCT/US2017/018086 mailed Apr. 17, 2017.
International Search Report and Written Opinion for PCT/US2017/018086 mailed Jun. 15, 2017.
[No Author Listed], New COVID-19 Variants. Centers for Disease Control and Prevention. Updated Jan. 15, 2021. 3 pages.
Baccouche et al., Dynamic DNA-toolbox reaction circuits: a walkthrough. Methods. May 15, 2014;67(2):234-49. doi: 10.1016/j.ymeth.2014.01.015. Epub Feb. 2, 2014.
Beliveau et al., Single-molecule super-resolution imaging of chromosomes and in situ haplotype visualization using Oligopaint FISH probes. Nat Commun. May 2015;6:7147(1-13).
Beliveau et al., Versatile design and synthesis platform for visualizing genomes with Oligopaint FISH probes. Proc Natl Acad Sci U S A. Dec. 26, 2012;109(52):21301-6. doi:10.1073/pnas.1213818110. Epub Dec. 11, 2012.
Chen et al., Conditionally fluorescent molecular probes for detecting single base changes in double-stranded DNA. Nat Chem. Sep. 2013;5(9):782-9. Author Manuscript, 16 pages.
Collins et al., A branched DNA signal amplification assay for quantification of nucleic acid targets below 100 molecules/ml. Nucl Acids Res. Aug. 1997;25(15):2979-2984.
Douglas et al., Self-assembly of DNA into nanoscale three-dimensional shapes. Nature. May 21, 2009;459(7245):414-8. doi: 10.1038/nature08016.
Dreyfus et al., A Supply chain management perspective on mitigating the risks of counterfeit products. Michigan State University. Oct. 2013. https://globaledge.msu.edu/Content/Uploads/Supply-Chain-Bgrounder_V8_FINAL_.pdf.
Fiandaca et al., Self-reporting PNA/DNA primers for PCR analysis. Genome Res. Apr. 2001;11(4):609-13. doi: 10.1101/gr.170401.
Forster et al., A human gut bacterial genome and culture collection for improved metagenomic analyses. Nat Biotechnol. 2019;37(2):186-192. doi:10.1038/s41587-018-0009-7.

(56) References Cited

OTHER PUBLICATIONS

Fujimo et al., Quick, Selective and Reversible Photocrosslinking Reaction between 5-Methylcytosine and 3-Cyanovinylcarbazole in DNA Double Strand. Int J Mol Sci. Mar. 12, 2013;14(3):5765-74. doi: 10.3390/ijms14035765.

Hollenstein. DNA Synthesis by primer exchange reaction cascades. Chembiochem. Mar. 2, 2018;19(5):422-4. Epub Jan. 24, 2018.

Jiang et al., Real-time detection of isothermal amplification reactions with thermostable catalytic hairpin assembly. J Am Chem Soc. May 22, 2013;135(20):7430-3 and Supporting Information. doi: 10.1021/ja4023978. Epub May 9, 2013.

Jungmann et al., Multiplexed 3D cellular super-resolution imaging with DNA-PAINT and Exchange-PAINT. Nat Methods. Mar. 2014;11(3):313-8. doi: 10.1038/nmeth.2835. Epub Feb. 2, 2014.

Jungmann et al., Nanoscale imaging in DNA nanotechnology. Wiley Interdiscip Rev Nanomed Nanobiotechnol. Jan.- Feb. 2012;4(1):66-81. doi:10.1002/wnan.173. Epub Nov. 23, 2011.

Jungmann et al., Single-molecule kinetics and super-resolution microscopy by fluorescence imaging of transient binding on DNA origami. Nano Lett. Nov. 10, 2010;10(11):4756-61.

Kishi et al., Programmable autonomous synthesis of single-stranded DNA. Nat Chem. Feb. 2018;10(2):155-64. Epub Nov. 6, 2017. Author Manuscript, 22 pages.

Li et al., Multiplexed detection of pathogen DNA with DNA-based fluorescence nanobarcodes. Nat Biotechnol. Jul. 2005;23(7):885-9. Epub Jun. 12, 2005.

Montagne et al., Programming an in vitro DNA oscillator using a molecular networking strategy. Mol Syst Biol. Feb. 1, 2011;7:466. doi: 10.1038/msb.2010.120. Erratum in: Mol Syst Biol. Mar. 8, 2011;7:476. Mol Syst Biol. 2011;7. doi:10.1038/msb.2011.12.

Nazarenko et al., Multiplex quantitative PCR using self-quenched primers labeled with a single fluorophore. Nucleic Acids Res. May 1, 2002;30(9):e37(1-7). doi: 10.1093/nar/30.9.e37.

Pardee et al., Paper-based synthetic gene networks. Cell. Nov. 6, 2014;159(4):940-54. doi: 10.1016/j.cell.2014.10.004. Epub Oct. 23, 2014.

Player et al., Single-copy gene detection using branched DNA (bDNA) in situ hybridization. J Histochem & Cytochem. May 2001;49(5):603-11.

Rothemund, Folding DNA to create nanoscale shapes and patterns. Nature. Mar. 16, 2006;440(7082):297-302.

Sah et al., Complete Genome Sequence of a 2019 Novel Coronavirus (SARS-COV-2) Strain Isolated in Nepal. Microbiol Resour Announc. Mar. 12, 2020;9(11):e00169-20. doi: 10.1128/MRA.00169-20.

Simonsson et al., A substrate for telomerase. Trends Biochem Sci. Dec. 2003;28(12):632-8. doi: 10.1016/j.tibs.2003.10.005.

Tisza et al., Discovery of several thousand highly diverse circular DNA viruses. Elife. Feb. 4, 2020;9:e51971. doi: 10.7554/eLife.51971.

Tribioli et al., Long-term room temperature storage of high-quality embryonic stem cell genomic DNA extracted with a simple and rapid procedure. J Biomol Tech. Sep. 2006;17(4):249-51.

Wang et al, RNAscope: A novel in situ RNA analysis platform for formalin-fixed, paraffin-embedded tissues. J Mol Diagn. Jan. 2012;14(1):22-9.

Wang et al., Proximity hybridization-regulated immunoassay for cell surface protein and protein-overexpressing cancer cells via electrochemiluminescence. Anal Chem. Mar. 6, 2018;90(5):3013-8. Epub Feb. 23, 2018.

Weibrecht et al., In situ detetion of individual mRNA molecules and protein complexes or post-translational modifications using padlock probes combined with the in situ proximity ligation assay. Nat Protoc. Feb. 2013;8(2):355-72.

Weibrecht et al., Proximity ligation assays: a recetn addition to the proteomics toolbox. Expert Rev of Proteomics. Jun. 2010;7(3):401-9.

Wharam et al., Specific detection of DNA and RNA targets using a novel isothermal nucleic acid amplification assay based on the formation of a three-way junction structure. Nucleic Acids Res. Jun. 1, 2001;29(11):E54-4.

Woehrstein et al., Sub-100 nm metafluorophores with digitally tunable optical properties self-assembled from DNA. Sci Adv. Jun. 21, 2017;3(6):e1602128.

Wu et al., A nonenzymatic hairpin DNA Cascade reaction provides high signal gain of mRNA imagin inside live cells. J Am Chem Soc. Apr. 2015;137(15):4900-3.

Yan et al., Isothermal amplified detection of DNA and RNA. Mol Biosyst. May 2014;10(5):970-1003.

Yin et al., Programming biomolecular self-assembly pathways. Nature. Jan. 17, 2008;451(7176):318-22. doi:10.1038/nature06451.

Zeberg et al., The major genetic risk factor for severe COVID-19 is inherited from Neanderthals. Nature. Nov. 2020;587(7835):610-612. doi: 10.1038/s41586-020-2818-3. Epub Sep. 30, 2020.

Zhang et al., Control of DNA strand displacement kinetics using toehold exchange. J Am Chem Soc. Dec. 2, 2009;131(47):17303-14. doi: 10.1021/ja906987s.

Zhang et al., Dynamic DNA nanotechnology using strand-displacement reactions. Nat Chem. 2011;3(2):103-13.

Zhang et al., Optimizing the specificity of nucleic acid hybridization. Nat Chem. Epub Jan. 22, 2012, 7 pages.

Zhu et al., Toehold-mediated strand displacement reaction triggered isothermal DNA amplification for highly sensitive and selective fluorescent detection of single-base mutation. Biosens Bioelectron. Sep. 15, 2014;59:276-81. doi: 10.1016/j.bios.2014.03.051. Epub Apr. 1, 2014.

\* cited by examiner

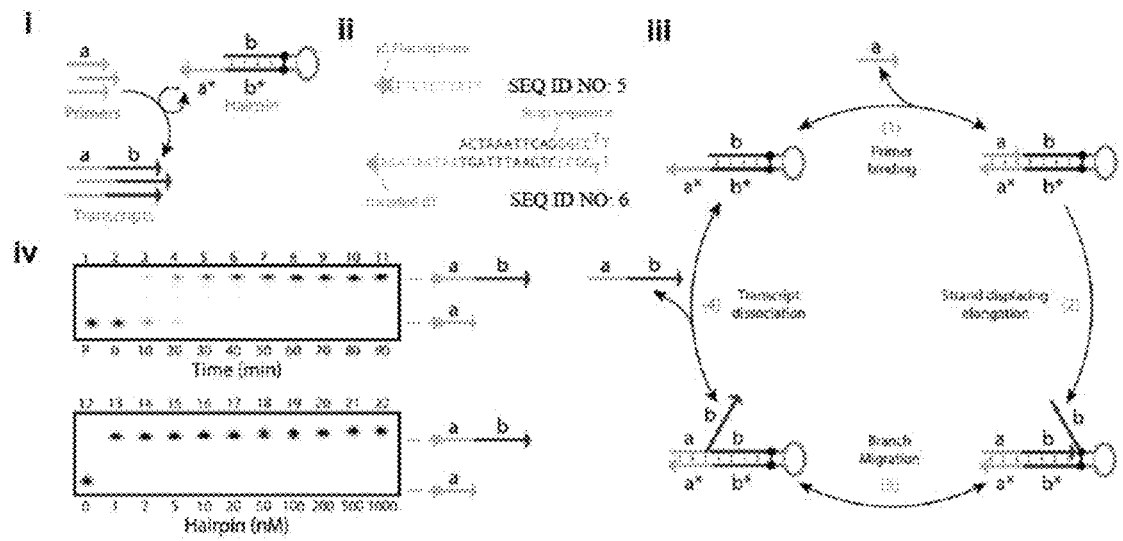

Fig. 44F

```
t*      b*                x*                                    x                                      b              t                a                                          b
ACATACT CATCTCG /iisodG/ CGCTCG /iisodC/ TT/iBiodT/TT CCAGCmG /iMe-isodC/ CGAGATG AGTATGT AGTTAGAGATGT/iMe-isodC/A CGAGATG /3InvdT/
ACATACT CATCTCG /iisodG/ CGCTCG /iisodC/ TT/iBiodT/TT CCAGCmG /iMe-isodC/ GGAGATG AGTATGT AGTTAGAGATGTGA CGAGATG /3InvdT/
ACATACT CATCTCG /iisodG/ CGCTCG /iisodC/ TT/iBiodT/TT CCAGCmG /iMe-isodC/ CGAGATG AGTATGT AGTTAGAGATGmTmGmA CGAGATG /3InvdT/
```

MOLECULAR PROGRAMMING TOOLS

RELATED APPLICATIONS

This application is a divisional of U.S. application Ser. No. 15/999,245, filed Aug. 17, 2018, which is a national stage filing under 35 U.S.C § 371 of international application number PCT/US2017/018086, filed Feb. 16, 2017, which claims the benefit under 35 U.S.C. § 119 (e) of U.S. provisional application No. 62/296,310, filed Feb. 17, 2016, U.S. provisional application No. 62/299,206, filed Feb. 24, 2016, U.S. provisional application No. 62/429,149, filed Dec. 2, 2016, and U.S. provisional application No. 62/432,017, filed Dec. 9, 2016, each of which is incorporated by reference herein in its entirety.

GOVERNMENT LICENSE RIGHTS

This invention was made with government support under EB018659 and GM133052 awarded by National Institutes of Health (NIH); under 1317291, 1334109, and 1540214 awarded by National Science Foundation (NSF); and under N00014-14-1-0610, N00014-13-1-0593, and N00014-16-1-2410 awarded by U.S. Office of Naval Research (NAVY/ONR). The government has certain rights in the invention.

BACKGROUND

The information encoding properties of deoxyribonucleic acid (DNA) and relative ease of programming Watson-Crick base pairing complementarity have led to DNA being used as a substrate in many different applications in the last 20 years.[1-9] Moreover, DNA has been programmed to self-assemble into nanostructures of prescribed 2D and 3D shapes,[10-18] allowing for the precise spatial patterning of biomolecules[19-26] and even the shaping of inorganic molecules.[27] These synthetic systems have already shown their worth in the fields of synthetic biology, materials science, and biological imaging, with researchers working on applications of DNA nanostructures for nuclear magnetic resonance (NMR) structure determination of biomolecules,[28] conditional regulation of cellular pathways,[22,29,30] and DNA nanostructures as vehicles for drug delivery.[31,32]

SUMMARY

Provided herein, in some aspects, are nucleic acid-based molecular tools that enable the recordation and reconstruction of molecular landscapes. DNA patterns life by encoding the information for diverse molecular functions in the genome. It also serves as the template substrate for a multitude of synthetic reaction networks, such as the polymerase chain reaction (PCR) (Randall K Saiki, et al. Science, 239(4839):487-491, 1988), rolling circle amplification (RCA) (Paul M Lizardi, et al. Nature genetics, 19(3):225-232, 1998), and strand displacement circuitry (Lulu Qian and Erik Winfree. Science, 332(6034):1196-1201, 201; David Yu Zhang and Georg Seelig. Nature chemistry, 3(2): 103-113, 2011). The present disclosure introduces, inter alia, the concept of primer exchange reactions (PER), which use catalytic DNA hairpin species, in some embodiments, to pattern the isothermal synthesis of single-stranded DNA (ssDNA) in a stepwise fashion. Data provided herein show that primer exchange reaction cascades can be used to grow a nascent strand of DNA following a prescribed pathway and can also be used to construct a synthetic telomerase that linearly amplifies a specific primer signal, for example. Additional data provided herein demonstrate the implementation of several functional systems that process and respond to RNA signals in solution, including a label-free biosensor, a temporal recorder, logic circuits, and a nanodevice that transduces the detection of a target signal into a functional DNAzyme that operates on an independent RNA sequence. The methods of the present disclosure may be used to synthesize arbitrary ssDNA in an isothermal in situ environment, for example, and provide the basis for a new generation of molecular devices.

Thus, some aspects provide a molecular primitive for dynamic DNA circuitry, referred to herein as "primer exchange," which provides basis, inter alia, for in situ synthesizing highly robust dynamic constructs. During a primer exchange reaction (PER), a discrete nucleotide sequence (domain) is added (synthesized) to a "growing" nucleic acid strand, using a strand displacement polymerase and a partially-paired molecule (e.g., hairpin molecule) that acts catalytically (see, e.g., FIGS. 1A-1B). A PER represents a new paradigm for molecular programming, with its catalytic activity, modularity, robustness, basic fuel species (dNTPs), in situ operation, and single-molecule transcript recording. This method of isothermal and autonomous synthesis of single-stranded DNA with arbitrary user-prescribed sequence may be adapted for both in situ and in vivo use.

Other aspects of the present disclosure provide molecular (e.g., DNA) motor systems that convert chemical energy (e.g., enthalpy associated with DNA hybridization or entropy associated with release of DNA molecules from a complex) into mechanical work using nucleic acid molecules that function as individual sites of a track that provide physical support and, in some instances, prescribe the direction or path of molecular movement for a growing nucleic acid record of information (see, e.g., FIGS. 23A-24B). The molecular motor systems, as provided herein, enable programmable generation of molecular components in situ, in some embodiments, only when and where needed. That is, molecules can be actively manufactured as a reaction is carried out. This technology enables inspection of molecular environments and conditions at the molecular level. This technology also provides quantification and reconstruction of the molecular landscapes from inspection records generated from interactions with individual track site molecules. The growing strands of nucleic acid, which function as molecular motors moving from one track site molecule to another in a particular environment/landscape are referred to as "molecular crawlers" (see, e.g., FIGS. 28A-28B) and "molecular walkers" (see, e.g., FIGS. 29A-29B).

Yet other aspects of the present disclosure provide an autonomous, bottom-up tool that records nanoscale (or microscale) distances between target molecules by recording distance information within paired nucleic acid molecules, referred to as records. The length of the nucleic acid record produced during a reaction directly corresponds to the distance being measured (e.g., distance between biomolecules). In addition, each nucleic acid record can encode the identity of the target molecules as part of its sequence. This molecular ruler system (see, e.g., FIGS. 33A-34) can record distances in a solution of target molecules, in solid-phase or in situ.

Thus, some aspects of the present disclosure provide a primer exchange reaction (PER) system, comprising: (a) an initial catalytic molecule comprising (i) an unpaired 3' toehold domain and (ii) a paired domain located 5' from the toehold domain; (b) an initial primer that is complementary to the unpaired 3' toehold domain; and (c) polymerase having strand displacement activity. In some embodiments, the initial catalytic molecule has a hairpin structure and, thus, further comprises a loop domain located at the end opposite the 3' toehold domain, which is 5' from the paired domain (see, e.g., FIG. 1A). In some embodiments, the systems further comprise deoxyribonucleotide triphosphates (dNTPs).

A "domain" refers to a discrete, contiguous sequence of nucleotides or nucleotide base pairs, depending on whether the domain is unpaired (single-stranded nucleotides) or paired (double-stranded nucleotide base pairs), respectively. In some embodiments, a domain is described as having multiple subdomains for the purpose of defining intramolecular (within the same molecular species) and intermolecular (between two separate molecular species) complementarity. One domain (or one subdomain) is "complementary to" another domain if one domain contains nucleotides that base pair (hybridize/bind through Watson-Crick nucleotide base pairing) with nucleotides of the other domain such that the two domains form a paired (double-stranded) or partially-paired molecular species/structure. Complementary domains need not be perfectly (100%) complementary to form a paired structure, although perfect complementarity is provided, in some embodiments. Thus, a primer that is "complementary" to a particular domain binds to that domain, for example, for a time sufficient to initiate polymerization in the presence of polymerase. FIG. 1A, for example, shows primer '1' binding to domain '1'' of a catalytic hairpin molecule. Similarly, FIG. 1B shows primer domain '2' of a primer binding to domain '2'' of a catalytic hairpin molecule.

Catalytic molecules that do not have a hairpin loop (are not formed by a contiguous stretch of nucleotides) are described, in some embodiments, as being a duplex that includes "displacement strand" paired with (hybridized/bound to) a "template strand." FIG. 24 (third "Duplex" panel) shows an example of a duplex catalytic molecule formed by binding of displacement strand '1' (top, shorter strand) to template strand '1'+1'' (bottom, longer strand).

It should be understood that any one of the catalytic molecules provided herein may comprise a "linkage domain" located at the end of the molecule opposite to the toehold domain. The linkage domain may be a hairpin loop (loop domain), as shown for example in FIGS. 1A-1C, or the linkage domain may include complementary nucleotides covalently crosslinked to each other (e.g., at least 1, 2, 3, 4, 5, 6, 7, 8, 9, or 10 covalently crosslinked nucleotide base pairs). In some embodiments, a linkage domain is simply a stable paired domain, for example, having a length of at least 10 nucleotides (e.g., such that the domain remains paired throughout PER conditions).

Some aspects of the present disclosure provide primer exchange reaction (PER) systems, comprising: (a) an initial catalytic hairpin molecule comprising (i) an unpaired 3' toehold domain, (ii) a paired stem domain formed by intramolecular nucleotide base pairing between a 3' subdomain of the molecule and a 5' subdomain of the molecule, and (iii) a loop domain; (b) an initial primer complementary to the unpaired 3' toehold domain; and (c) polymerase having strand displacement activity. Hairpin molecules are generally formed by intramolecular nucleotide base pairing, which refers to binding between domains of the same contiguous strand of nucleic acid. For example, FIG. 1A shows a hairpin molecule formed by binding of 5' (upstream) domain '2' to a 3' (downstream) domain '2''. It should be understood that the 5' domain '2' functions in a manner similar to a displacement strand of a duplex catalytic molecule, and the 3' domain '2'' together with toehold domain '1'' function in a manner similar to the template strand of a duplex catalytic molecule.

Other aspects of the present disclosure provide primer exchange reaction (PER) systems, comprising: (a) an initial catalytic molecule comprising (i) an unpaired 3' toehold domain and (ii) a paired domain located 5' from the toehold domain formed by nucleotide base pairing between a displacement strand and a template strand containing the toehold domain; (b) a second catalytic molecule comprising (i) an unpaired 3' toehold domain and (ii) a paired domain located 5' from the toehold domain formed by nucleotide base pairing between a displacement strand and a template strand containing the toehold domain of the second catalytic molecule, wherein the 3' toehold domain of the second catalytic molecule is complementary to the displacement strand of the initial catalytic molecule; and (c) an initial primer complementary to the unpaired Y toehold domain of the initial catalytic molecule. In some embodiments, the PER systems further comprise a polymerase having strand displacement activity. In some embodiments, the PER systems further comprise dNTPs.

In some embodiments, the PER systems comprise: (a) an initial catalytic hairpin molecule comprising (i) an unpaired 3' toehold domain, (ii) a paired stem domain formed by intramolecular nucleotide base pairing between a 5' subdomain of the molecule and a 3' subdomain of the molecule, and (iii) a loop domain; (b) a second catalytic hairpin molecule comprising (i) an unpaired 3' toehold domain, (ii) a paired stem domain formed by intramolecular nucleotide base pairing between a 3' subdomain of the second hairpin molecule and a 5' subdomain of the second hairpin molecule, and (iii) a loop domain, wherein the 3' toehold domain of the second hairpin molecule is complementary to the 5' subdomain of the initial hairpin molecule; and (c) an initial primer complementary to the unpaired 3' toehold domain of the initial hairpin molecule.

Yet other aspects of the present disclosure provide primer exchange reaction (PER) methods, comprising: combining in reaction buffer (a) an initial catalytic molecule comprising (i) an unpaired 3 toehold domain and (ii) a paired domain located 5' from the toehold domain formed by nucleotide base pairing between a displacement strand and a template strand containing the toehold domain, (b) a second catalytic molecule comprising (i) an unpaired 3' toehold domain and (ii) a paired domain located 5' from the toehold domain formed by nucleotide base pairing between a displacement strand and a template strand containing the toehold domain of the second catalytic molecule, wherein the 3' toehold domain of the second catalytic molecule is complementary to the displacement strand of the initial catalytic molecule, (c) a primer complementary to the unpaired 3 toehold domain of the initial catalytic molecule, (d) a polymerase having strand displacement activity, and (e) deoxyribonucleotide triphosphates (dNTPs), thereby forming a reaction mixture; and incubating the reaction mixture under conditions that result in nucleic acid polymerization, strand displacement and annealing, for a time sufficient to produce a single-stranded nucleic acid record.

In some embodiments, PER methods comprise: combining in reaction buffer (a) an initial catalytic hairpin molecule comprising (i) an unpaired 3' toehold domain, (ii) a paired stem domain formed by intramolecular nucleotide base pairing between a 3' subdomain of the molecule and a 5' subdomain of the molecule, and (iii) a hairpin loop domain, (b) a second catalytic hairpin molecule comprising (i) an unpaired 3' toehold domain, (ii) a paired stem domain formed by intramolecular nucleotide base pairing between a 3' subdomain of the second hairpin molecule and a 5' subdomain of the second hairpin molecule, and (iii) a loop domain, wherein the 3' toehold domain of the second hairpin molecule is complementary to the 5' subdomain of the initial hairpin molecule, (c) a primer complementary to the unpaired 3' toehold domain of the initial hairpin molecule, (d) a polymerase having strand displacement activity, and (e) deoxyribonucleotide triphosphates (dNTPs), thereby forming a reaction mixture; and incubating the reaction mixture under conditions that result in nucleic acid polymerization, strand displacement and annealing, for a time sufficient to produce a single-stranded nucleic acid record.

In some embodiments, a PER method comprises (a) contacting an input primer with a catalytic molecule, in the presence of polymerase having strand displacement activity and deoxyribonucleotide triphosphates (dNTPs), wherein the catalytic molecule comprises (i) an unpaired 3' toehold domain and (ii) a paired domain located 5' from the toehold domain that is formed by nucleotide base pairing between a displacement strand and a template strand containing the toehold domain, wherein the input primer is complementary to the 3' toehold domain of the hairpin molecule; (b) extending the primer through the paired domain of the catalytic molecule, thereby displacing the displacement strand and forming an extended output primer; (c) displacing the extended output primer from the hairpin molecule through nucleotide base pairing between the displacement strand and the template strand; and (d) contacting the displaced extended output primer of (c) with a second catalytic molecule, in the presence of polymerase having strand displacement activity and dNTPs, wherein the second catalytic molecule comprises (i) an unpaired 3' toehold domain and (ii) a paired domain located 5' from the toehold domain that is formed by nucleotide base pairing between a displacement strand and a template strand containing the toehold domain of the second catalytic molecule, and wherein the extended output primer is complementary to the 3' toehold domain of the second catalytic molecule. In some embodiments, the catalytic molecules are catalytic hairpin molecules.

Also provided herein are compositions, comprising (a) a catalytic hairpin molecule comprising (i) an unpaired 3' toehold domain, (ii) a paired stem domain formed by intramolecular nucleotide base pairing between a 3' subdomain of the molecule and a 5' subdomain of the molecule, and (iii) a linkage domain, wherein the domains of (a)(i) and (a)(ii) form tandem repeat sequences, (b) at least one other catalytic hairpin molecule comprising (i) a 3' toehold domain, (ii) a paired stem domain formed by intramolecular nucleotide base pairing between a 3' subdomain of the molecule and a 5' subdomain of the molecule, and (iii) a linkage domain, wherein the domains of (b)(i) and (b)(ii) form tandem repeat sequences interrupted by a signal sequence, and wherein the 3' toehold domain of (b)(i) is irreversibly bound to a protector strand, and (c) a nucleic acid primer comprising a domain complementary to the 3' toehold domain of the catalytic hairpin molecule of (a) and complementary to the 3' toehold domain of the catalytic hairpin molecule of (b). Two nucleic acids are considered "irreversibly bound" to each other if they are able to bind to each other and disassociate from each other under PER conditions. An example of "tandem repeat sequences" is depicted in FIGS. 21A-21B (see a*-a*). An example of "tandem repeat sequences interrupted by a signal sequence" is also depicted in FIGS. 21A-21B (see a*-S*-a*). A signal sequence, in some embodiments, may be at least 1 nucleotide, or at least 2 nucleotides (e.g., 1-20 nucleotides or at least 2, 3, 4, 5, 6, 7, 8, 9 or 10 nucleotides) arranged in an order that differs from the order of the nucleotides in tandem repeat domains. In some embodiments, the protector strand is linked to the 3' toehold domain of the at least one other catalytic hairpin molecule of (b), optionally through a loop domain (see, e.g., FIG. 42A).

Some aspects of the present disclosure provide methods of producing a single-stranded nucleic acid, comprising: combining in reaction buffer (a) an initial catalytic molecule comprising (i) an unpaired 3' toehold domain and (ii) a paired domain located 5' from the toehold domain formed by nucleotide base pairing between a displacement strand and a template strand containing the toehold domain, (b) a plurality of different catalytic molecules, each hairpin molecule comprising (i) an unpaired 3' toehold domain and (ii) a paired domain located 5' from the toehold domain formed by nucleotide base pairing between a displacement strand and a template strand containing the toehold domain, wherein the 3' toehold domain of each catalytic molecule is complementary to the displacement strand of one other catalytic molecule of the plurality; (c) an initial primer complementary to the 3' toehold domain of the initial catalytic molecule, (d) a polymerase having strand displacement activity, and (e) deoxyribonucleotide triphosphates (dNTPs), thereby forming a reaction mixture; and incubating the reaction mixture under conditions that result in nucleic acid polymerization, strand displacement and annealing, for a time sufficient to produce a single-stranded nucleic acid record that is longer than the initial primer.

In some embodiments, methods of producing a single-stranded nucleic acid comprise: combining in reaction buffer (a) an initial hairpin molecule comprising (i) an unpaired 3' toehold domain, (ii) a paired stem domain formed by intramolecular nucleotide base pairing between a 3' subdomain of the molecule and a 5' subdomain of the molecule, and (iii) a hairpin loop domain, (b) a plurality of different hairpin molecules, each hairpin molecule comprising (i) an unpaired 3' toehold domain, (ii) a paired stem domain formed by intramolecular nucleotide base pairing between a 3' subdomain of a hairpin molecule of the plurality and a 5' subdomain of a hairpin molecule of the plurality, and (iii) a loop domain, wherein the 3' toehold domain of each hairpin molecule is complementary to the 5' subdomain of one other hairpin molecule of the plurality; (c) an initial primer complementary to the 3' toehold domain of the initial hairpin molecule, (d) a polymerase having strand displacement activity, and (e) deoxyribonucleotide triphosphates (dNTPs), thereby forming a reaction mixture; and incubating the reaction mixture under conditions that result in nucleic acid polymerization, strand displacement and annealing, for a time sufficient to produce a single-stranded nucleic acid record that is longer than the initial primer.

Other aspects of the present disclosure provide methods of measuring time between molecular events, comprising: combining in reaction buffer (a) an initial catalytic molecule comprising (i) an unpaired 3' toehold domain and (ii) a paired domain located 5' from the toehold domain formed by nucleotide base pairing between a displacement strand and a template strand containing the toehold domain, (b) a plurality of different catalytic molecules, each catalytic molecule comprising (i) an unpaired 3' toehold domain and (ii) a paired domain located 5' from the toehold domain formed by nucleotide base pairing between a displacement strand and a template strand containing the toehold domain, wherein the 3' toehold domain of each catalytic molecule is complementary to the displacement strand of one other catalytic molecule of the plurality; (c) an initial primer complementary to the unpaired 3' toehold domain of the initial catalytic molecule, (d) a polymerase having strand displacement activity, and (e) deoxyribonucleotide triphosphates (dNTPs), thereby forming a reaction mixture; exposing the reaction mixture to a first molecular event; incubating the reaction mixture under conditions that result in nucleic acid polymerization, strand displacement and annealing, for a time sufficient to produce a single-stranded nucleic acid record; and exposing the reaction mixture to a second molecular event.

In some embodiments, methods of measuring time between molecular events comprise: combining in reaction buffer (a) an initial catalytic hairpin molecule comprising (i) an unpaired 3' toehold domain, (ii) a paired stem domain formed by intramolecular nucleotide base pairing between a 3' subdomain of the molecule and a 5' subdomain of the molecule, and (iii) a hairpin loop domain, (b) a plurality of different catalytic hairpin molecules, each hairpin molecule comprising (i) an unpaired 3' toehold domain, (ii) a paired stem domain formed by intramolecular nucleotide base pairing between a 3' subdomain of a hairpin molecule and a 5' subdomain of a hairpin molecule, and (iii) a loop domain, wherein the 3' toehold domain of each hairpin molecule is complementary to the 5' subdomain of one other hairpin molecule of the plurality; (c) an initial primer complementary to the unpaired 3' toehold domain of the initial hairpin molecule, (d) a polymerase having strand displacement activity, and (e) deoxyribonucleotide triphosphates (dNTPs), thereby forming a reaction mixture; exposing the reaction mixture to a first molecular event; incubating the reaction mixture under conditions that result in nucleic acid polymerization, strand displacement and annealing, for a time sufficient to produce a single-stranded nucleic acid record; and exposing the reaction mixture to a second molecular event.

Yet other aspects of the present disclosure provide molecular motor systems, comprising: (a) an initial nucleic acid molecule comprising (i) an unpaired 3' toehold domain and (ii) a paired domain located 5' from the toehold domain that is formed by nucleotide base pairing between a displacement strand and a template strand containing the toehold domain; (b) a second nucleic acid molecule comprising (i) an unpaired 3' toehold domain and (ii) a paired domain located 5' from the toehold domain that is formed by nucleotide base pairing between a displacement strand and a template strand containing the toehold domain, wherein the unpaired 3' toehold domain of the second nucleic acid molecule is complementary to the displacement strand of the initial nucleic acid molecule; and (c) a primer complementary to nucleotides located in the unpaired 3' toehold domain of the initial nucleic acid molecule.

Still other aspects of the present disclosure provide molecular recording systems, comprising: (a) an initial hairpin molecule comprising (i) an unpaired 3' toehold domain, (ii) a paired stem domain formed by intramolecular nucleotide base pairing between a 3' subdomain of the molecule and a 5' subdomain of the molecule, and (iii) a loop domain, wherein the initial hairpin molecule is linked to a target biomolecule; (b) a second hairpin molecule comprising (i) an unpaired 3 toehold domain, (ii) a paired stem domain formed by intramolecular nucleotide base pairing between a 3' subdomain of the molecule and a 5' subdomain of the molecule, and (iii) a loop domain, wherein the second hairpin molecule is linked to a target biomolecule, and wherein the 5' subdomain of the initial hairpin molecule is complementary to the 5' subdomain of the second hairpin molecule; (c) two primers, one of which is complementary to the unpaired 3 toehold domain of the initial hairpin molecule and the other of which is complementary to the unpaired 3' toehold domain of the second hairpin molecule; (d) a plurality of catalytic hairpin molecules, each molecule comprising (i) an unpaired 3' toehold domain, (ii) a paired stem domain formed by intramolecular nucleotide base pairing between a 3' subdomain of the molecule and a 5' subdomain of the molecule, and (iii) a loop domain, wherein the 5' subdomain of each hairpin molecule of the plurality is complementary to the 5' subdomain of one other hairpin molecule of the plurality, wherein the 3' toehold domain of one of the hairpin molecules of the plurality is complementary to the 5' subdomain of the initial hairpin molecule, and wherein the 3' toehold domain of another of the hairpin molecules of the plurality is complementary to the 5' subdomain of the second hairpin molecules; and (e) polymerase having strand displacement activity.

Still other aspects of the present disclosure provide a method of recording distances between target biomolecules, comprising combining in reaction buffer (a) an initial hairpin molecule comprising (i) an unpaired 3' toehold domain, (ii) a paired stem domain formed by intramolecular nucleotide base pairing between a 3' subdomain of the molecule and a 5' subdomain of the molecule, and (iii) a loop domain, wherein the initial hairpin molecule is linked to a target biomolecule. (b) a second hairpin molecule comprising (i) an unpaired 3' toehold domain, (ii) a paired stem domain formed by intramolecular nucleotide base pairing between a 3' subdomain of the molecule and a 5' subdomain of the molecule, and (iii) a loop domain, wherein the second hairpin molecule is linked to a target biomolecule, and wherein the 5' subdomain of the initial hairpin molecule is complementary to the 5' subdomain of the second hairpin molecule, (c) two primers, one of which is complementary to the unpaired 3' toehold domain of the initial hairpin molecule and the other of which is complementary to the unpaired 3' toehold domain of the second hairpin molecule. (d) a plurality of hairpin molecules, each molecule comprising (i) an unpaired 3' toehold domain, (ii) a paired stem domain formed by intramolecular nucleotide base pairing between a 3' subdomain of the molecule and a 5' subdomain of the molecule, and (iii) a loop domain, wherein the 5' subdomain of each hairpin molecule of the plurality is complementary to the 5' subdomain of one other hairpin molecule of the plurality, wherein the 3' toehold domain of one of the hairpin molecules of the plurality is complementary to the 5' subdomain of the initial hairpin molecule, and wherein the 3' toehold domain of another of the hairpin molecules of the plurality is complementary to the 5' subdomain of the second hairpin molecule, and (e) polymerase having strand displacement activity, and deoxyribonucleotide triphosphates (dNTPs), thereby forming a reaction mixture; and incubating the reaction mixture under conditions that result in nucleic acid polymerization, strand displacement and annealing, for a time sufficient to produce a double-stranded nucleic acid record.

BRIEF DESCRIPTION OF DRAWINGS

FIG. 1C shows another diagram of an example of a primer exchange reaction (PER): (i) A primer exchange reaction, which uses a catalytic hairpin to produce transcripts of the form a b. (ii)

An example reaction implementation with a hairpin that uses a G-C pair as a stop sequence. Other stop sequences are described herein. (iii) A primer exchange reaction cycle. First, primer a binds to the catalytic hairpin (step 1). Then, the b domain is concatenated onto a with a strand displacing polymerase until it reaches a stop sequence (step 2). Branch migration displaces the synthesized b domain (step 3). The a b transcript dissociates from the hairpin, and the hairpin is recycled (step 4). (iv) PAGE denaturing gels depicting a reaction time series and hairpin concentration gradient for a single primer exchange reaction. For both experiments, primer concentration was fixed at 100 nM and reactions were incubated at 37° C. with 10 μM of dATP, dTTP, and dCTP. Lanes 11 and 13 correspond to identical conditions.

Figure 2B:

FIG. 2A shows a diagram of examples of PER cascades. (i) Schematic for combining several PER hairpins and other reagents for autonomous stepwise growth of a primer sequence. (ii) Reaction diagram for five elongation steps, patterned by hairpins A, B, C, D, and E. (iii) Denaturing gel demonstrating differential extension with different subsets of the hairpin species present. Reactions were incubated for 4 hours at 37° C., with primer concentrations at 100 nM, hairpins at 10 nM, and dATP, dTTP, and dCTP at 10 μM each. (iv) Schematic for parallel synthesis of 40 staple strands for an origami structure and AFM image of three of these structures aggregated with origami borders overlaid. FIG. 2B shows examples of state transition diagrams. A hairpin acts catalytically to append the 3 domain onto a primer having the 1 and 2 domains.

Figure 3A:
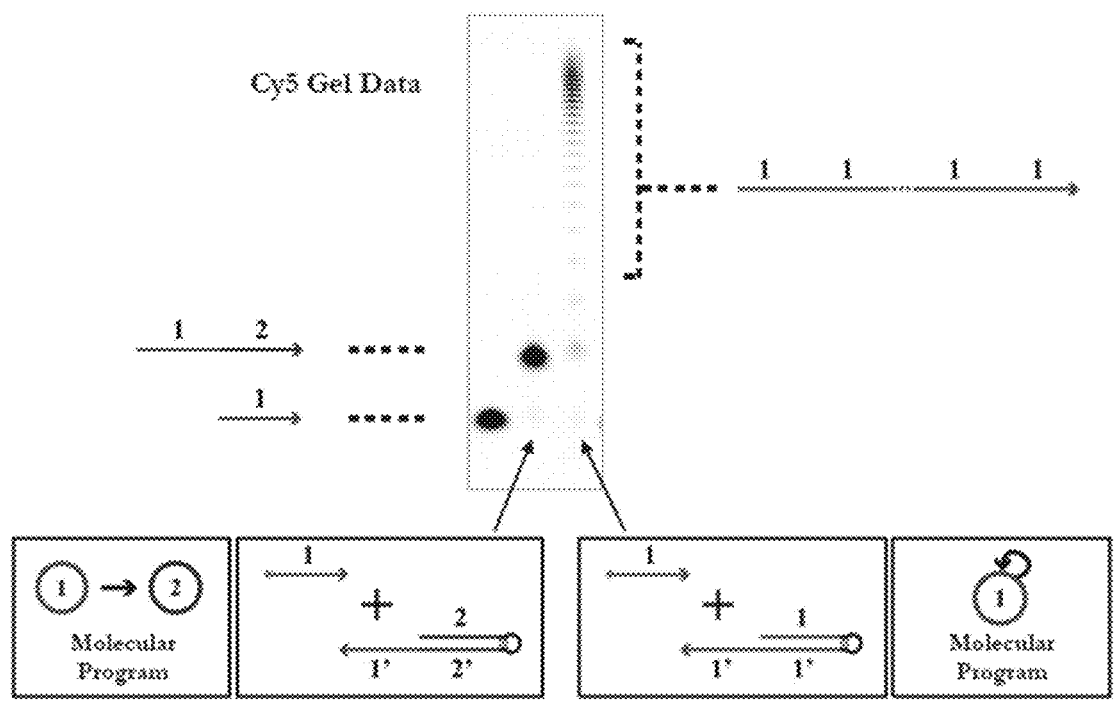
Figure 3B:
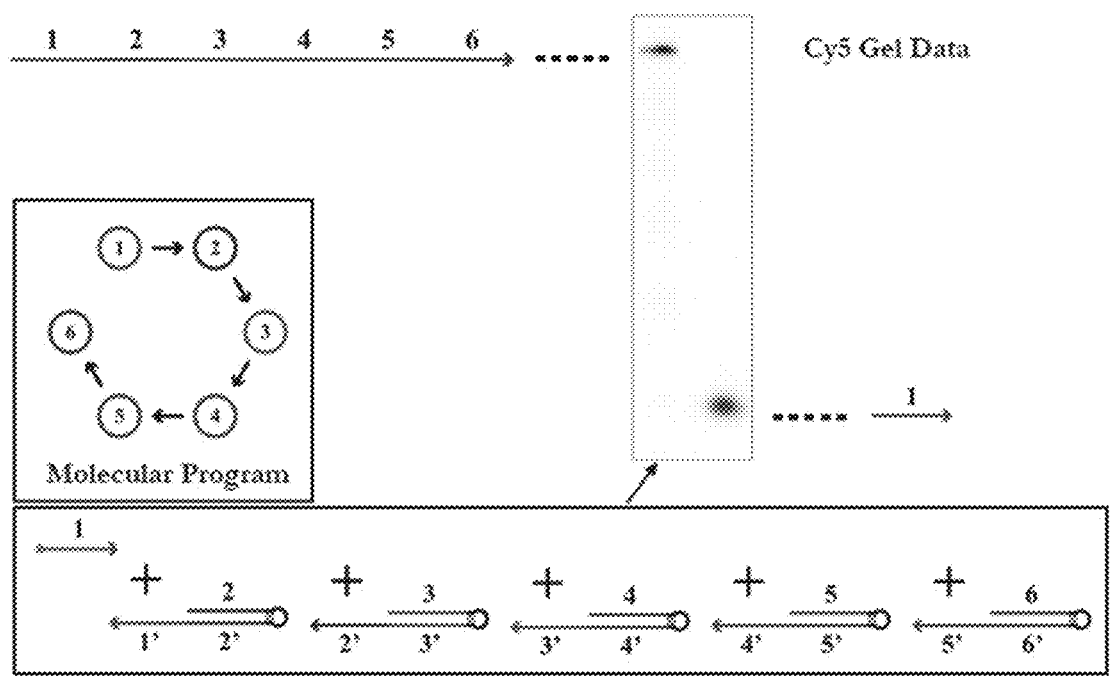

FIGS. 3A and 3B show images demonstrating that PER elongated strands according to prescribed pathways.

Figure 4:
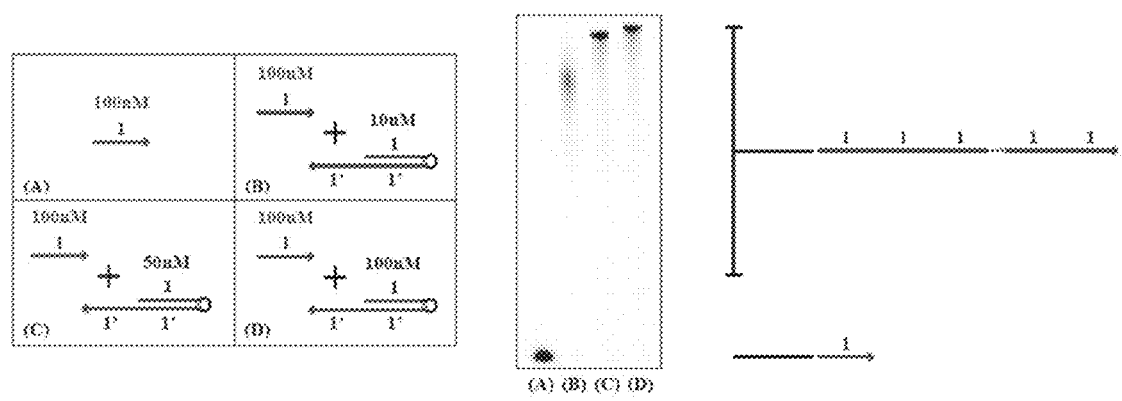

FIG. 4 shows images demonstrating that PER can be used to construct a synthetic telomerase. Using one hairpin, a system that copies a specific 10 nucleotide sequence was implemented. Lane (A) shows the primer without any hairpin, and Lanes (B)-(D) show results with different concentrations of hairpin. Reactions were incubated for 4 hours at 37° C.

Figure 5:
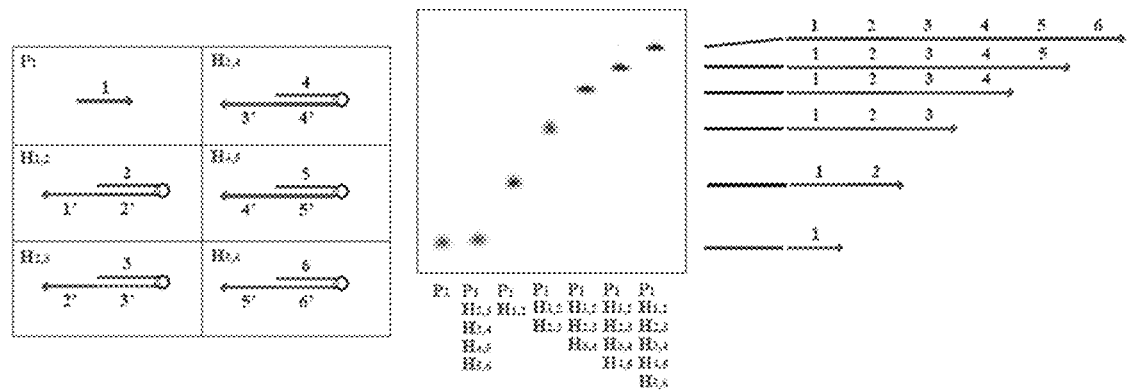

FIG. 5 shows images demonstrating a multi-step PER.

Figure 6:
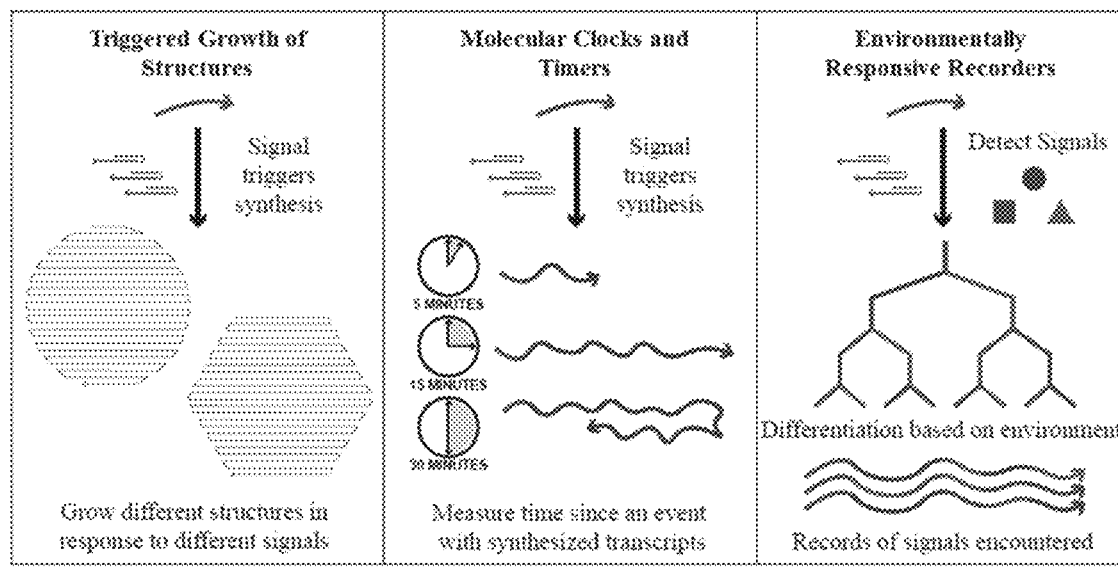

FIG. 6 shows examples of several applications in which PER may be used as a tools, including triggered assembly of complex nanostructures (panel 1), molecular clocks to measure time and timers to control signals over time (panel 2), and systems that differentiate in response to and recording signals over time (panel 3).

Figure 7:
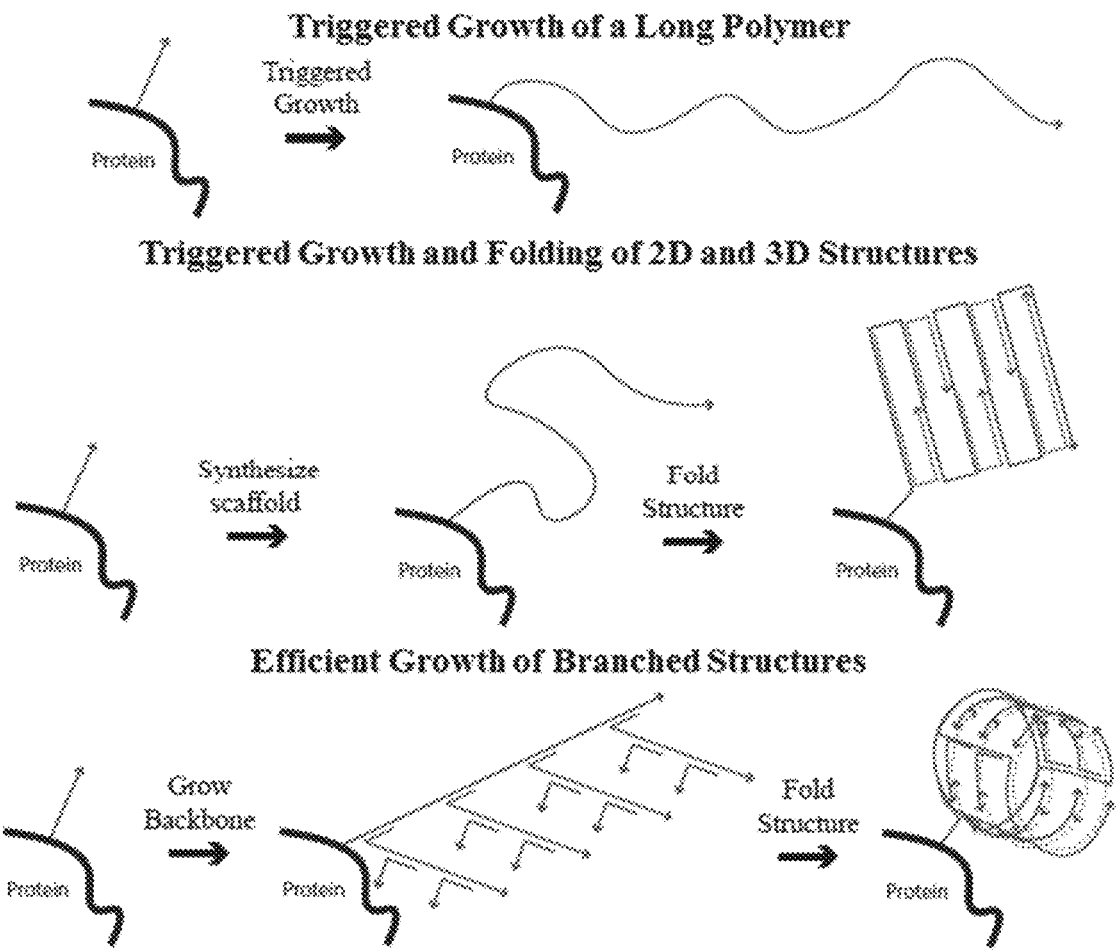

FIG. 7 shows examples of several applications in which PER may be used for triggered assembly of complex nanostructure. The top panel shows triggered assembly of a long strand of fixed length. The middle panel shows the long strands being folded into arbitrary 2D and 3D shapes. The bottom panel shows assembly of a dendritic backbone structure that can also be folded into shapes.

Figures 8A, 8B:
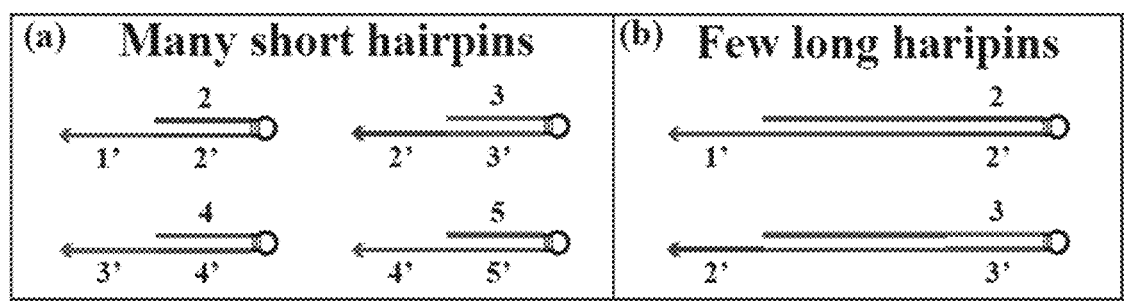

FIGS. 8A-8B show two example approaches for scaling up the assembly of long scaffold strands. FIG. 8A depicts increasing the number of catalytic hairpins, and FIG. 8B depicts increasing the length of copy region within each hairpin.

Figures 9A, 9B, 9C:
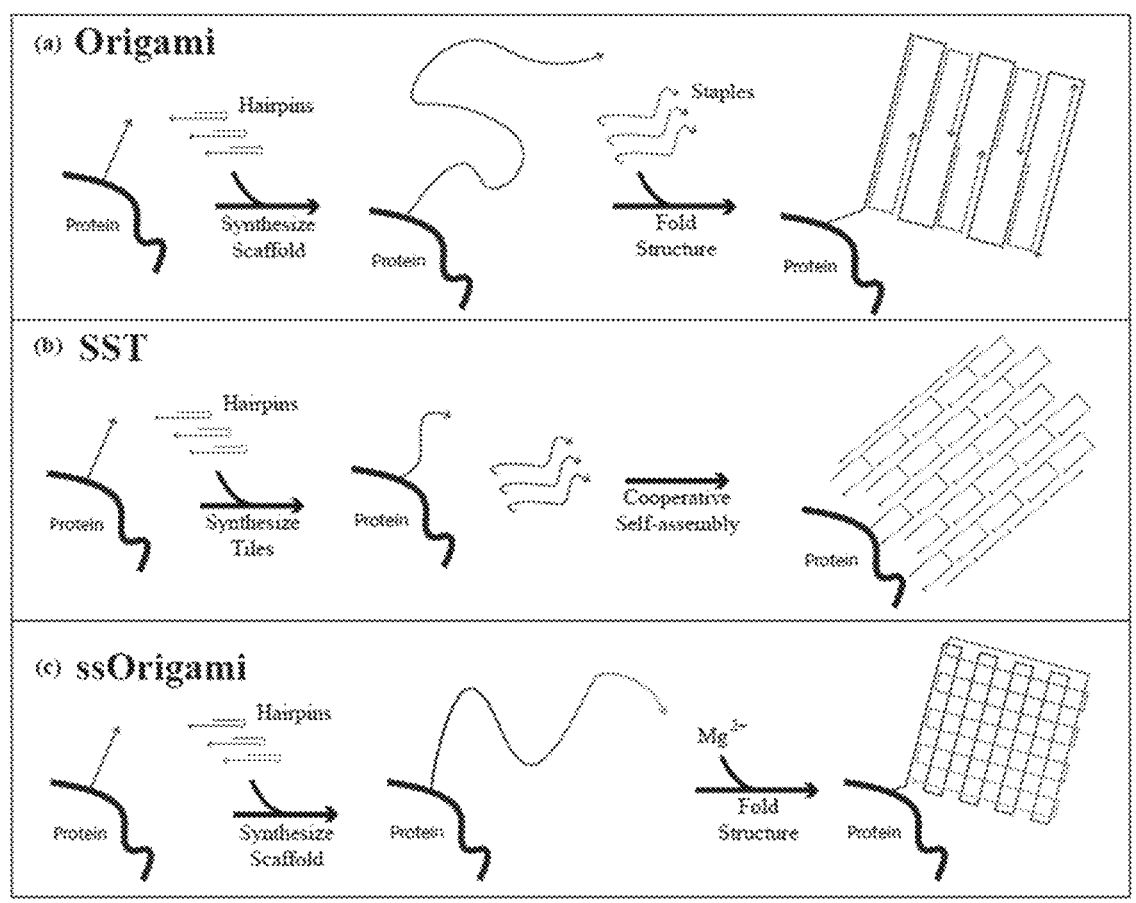

FIGS. 9A-9C show three example approaches for triggering assembly of nucleic acid nanostructures using PER. FIG. 9A shows an example of triggered assembly of a conventional DNA origami nanostructure. FIG. 9B shows an example of triggered assembly of a single-stranded tile nanostructure. FIG. 9C shows an example of triggered assembly of a single-stranded DNA origami nanostructure.

Figures 10A, 10B, 10C:
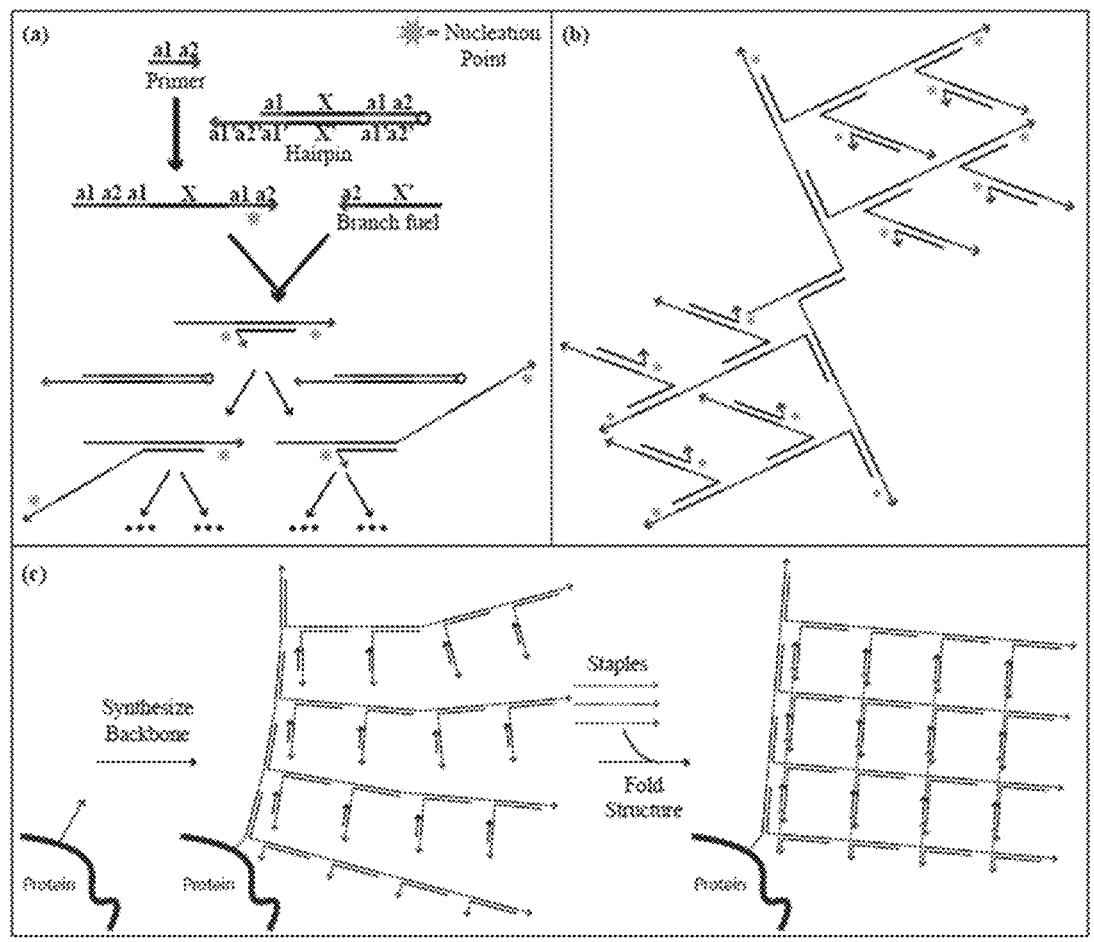

FIGS. 10A-10C show an example a mechanism for dendritic assembly using PER. FIG. 10A shows triggered synthesis of a dendrimer with exponential growth kinetics using a single stranded fuel (nucleic acid) in addition to a hairpin. FIG. 10B shows an example of a dendritic structure. FIG. 10C shows a dendritic backbones folded into specific 2D and 3D shapes using staple strands (short oligonucleotides).

Figure 11:
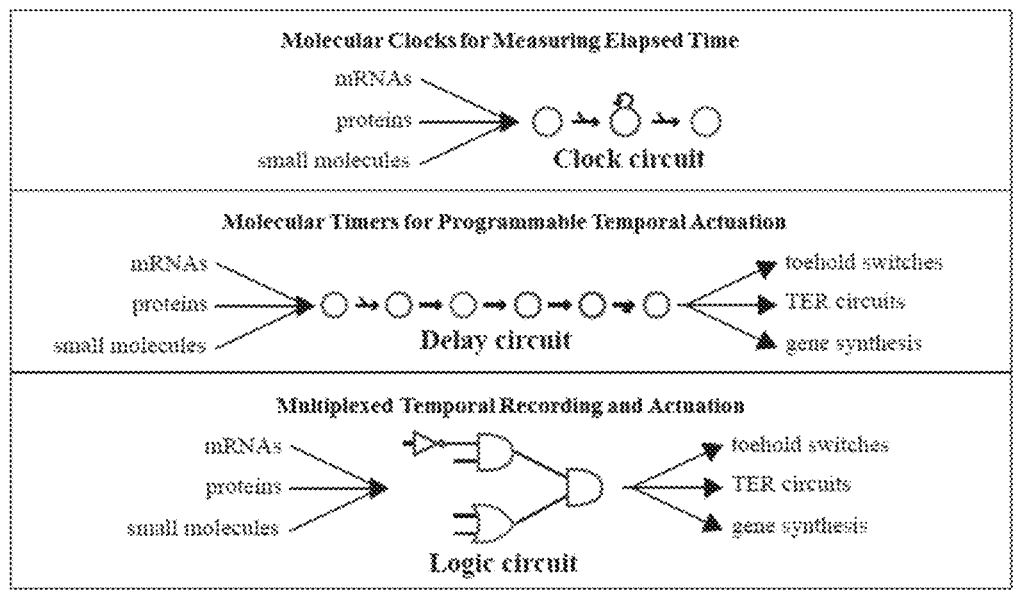

FIG. 11 shows examples of several applications in which PER may be used as molecular clocks to measure time and as timers to control signals over time. The top panel shows a schematic of PER being used as molecular clocks for measuring elapsed time. The middle panel shows a schematic of PER being used as molecular timers for programmable temporal actuation. The bottom panel shows a schematic of PER being used for multiplexed temporal recording and actuation.

Figures 12A, 12B, 12C, 12D, 12E, 12F:
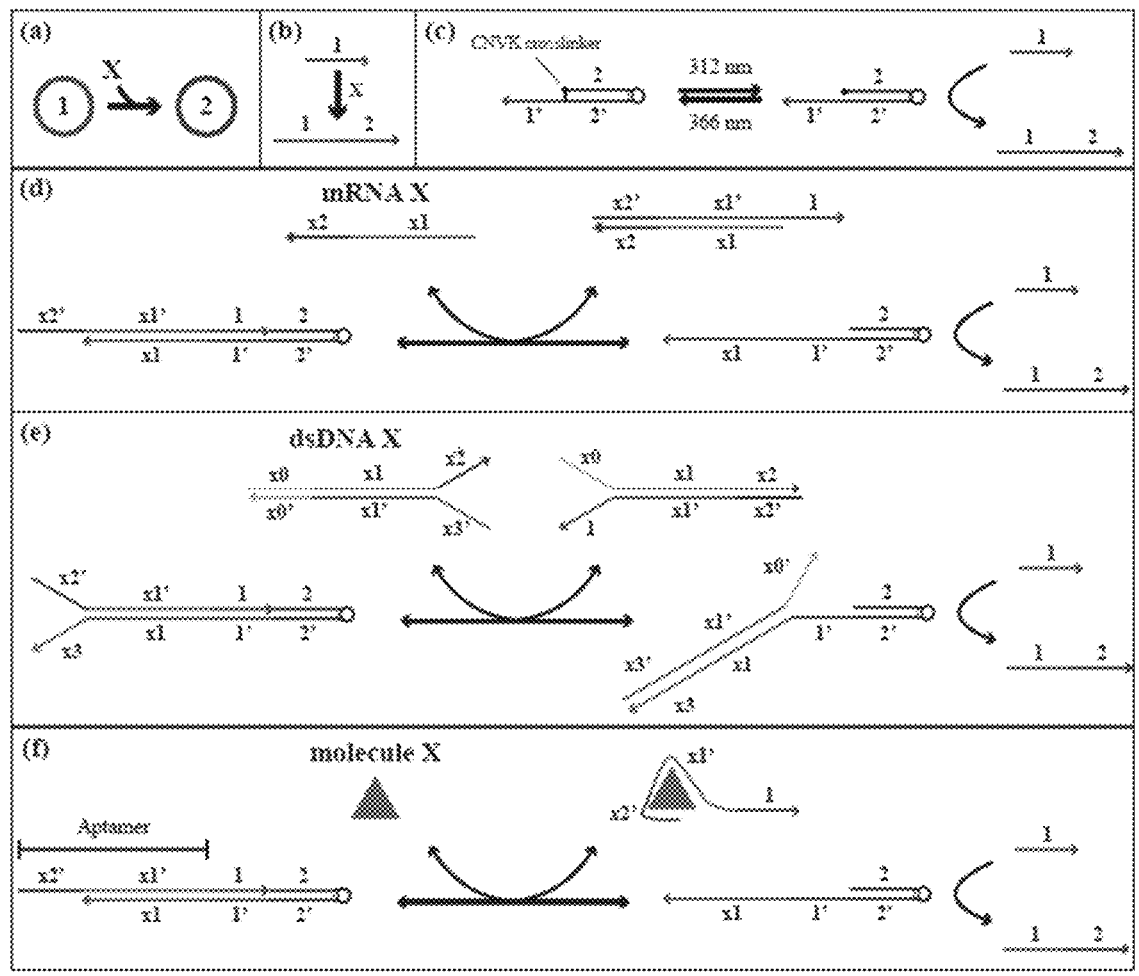

FIGS. 12A-12F show examples of signal detection modules. FIG. 12A shows an abstraction for conditional state transitions. FIG. 12B shows detection involving an irreversible primer exchange step. FIG. 12C shows a reversible crosslinking reaction[57] activating and deactivating a hairpin with specific wavelengths of light. FIG. 12D show mRNA signals detected using a protector strand that occludes the binding site on the hairpin in the absence of signal. In some cases, this input may also be ssDNA or another single-stranded nucleic acid. In some embodiments, this trigger signal is a strand synthesized by a separate PER reaction. FIG. 12E shows detection of double stranded DNA (dsDNA) achieved by appending toehold regions with PCR.[45] FIG. 12F shows aptamers recognizing small molecule and protein targets to unblock the hairpin.

Figures 13A, 13B, 13C:
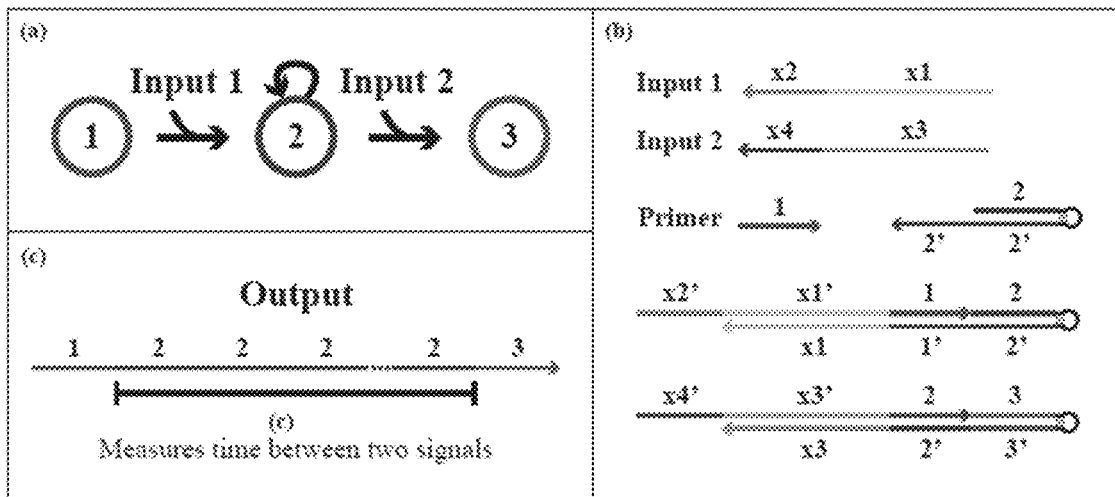

FIGS. 13A-13C show examples of molecular clocks. FIG. 13A shows an input triggering a transition to a telomerization state, and a second input halting this. FIG. 13B shows one hairpin being used per state transition, as in FIGS. 12A-12F. FIG. 13C shows the length of the output indicating the time elapsed between the two inputs.

Figures 14A, 14B, 14C:
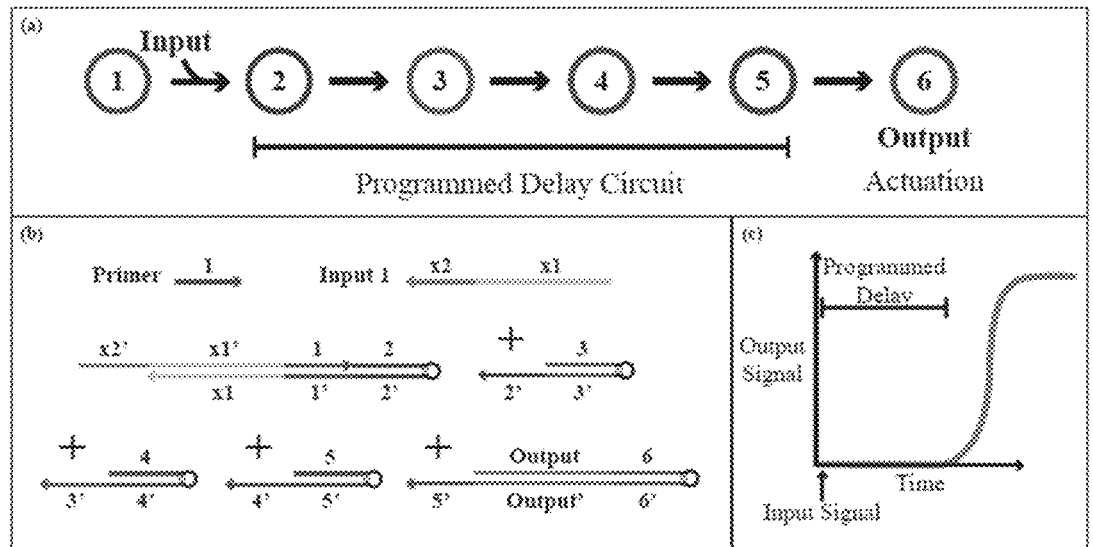

FIGS. 14A-14C show examples of molecular timers. FIG. 14A shows a timer using a delay circuit, whereby primers undergo a fixed number of state transitions before actuation. FIG. 14B shows one hairpin per state transition. FIG. 14C depicts an output curve.

Figures 15A, 15B, 15C, 15D:
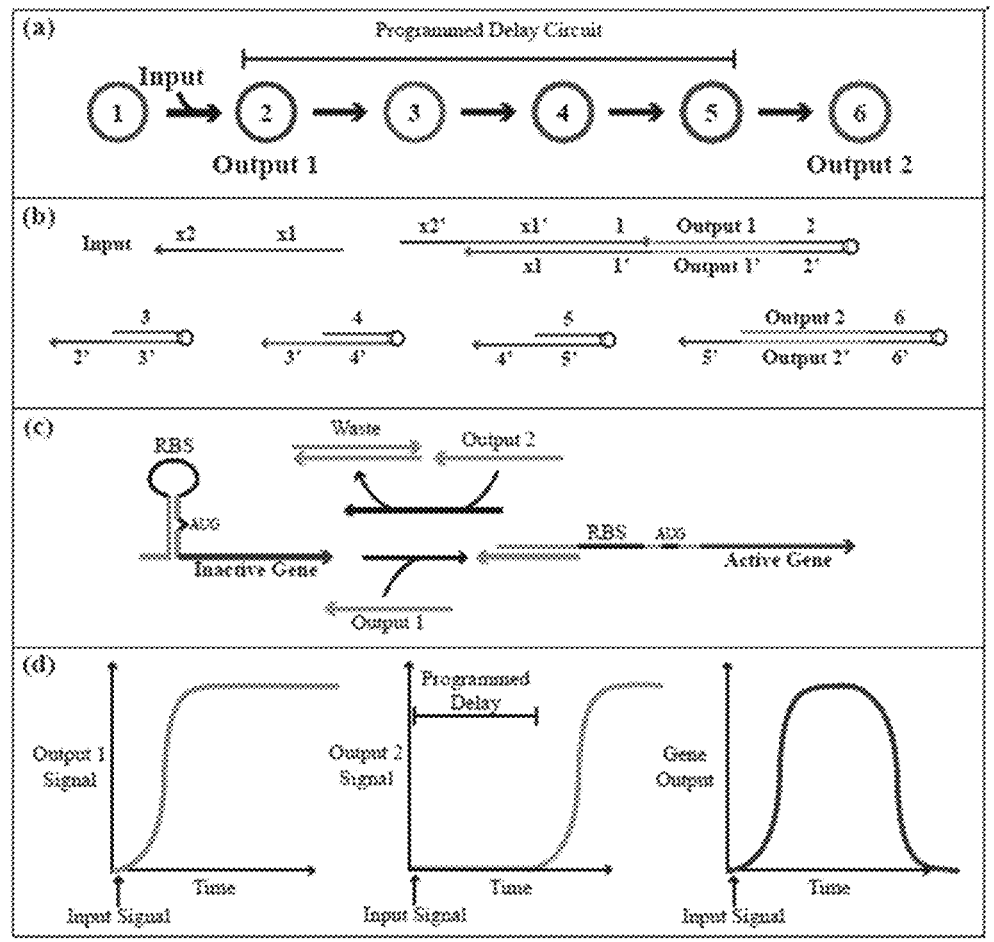
Figures 16A, 16B, 16C, 16D, 16E, 16F, 16G, 16H, 16I:
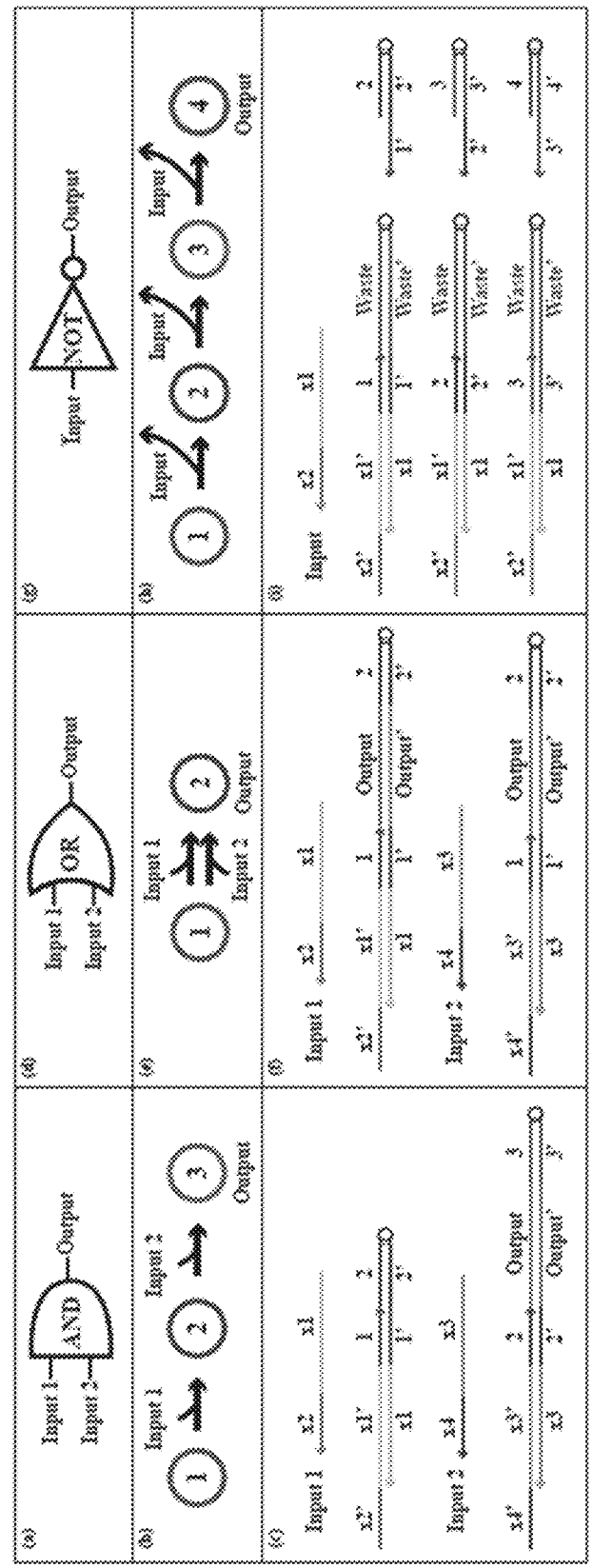

FIGS. 15A-15D show examples of recording a pulse of protein synthesis using PER. FIG. 15A shows a programmed delay between Outputs 1 and 2 providing the basis for temporal control of toehold switch activation. FIG. 15B shows an example of a molecular implementation. FIG. 15C shows output sequences produced by the circuit programmed to activate and then deactivate a toehold switch. FIG. 15D shows traces of outputs.

FIGS. 16A-16I shows examples of PER logic. Logic operations AND (FIGS. 16A-16C), OR (FIGS. 16D-16F) and NOT (FIGS. 16G-16I) can be implemented with PER reaction graphs.

Figures 17A, 17B, 17C:
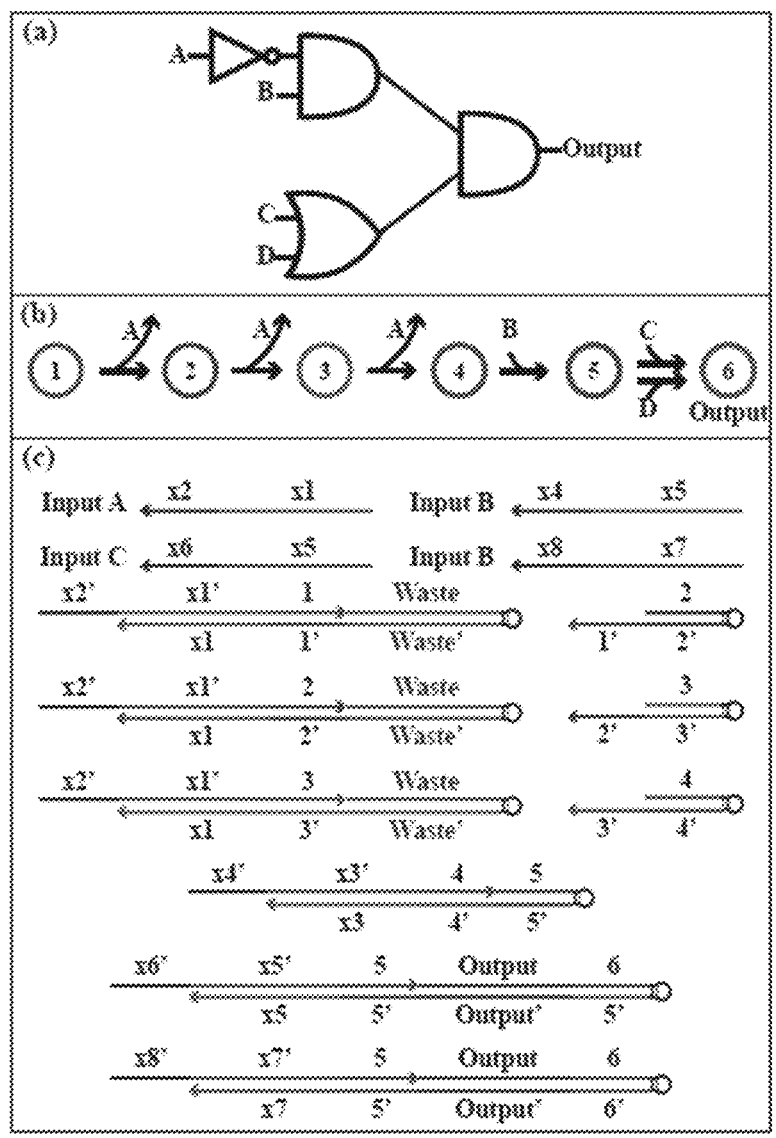

FIGS. 17A-17C show examples of logic computation using PER. FIG. 17A shows an example digital logic circuit. FIG. 17B shows a system involving 6 states. FIG. 17C shows a molecular implementation involving signal detection (FIGS. 12A-12F) and logic (FIGS. 16A-16I) modules integrated into the circuit.

Figure 18:
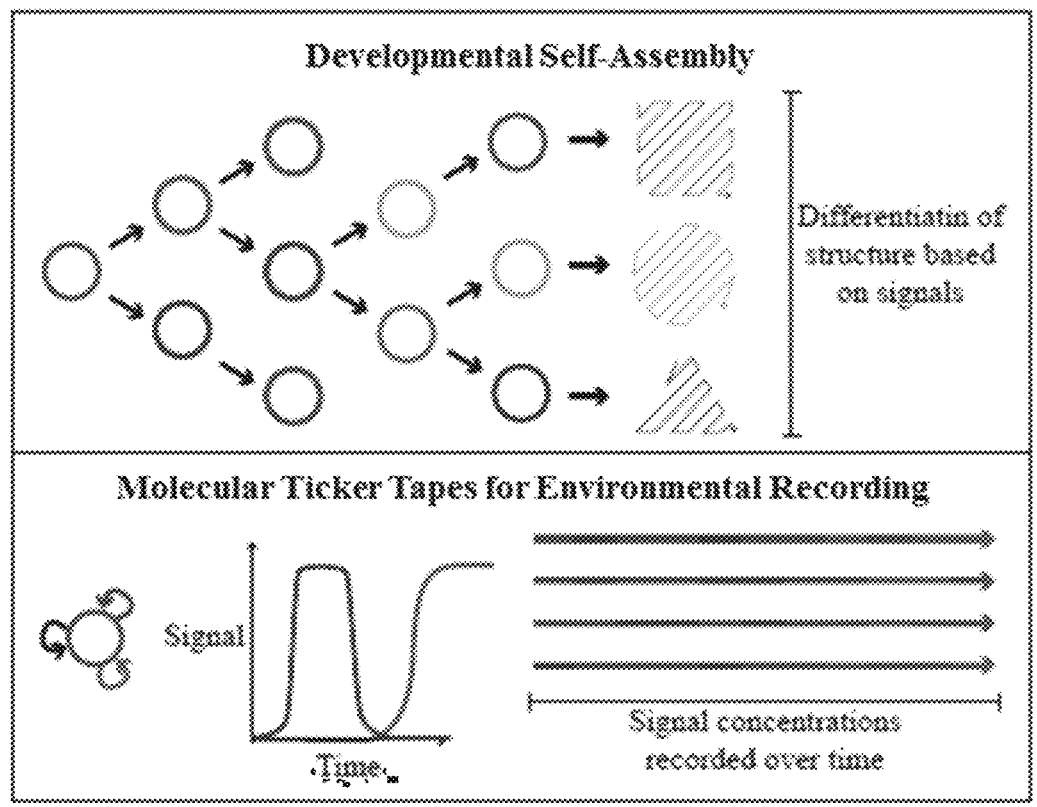

FIG. 18 shows examples of two applications in which PER may be used for implementing systems that differentiate in response to and recording signals over time. The top panel shows an example of developmental self-assembly, whereby different structural growth in situ follows developmental pathways. The bottom panel shows an example of molecular ticker tapes that record the time traces of signals over time.

Figures 19A, 19B, 19C:
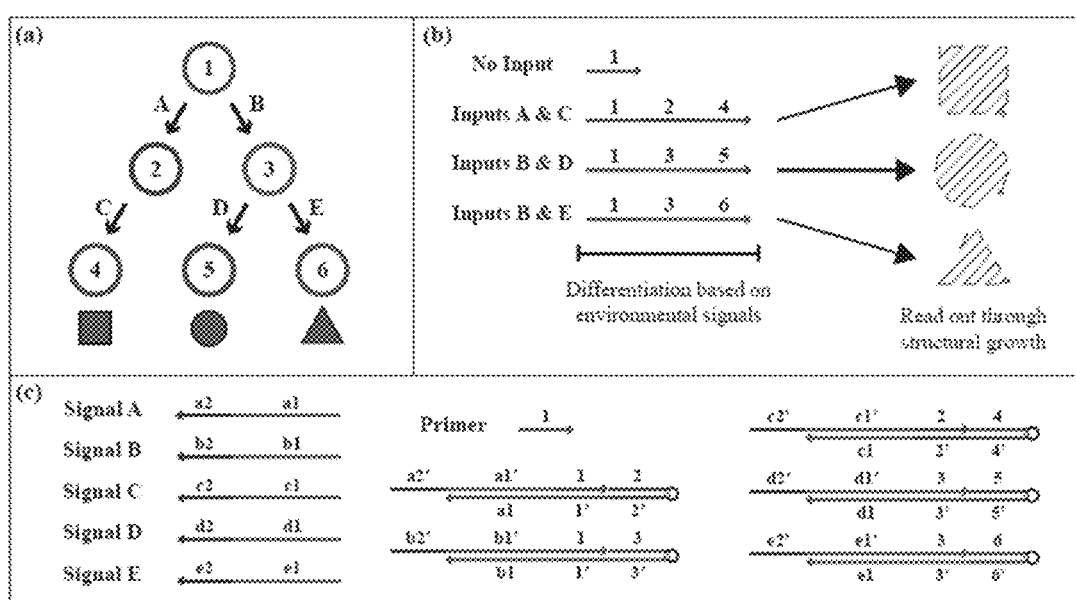

FIGS. 19A-19C show examples of developmental self-assembly using PER. FIG. 19A shows primers undergoing state differentiation based upon signals (A-E) encountered over time. FIG. 19B shows differentiated states triggering in situ synthesis of shapes. FIG. 19C shows state transitions implemented as in FIGS. 12A-12F.

Figures 20A, 20B, 20C, 20D:
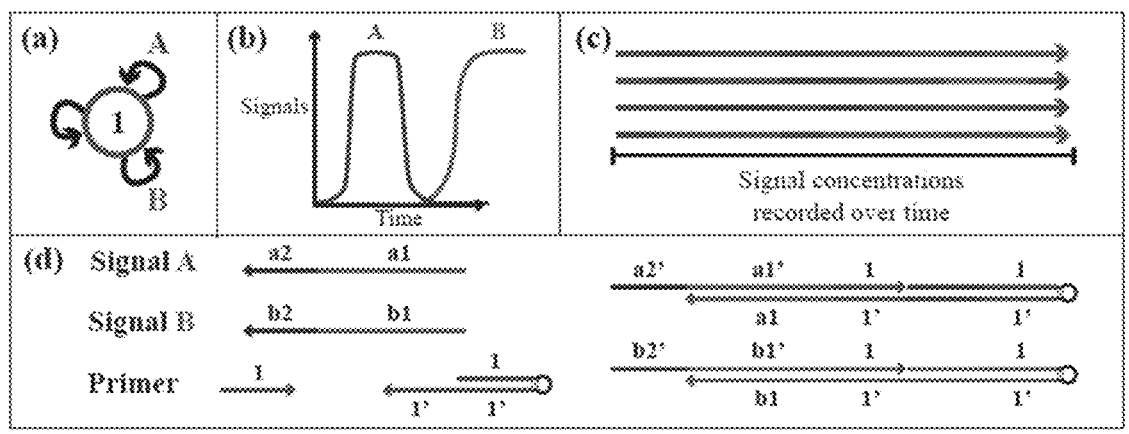
Figures 21A, 21B, 21C, 21D:
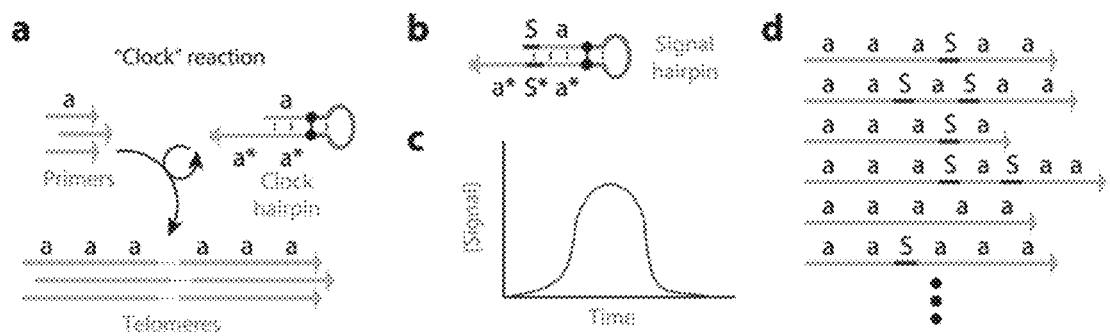

FIGS. 20A-20D show examples of molecular ticket tape construction using PER. FIG. 20A shows a ticker tape is a telomerization circuit with one transition serving as a clock and then one per signal type. FIG. 20B shows a signal trace producing the transcripts in FIG. 20C with signal histories encoded in them. FIG. 20D shows a system requiring one constitutively active telomerization hairpin and detectors for each signal.

FIGS. 21A-21D show a one-signal hairpin system. (FIG. 21A) A hairpin that copies the a domain onto an a primer is used to clock reactions by continuously appending domains to transcript sequences. (FIG. 21B) A hairpin that copies a couple extra bases (the S domain) in front of the repeated domain a onto transcript records serves as the signal. (FIG. 21C) A hypothetical signal concentration curve. (FIG. 21D) Diagrammatic illustration of transcripts that contain signal domains S intercalated within the repeated a domains according to the time-varying signal concentration.

Figure 22:
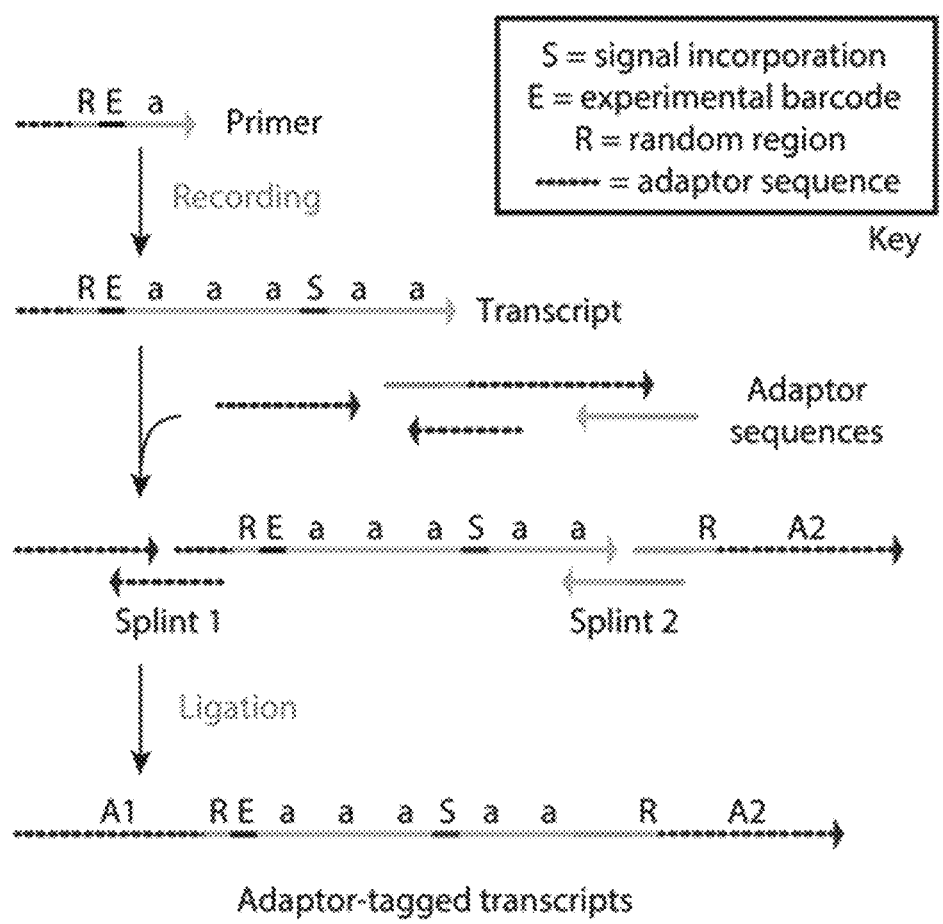

FIG. 22 shows an example of adaptor tagging. After recording produces transcripts from the initial primer sequences, adaptor sequences are introduced and ligated to either end of the transcripts using a couple of splinting sequences.

Figures 23A, 23B:
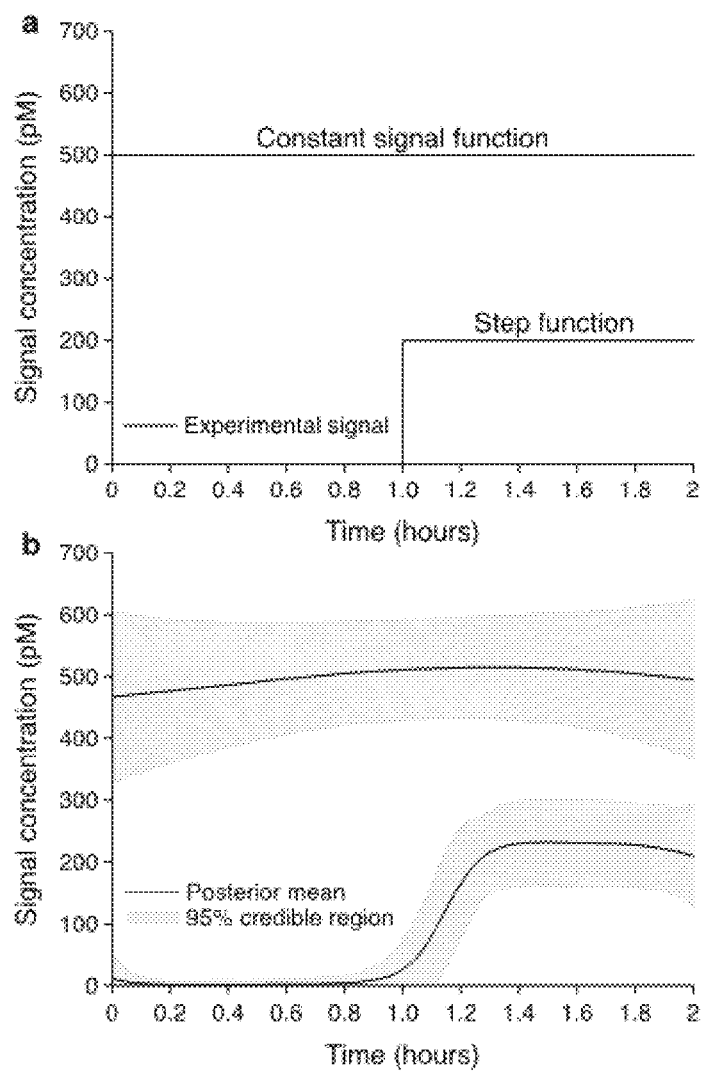

FIGS. 23A-23B show statistical inferences of signal concentrations from Experiments B and C. (FIG. 23A) Experiment B employed a constant signal concentration of 500 μM (top), while Experiment C employed a step signal function, plateauing at 200 μM after one hour. (FIG. 23B) Inference of the signal concentrations for the two experiments based on 300 transcripts having 179 total signals (Experiment B, top) and 1,000 transcripts having 127 total signals (Experiment C, bottom). Solid lines denote the mean of the posterior distribution (based on 100 samples post burn-in), while grey denotes the 95% credible regions for the two inferences. Both experiments were normalized so that the time-averaged mean of the posterior distribution for Experiment B equals 500 μM.

Figure 24:
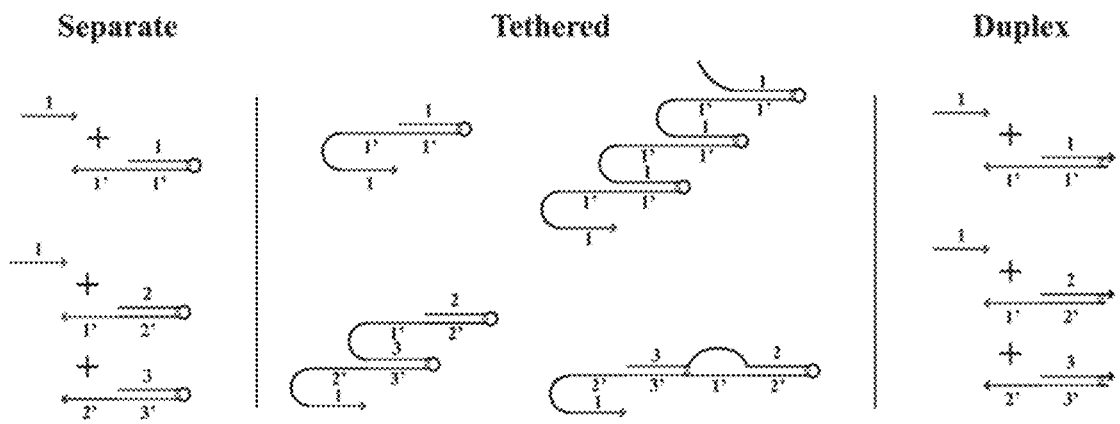

FIG. 24 shows single catalytic hairpin molecules (left panel), tethered catalytic hairpin molecules (middle panel) and duplex catalytic molecules (right panel).

Figure 25:
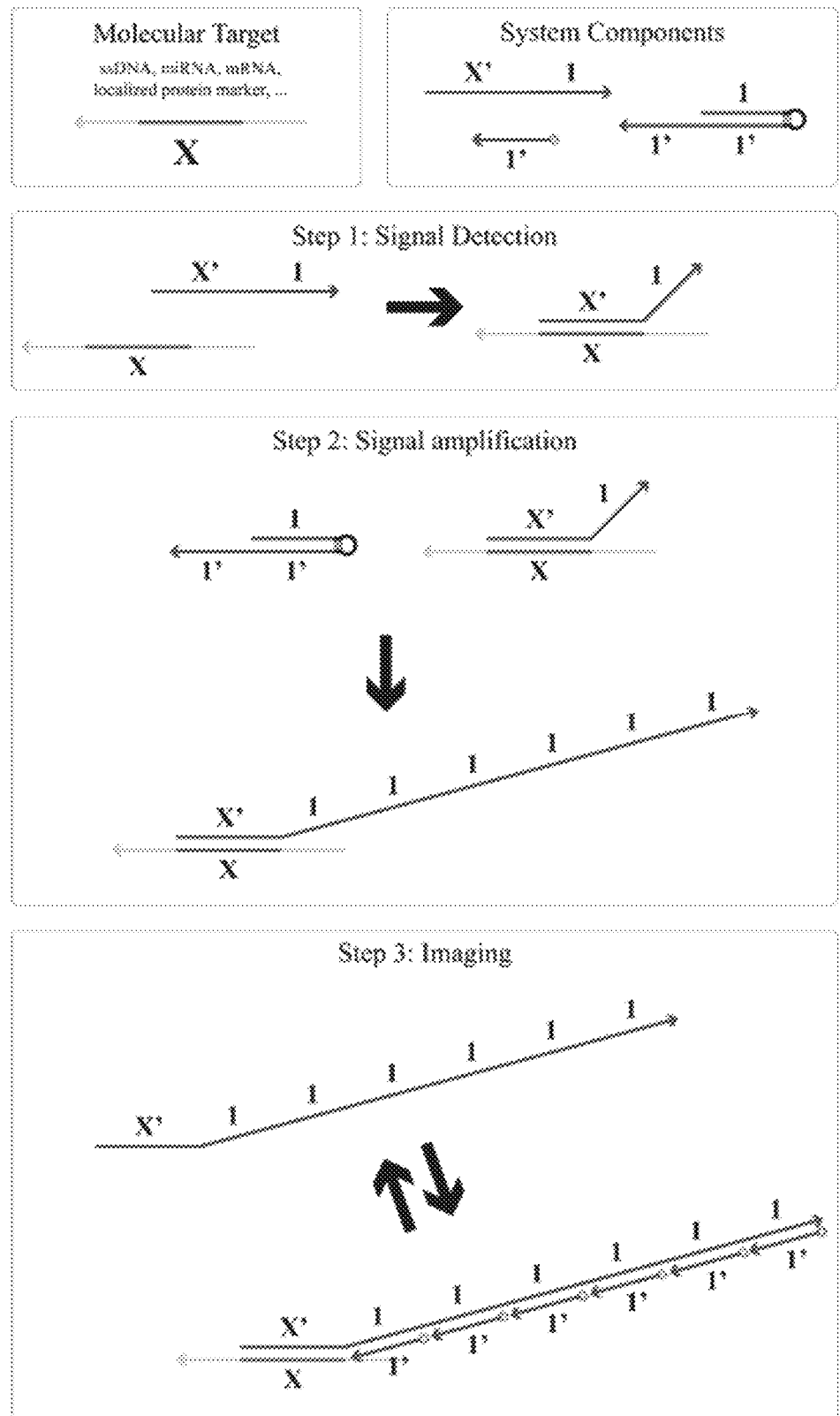

FIG. 25 show an example PER system for molecular target detection.

FIGS. 26A-26E show examples of a PER nanodevice. (FIG. 26A) Schematic for nanodevice, which detects a miRNA target and inhibits an independent gene. (FIG. 26B) Synthetic nucleotides, iso-dG and iso-dC, which are used as a stop sequence for four-letter code synthesis. (FIG. 26C) System setup and reaction diagram for nanodevice. The oncogenic miR-19a sequence triggers the cleavage of a fragment of the Twist gene (TWT) through the synthesis of a 10-23 DNAzyme sequence (DZ-TWT) by the A. B, and C hairpins. (FIG. 26D) Sequence breakdown of miRNA target (miR-19a) with DNAzyme (DZ-TWT) appended. Binding regions of the nascent primer strand are indicated by lines above the sequence, and the catalytic domain of the DNAzyme is depicted with dotted lines. (FIG. 26E) PAGE denaturing gel validating the miRNA and Twist mRNA fragment states given different hairpins in the incubation solution. Reactions were incubated for 4 hours at 37° C.

FIGS. 27A-27E show examples of label-free biosensors using PER. (FIG. 27A) Schematic for implementing a synthetic telomerase with a single PER hairpin. (FIG. 27B) A PAGE denaturing gel showing telomerization under different hairpin concentrations. Primers were incubated with the given hairpin concentrations for 4 hours at 37° C. (FIG. 27C) Schematic for label-free biosensor, where a miRNA target activates the synthesis of fluorescent telomere strands. (FIG. 27D) System components and reaction diagram for the biosensor. A gated hairpin (A) and telomerase hairpin (B) are designed to react to the detection of a miRNA signal and concatenate repeats of the human telomeric sequence TTAGGG, into which Thioflavin (ThT) intercalates. (FIG. 27E) A native PAGE gel showing conditional telomerization in the presence of 10 nM miRNA signal. Target detection can be visualized with a blue light transilluminator through the amber filter unit (vis), and the fluorescence of the reactions was also visualized on a Typhoon scanner (FAM).

FIGS. 28A-28E show examples of logic computation with PER. (FIG. 28A) Operational schematic for evaluating logic expressions with RNA inputs. (FIG. 28B) miR-19a OR TWT gate reaction components and a PAGE denaturing gel depicting transcript production in response to the different RNA inputs. True outputs are read by looking for transcripts of a particular length, indicated by the dotted lines. Reaction setup and PAGE denaturing gel results are also shown for (FIG. 28C) miR-19a AND TWT, (FIG. 28D) NOT miR-21, and (FIG. 28E). miR-19a OR TWT) AND (NOT miR-21).

FIGS. 29A-29D show examples of an event recording with PER. (FIG. 29A) Schematic for event recorder, which produces PER transcripts in response to time-varying RNA signals. (FIG. 29B) Toehold exchange mechanism for activation of gated hairpins. (FIG. 29C) System components and reaction diagram for recorder. Four gated hairpins (A, B, C, and D) are used to program the synthesis of different sequences in response to different orders of witnessing two RNA targets—miR-19a and a fragment of the Twist mRNA (TWT). (FIG. 29D) A PAGE denaturing gel shows transcripts of different lengths recorded for different RNA signal spikes at 1 and 3 hours into a 5 hour reaction at 37 C. See Methods section for additional details.

Figures 30A, 30B:
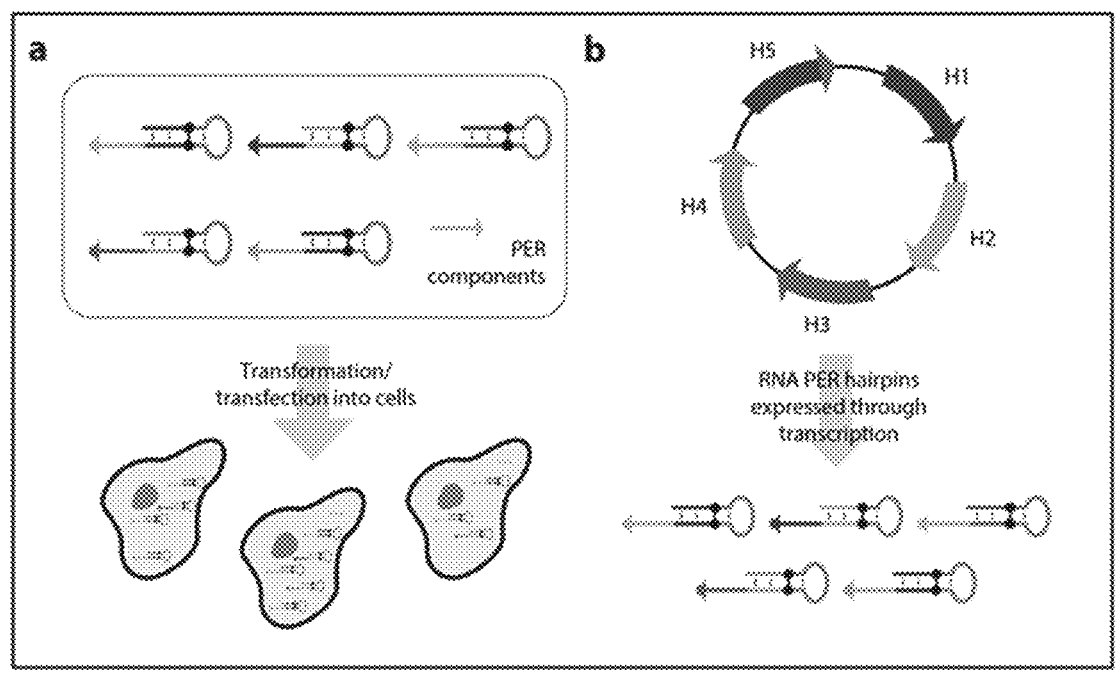

FIGS. 30A-30B shows an example of how to implement PER in vivo. Two strategies for in vivo PER cascades are presented. (FIG. 30A) In the first, the components are directly introduced into cells through transformation or transfection. Some cells will receive all components, enabling successful PER synthesis. (FIG. 30B) The second strategy encodes the hairpin PER components in either a plasmid or the genome, and hairpins are expressed as RNA constructs for programming the real-time synthesis of RNA oligos.

Figure 31A:
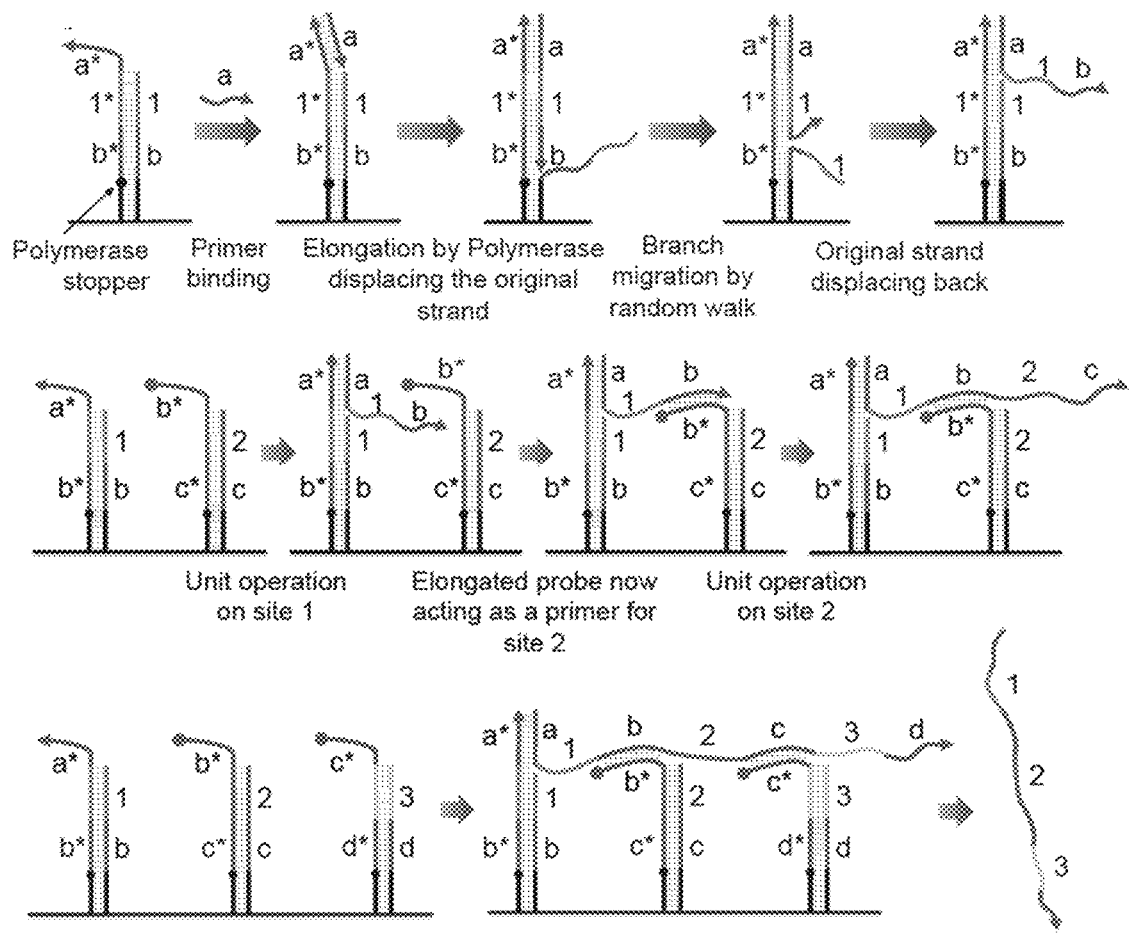
Figure 31B:
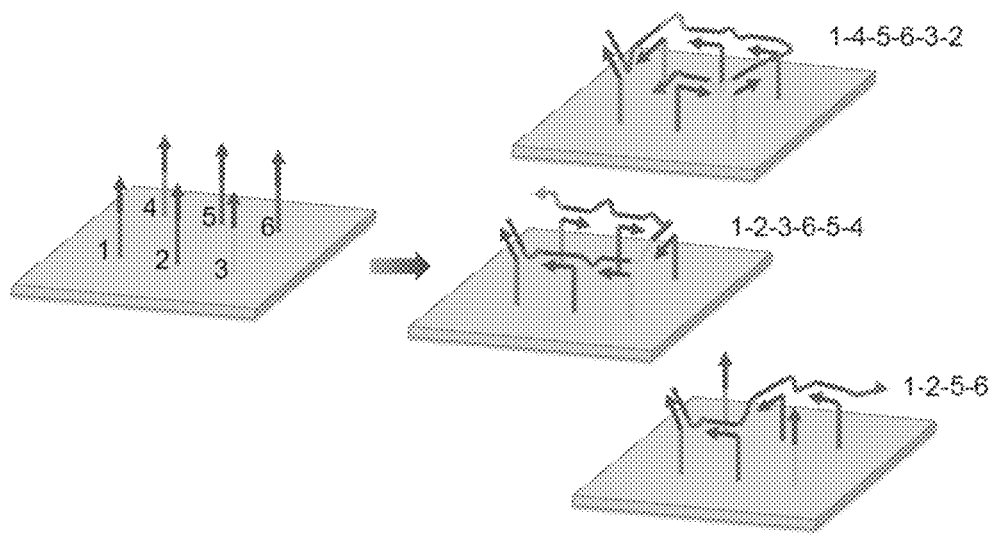

FIG. 31A shows a basic operation mechanism of the molecular crawlers. The top row depicts the unit operations on a single site. The middle row depicts one step of crawling between two neighboring sites. The bottom row depicts the initial and final states of three-site track. The generated records can be released by multiple mechanisms. Circular arrowheads at the end of some strand species indicate modifications for protection against elongation by polymerases (e.g., inverted dT). FIG. 31B shows motion of the molecular crawlers in 2D space. Probe sites anchored on the substrate are depicted as simplified single lines, with auxiliary domains omitted for clarity. The crawlers can move around the space following different paths, creating multiple kinds of records, indicated by the strings of numbers next to the products.

Figure 32A:
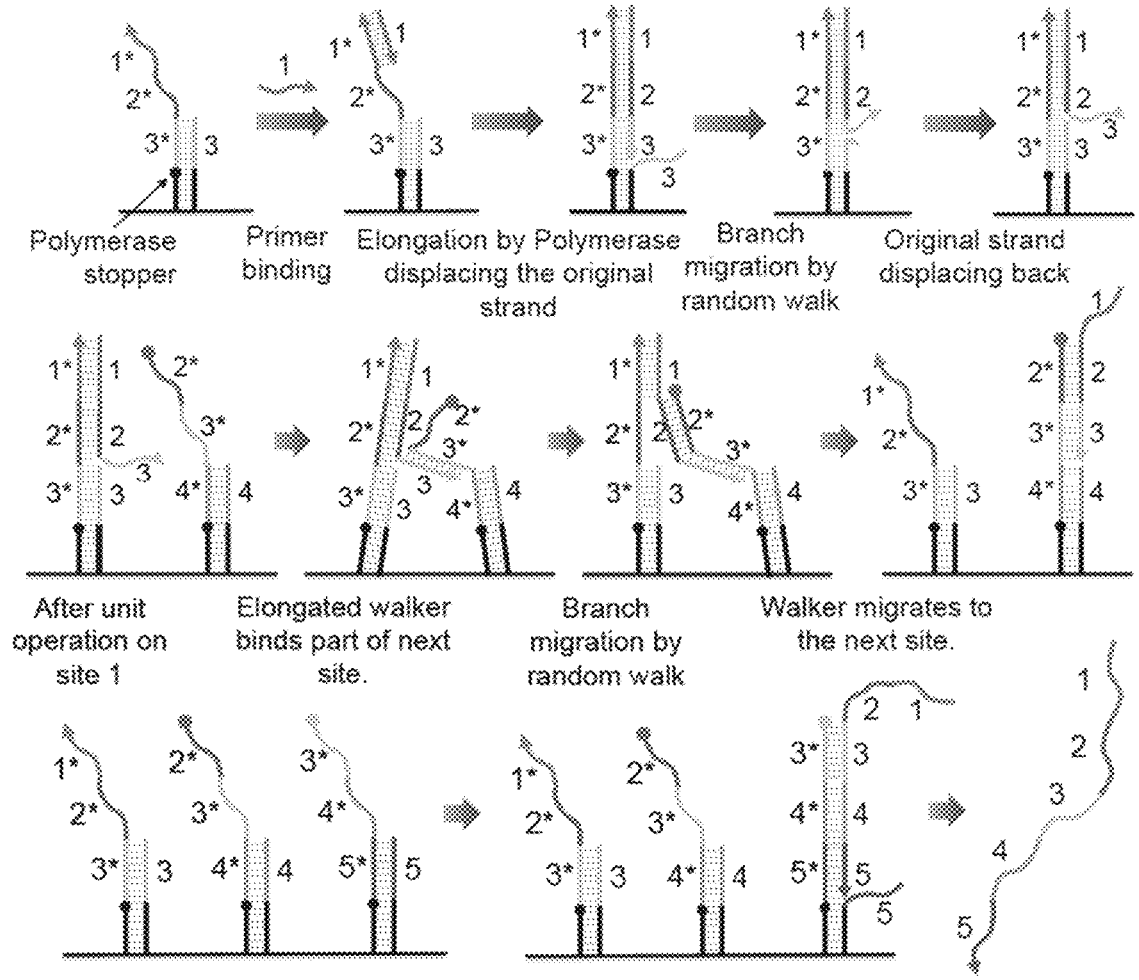
Figure 32B:
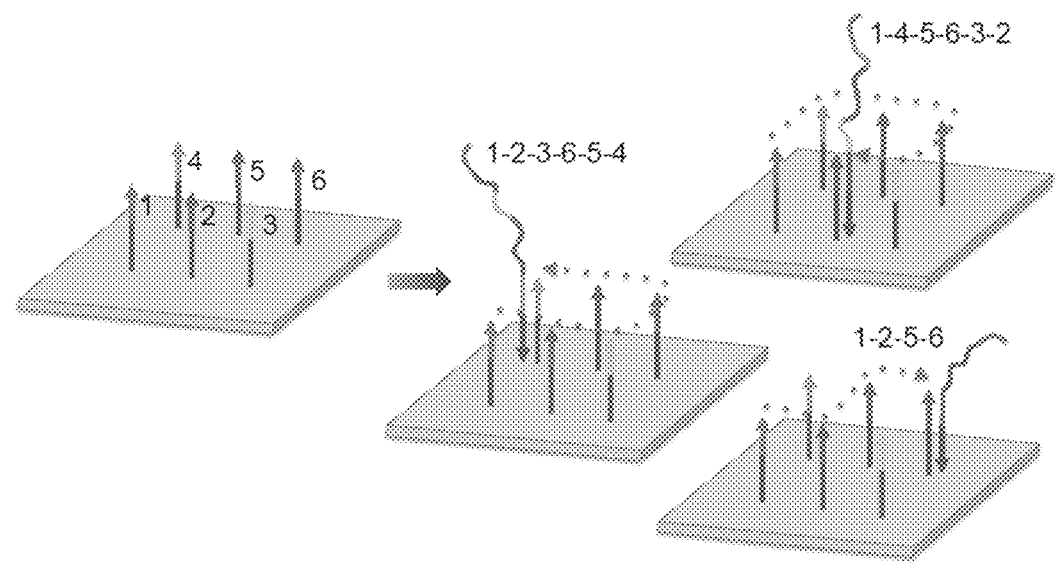

FIG. 32A shows a basic operation mechanism of the molecular walkers. The top row depicts the unit operations on a single site. The middle row depicts one step of walking between two neighboring sites. The bottom row depicts the initial and final states of three-site track. The generated records can be released by multiple mechanisms. Circular arrowheads at the end of some strand species indicate modifications for protection against elongation by polymerases (e.g., inverted dT). FIG. 32B shows motion of the molecular walkers in 2D space. Probe sites anchored on the substrate are depicted as simplified single lines, with auxiliary domains omitted for clarity. The walkers can move around the space following different paths, creating multiple kinds of records, indicated by the strings of numbers next to the products.

Figures 33A, 33B, 33C, 33D, 33E:
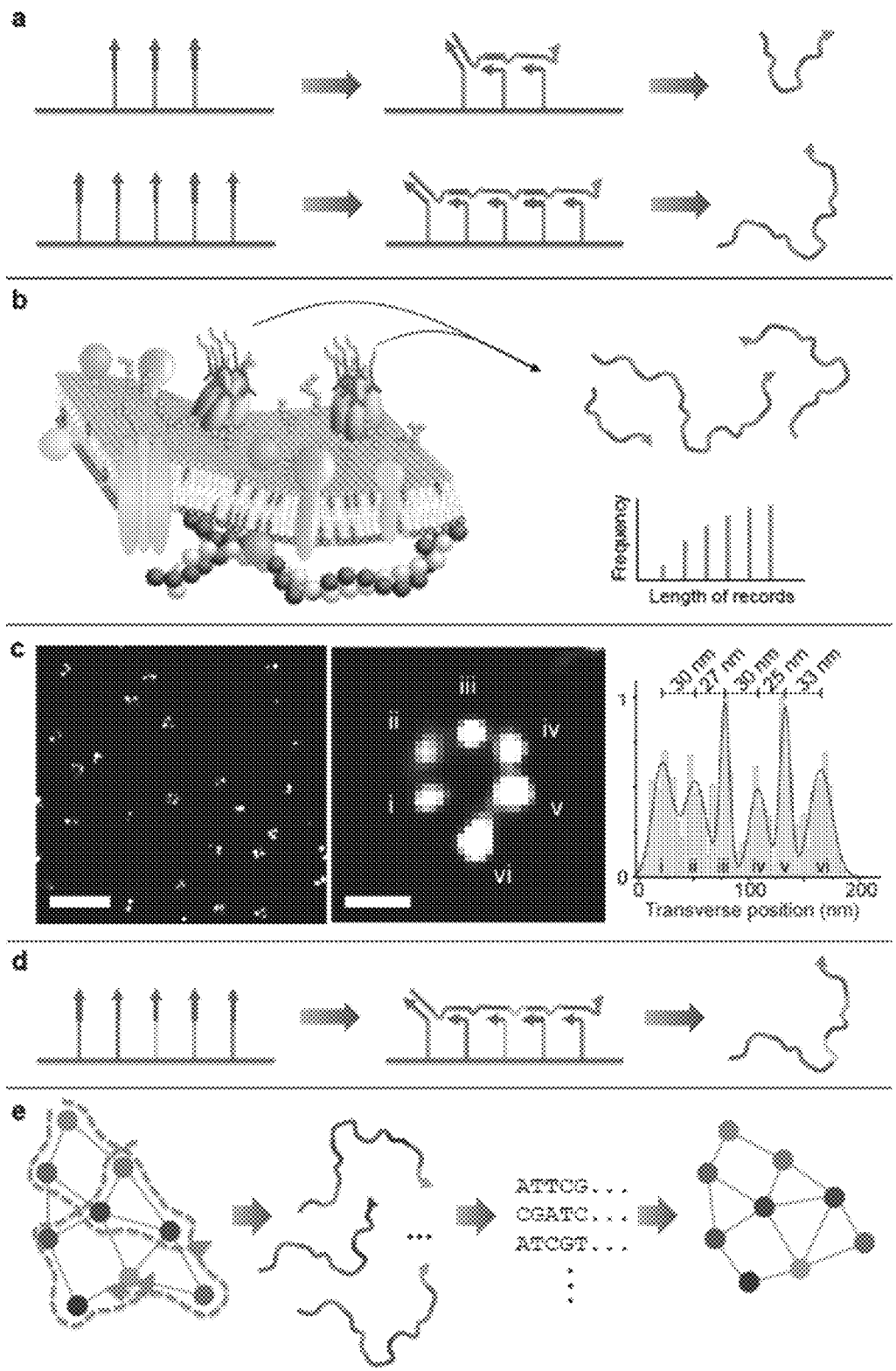

FIG. 33A shows molecular motors inspecting molecular targets and generating records reflecting the number of sites. FIG. 33B shows molecular motors being applied to biological systems to count valencies. The length distribution reflects the valency of the target. FIG. 33C shows the nuclear pore complex as a model system and the super-resolution images as reference data. The left panel shows a wide-field view and the middle panel shows a single nuclear pore complex with six subunits. The right panel shows the histogram and fit of the linearized circular intensity projection, which reveals the distance of ~30 nm between subunits. Scale bars, 300 nm (left panel), and 30 nm (middle panel). FIG. 33D shows, with unique information encoded on each site, crawlers copying, recording and reporting unique information. FIG. 33E shows several molecular motors inspecting a given molecular landscape, each following different paths, and generating unique records reflecting the spatial information. Collective analysis allows reconstruction of the molecular landscape.

Figures 34A, 34B:
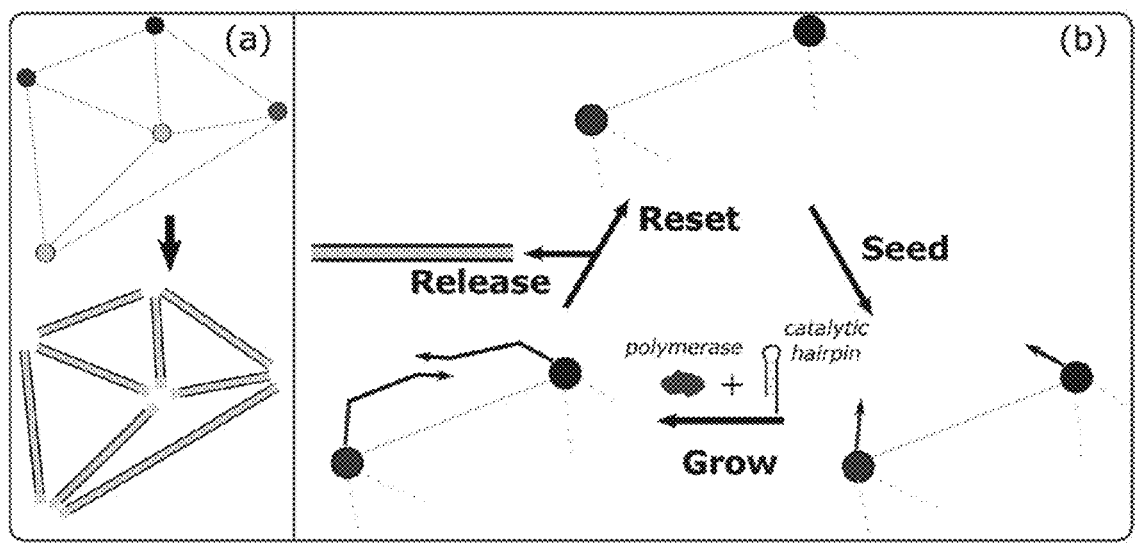

FIG. 34A shows distances recorded within DNA molecules. The shaded ends of the DNA records indicate unique barcodes for the targets. FIG. 34B shows one round of DNA record production using a molecular ruler system.

Figures 35A, 35B:
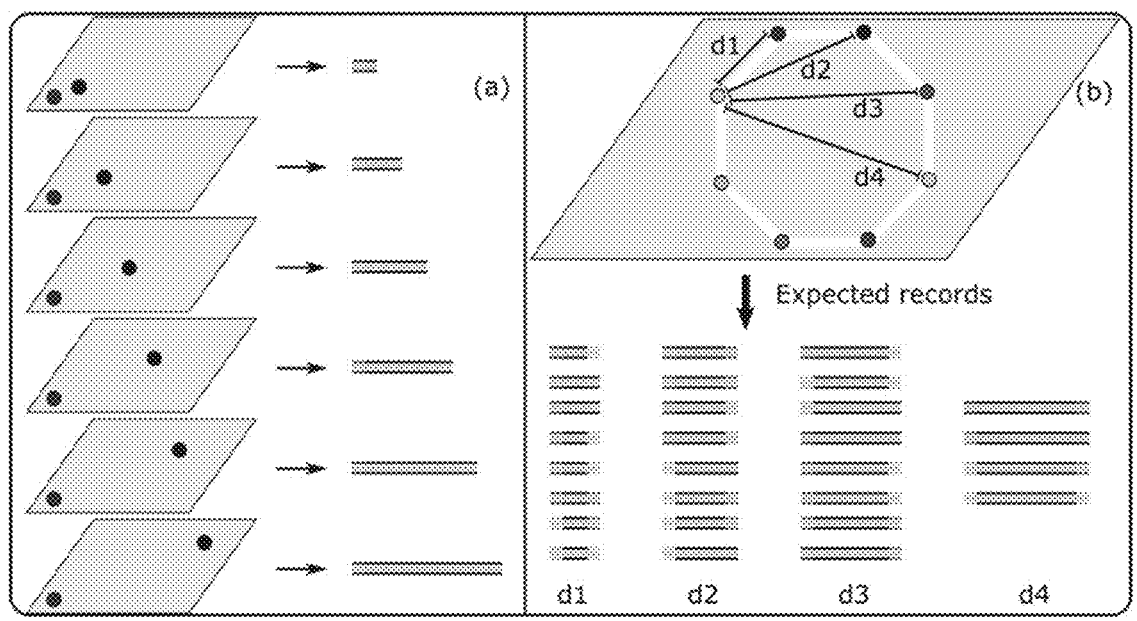

FIG. 35A shows the size of the records changing as the DNA targets are positioned.

FIG. 35B shows an NPC-mimic on a DNA nanostructure, with 28 different records produced, corresponding to one of four distances, d1; d2; d3 or d4.

FIGS. 36A-36H show a detailed mechanism for the molecular ruler system.

Figure 37A:
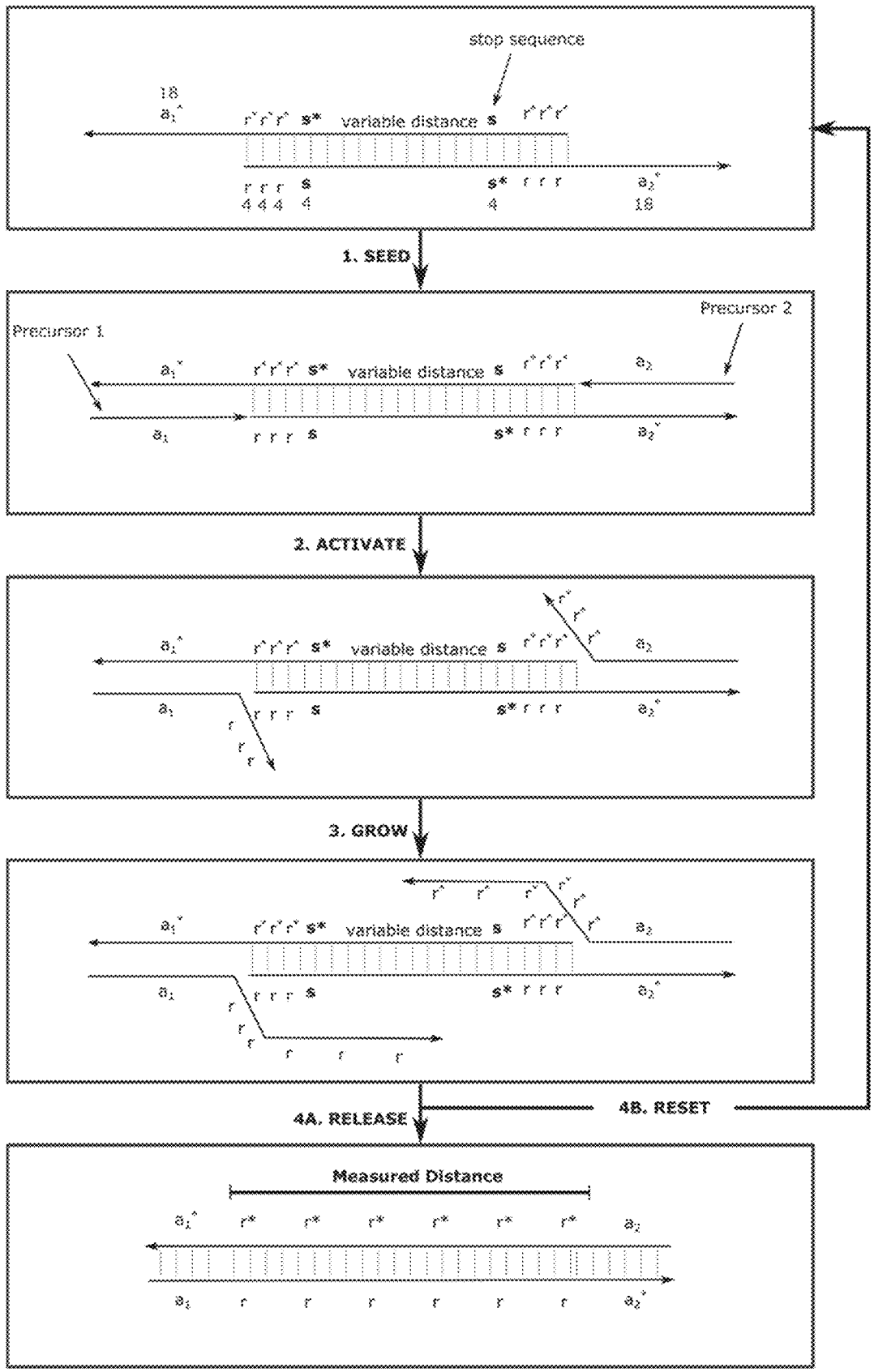
Figure 37B:
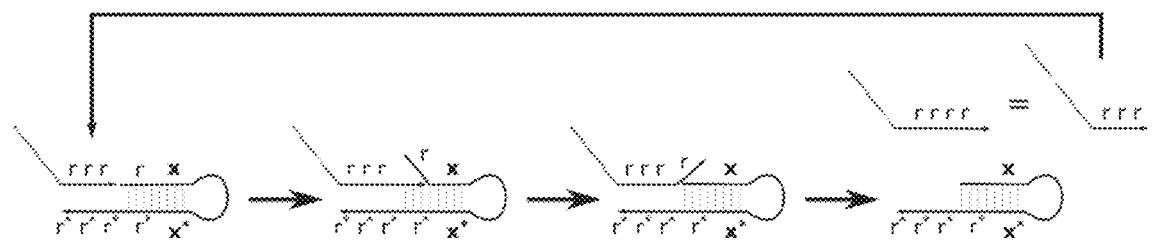
Figure 37C:
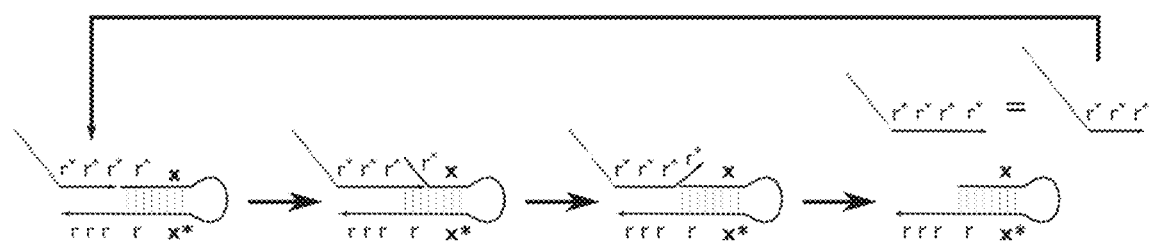

FIGS. 37A-37C show an example of a molecular ruler recording a distance between two ends of a double stranded DNA rod.

Figure 38A:
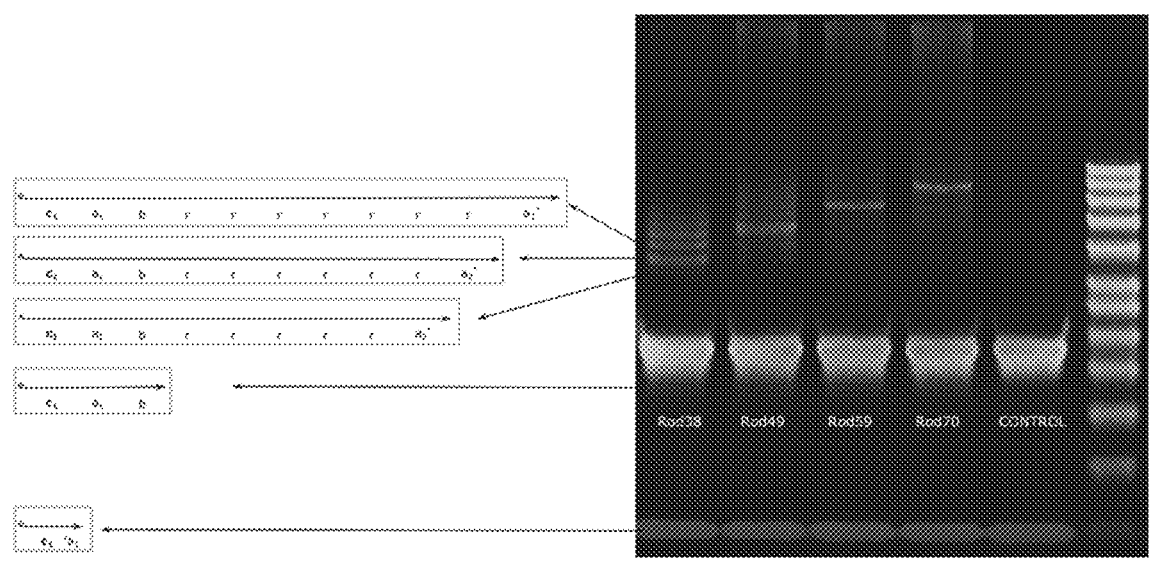
Figure 38B:
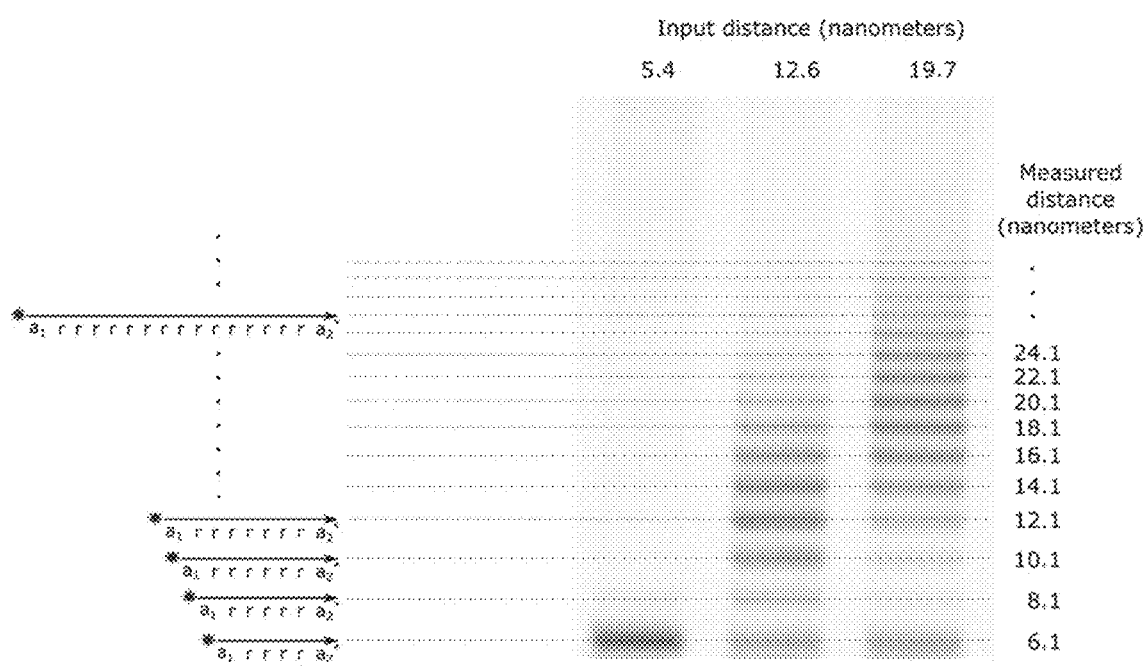

FIGS. 38A-38B show the results of molecular distance recording experiments.

Figure 39A:
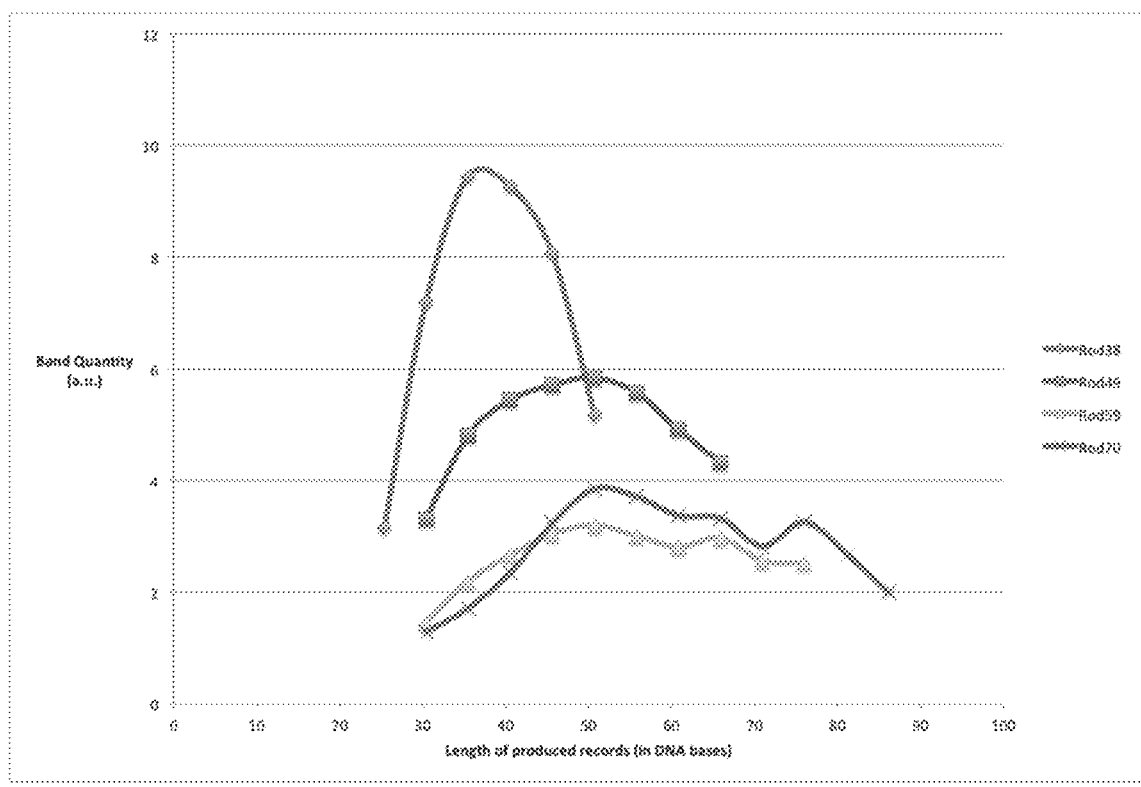
Figure 39B:
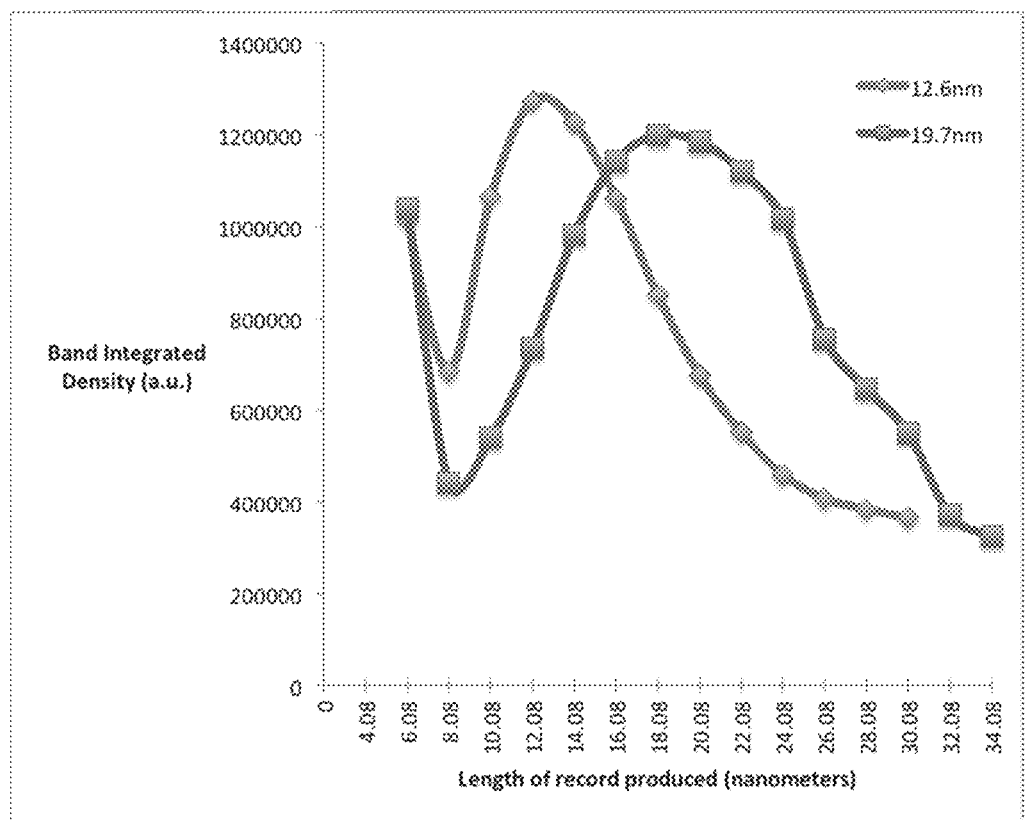

FIGS. 39A-39B show quantification of the bands from the molecular ruler distance recording experiment described in Example 21 (FIG. 38A) and plots them as function of distance (in DNA nucleotides) (FIG. 39A). Peaks correspond to the expected distance. FIG. 39B quantities the bands from the molecular ruler distance recording experiment described in FIG. 38B and plots them as function of distance (in nanometers), Peaks correspond to the expected distance. Note that the shortest distance DNA rod (5.4 nm) produces only a single record corresponding to its distance and hence is not graphed on this plot.

Figure 40:
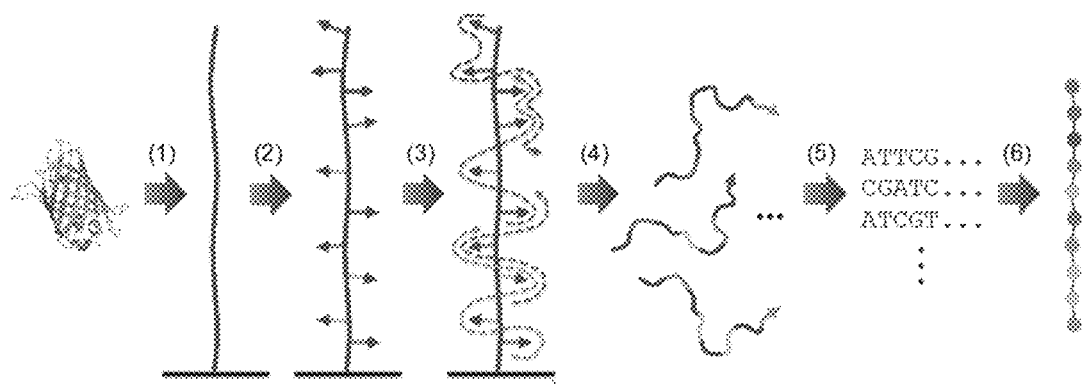

FIG. 40 shows an example of a protein "fingerprinting" method.

FIGS. 41A-41D show an example of a four-component molecular recording system.

FIGS. 42A-42D show an example of a three-component molecular recording system.

Figure 43A:
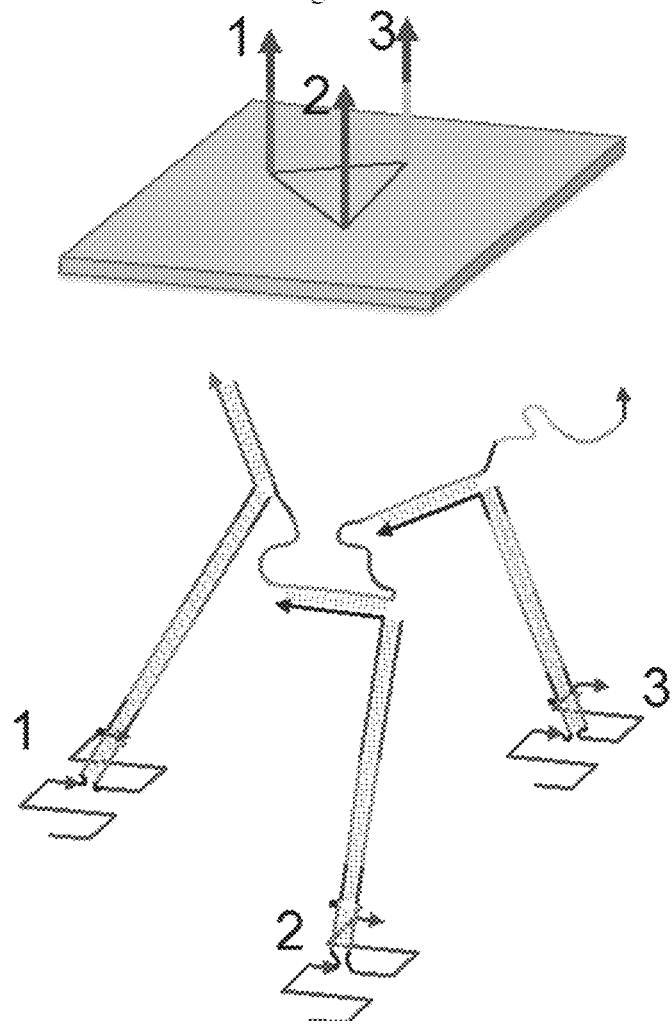
Figure 43C:
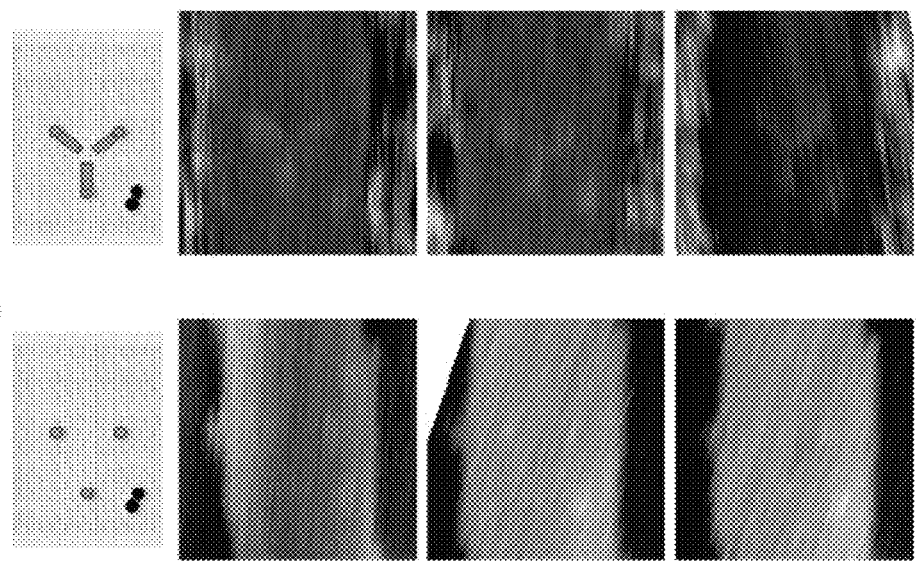
Figure 43B:
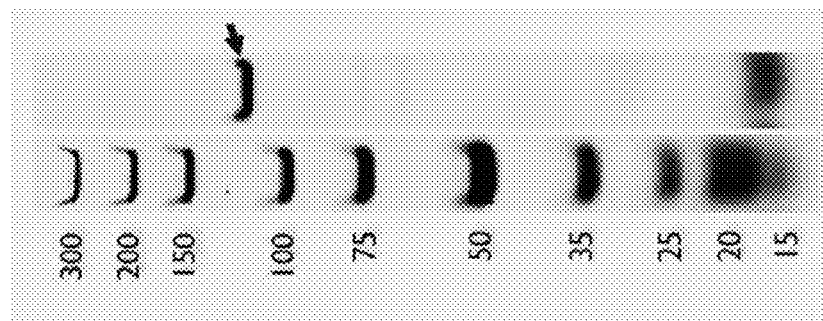

FIGS. 43A-43C show data on the motion of a molecular motor system. FIG. 43A shows a schematic of the track design tested on a DNA nanostructure platform (upper panel) and the molecular detail of the tracks after a motor has finished a recording reaction (lower panel). FIG. 43B demonstrates that, after retrieval and PCR amplification, the records generated appear at the expected length range (118 nt) under denaturing gel electrophoresis. FIG. 43C is an atomic force microscopy (AFM) visualization of the track sites and motors. Before adding motors (left panel), probe sites, colored grey, appear as dots; since each probe is anchored by two loose single-stranded loops (typically 3 Ts), the sweeping of an AFM tip captures faint images of the track positions. Two black dots are reference points. After the recording reaction (right panel), now that the track sites are connected and held together by the motor, they appear as a feature reminiscent of a tripod. The size of each origami rectangle is roughly 80 nm×100 nm.

Figure 44A:
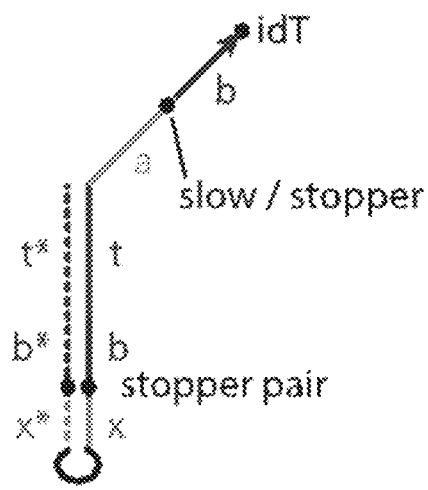
Figure 44B:
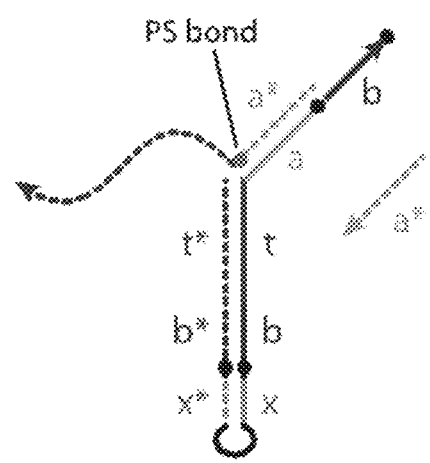
Figure 44C:
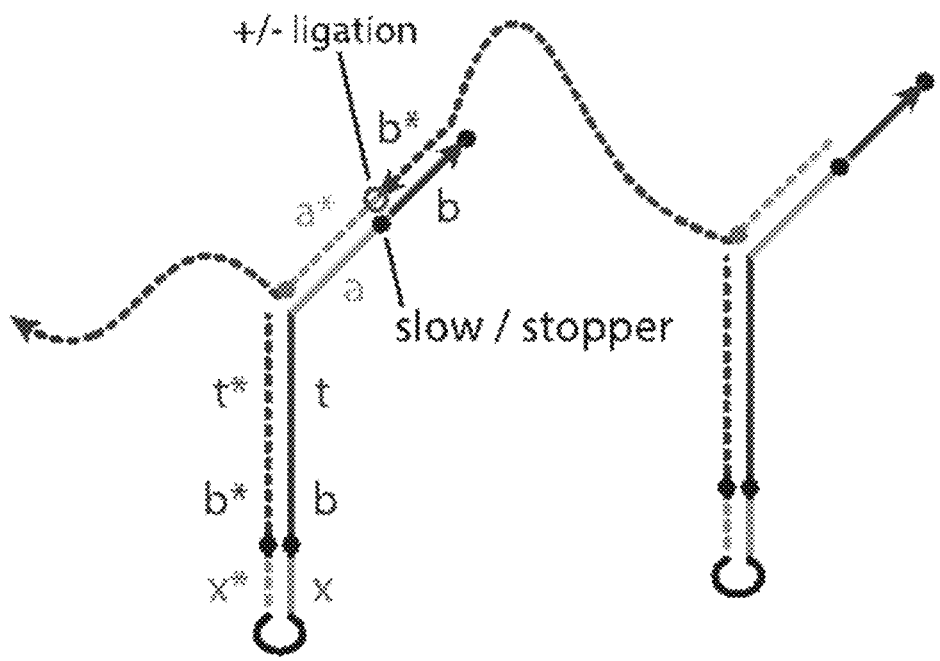
Figure 44D:
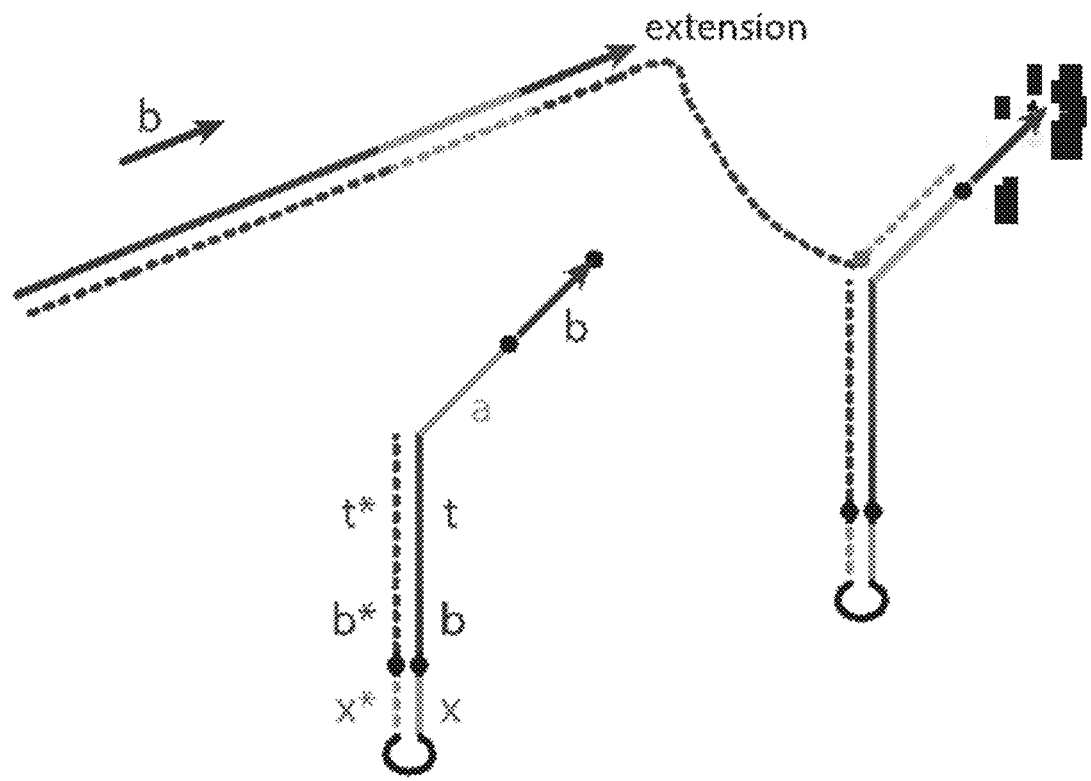
Figure 44E:
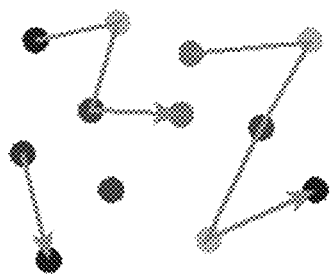

FIGS. 44A-44F show another molecular crawler mechanism. FIG. 44A depicts probes that contain two primer binding sites, domains "a" and "b." FIG. 44B shows free primers, in excess to hairpin probes, binding the probe and extending by a displacing polymerase. FIG. 44C shows several methods (methylated RNA bases on probe, a mismatch at the terminal nucleotide between "b*" and "b," an iso-dC nucleotide on the probe and a corresponding iso-dG nucleotide on the 5' end of each "a*" primer, or similar) used to slow or stop further polymerization. FIG. 44D depicts the termination of the new concatenated barcode strand by occasionally binding a low-concentration, free "b" domain strand, resulting in a polymerase copying the new concatenated strand and releasing it from all probes. Therefore, the probes are regenerated for further use. FIG. 44E shows the final result: a somewhat random patchwork of concatenated barcode copies. FIG. 44F shows example probe sequences, with domains denoted. The sequences, from top to bottom, correspond to SEQ ID NOs: 2-4.

DESCRIPTION

The tools provided herein enable the recording of molecular structure and soluble signals as well as the programmed assembly of molecular structures. For example, the present disclosure provides (a) compositions and methods for the isothermal and autonomous synthesis of single-stranded DNA that may be used to engineer the triggered assembly of complex structures in situ or as therapeutics/diagnostics in vivo. (b) molecular clocks for measuring elapsed time and timers for controlling signals after a time delay, and (c) environmentally responsive nanomachines that differentiate in response to environmental signals and record these signals over time. This disclosure provides the basis for transformative applications, such as the in situ growth of markers for Cryo-EM imaging, long term environmental surveillance of pollutants, conditional gene regulation, and the triggered encapsulation of toxins in situ, for example.

Primer Exchange Reactions

Figure 1A:
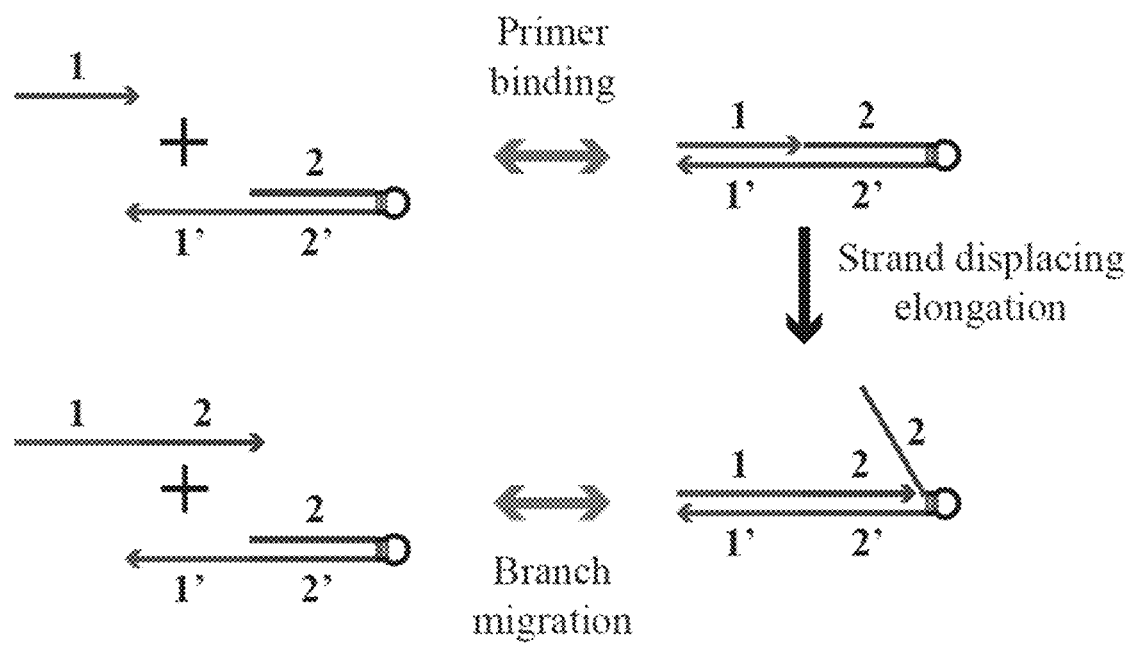
FIG. 1A shows a diagram of an example of a primer exchange reaction (PER), or a single step (cycle) of a multi-step PER. A hairpin acts catalytically to append the 2 domain onto a primer having the 1 domain.
Figure 1B:
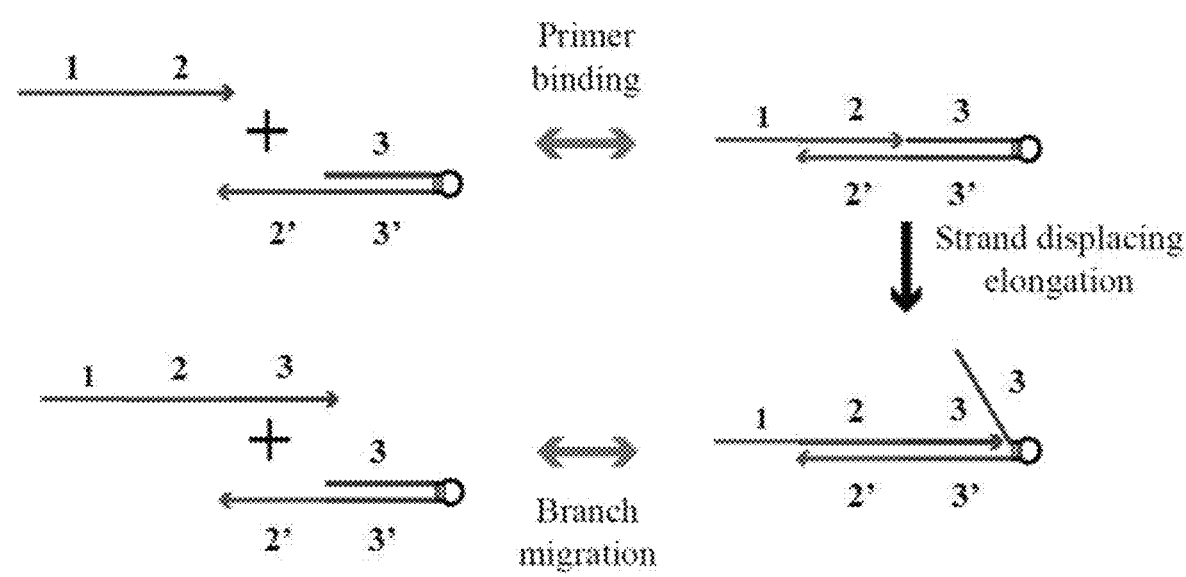
FIG. 1B also shows a PER, or a single step of a multi-step PER.

The basis of this aspect of the present disclosure is the primer exchange reaction (PER), depicted in FIGS. 1A-1B. This enzymatic method for synthesizing nucleic acids from short primer sequences operates isothermally, typically at 37° C., for example, and requires only dNTPs as fuel. Reactions can be combined to form PER cascades that grow long nucleic acid sequences, and these synthesis reactions can be made dependent on multiplexed environmental signals present. This enables spatio-temporal recording of signal information, such as presence of a specific mRNA species, into transcripts synthesized in real-time. Further, in some embodiments, because the synthesized transcripts can have arbitrary sequences, the synthesized strands themselves perform programmed functional behaviors in a cell in response to specific conditions.

The basic primer exchange reaction occurs in three general steps. First, a primer (domain 1) binds reversibly to a catalytic molecule (e.g., hairpin molecule) which facilitates elongation. Then, a strand displacement polymerase extends the primer to copy the stem sequence (domain 2') in the catalytic molecule, until a stop sequence (or other molecule that terminates polymerization) is reached. After elongation has terminated, the displaced stem region of the molecule can re-hybridize with its opposing strand on the molecule to displace the primer sequence to a point that it can spontaneously dissociate from the catalytic molecule and is free to interact with another cognate catalytic molecule in solution. This primer exchange reaction is capable of appending sequences onto growing strands in a specific, programmable manner. These modular reaction units can be combined with other such reactions to create molecular programs with specific functions. These reactions all operate isothermally and are powered by dNTPs in solution. Primer exchange reactions can easily be connected together by having the output primer sequence of one molecule (e.g., hairpin)-catalyzed reaction serve as the input primer to another one, and these reaction relationships can be represented with a state transition diagram abstraction, as shown in FIG. 2 (first column). The state of a primer is indicated by the domain on its 3' end, and each directed edge in the diagram is implemented with a single hairpin species. For example, an edge between State 1 and State 2 indicates the presence of a hairpin catalyzing the extension of a strand ending in the 1 domain with the 2 domain sequence. This abstraction describes the function of a system and can be compiled directly into hairpin and primer domains.

This model of programmability may be further defined by conditionally exposing a catalytic molecule in response to an environmental trigger, which allows for primer exchange reactions to respond dynamically to the local environment. This enables, for example, signal recording and processing applications, as discussed below.

Primer exchange reactions (PER) can easily be connected together into reaction cascades by having the output primer sequence of one hairpin-catalyzed reaction serve as the input primer to another one (FIG. 2A). FIG. 2A(i) shows the molecular components used for the synthesis of a five-domain sequence. One hairpin is used to append each domain, and the reaction process is depicted in FIG. 2A(ii). FIG. 2A(iii) shows the results of synthesis reactions performed with different subsets of the five hairpins present in solution. FIG. 2A(iv) depicts the synthesis of 40 DNA origami staple strands using 80 different catalytic hairpins and 40 primers can be performed in a one-pot reaction. When combined with the scaffold strand and annealed, these staples form DNA origami structures that can aggregate together to form long structures.

Primer exchange reaction (PER) systems, in some embodiments, power robust systems by reducing off-pathway leakage reactions by several orders of magnitude. The strand displacement polymerization cascades that power PER systems dynamically synthesize new information, and the activation energy is high for initiating a leakage polymerization reaction. These low leakage systems can be used, in some embodiments, to build robust and scalable molecular systems. Further, the PER systems provided herein are capable of having the set of nucleic acid strands in solution climb the free energy landscape, allowing for a large space of programmable behavior and the achievability of operations that is thermodynamically impossible in enzyme (e.g., polymerase) free systems. Energy is introduced into the system through polymerization reactions, so PER systems are continuously being powered by inexpensive dNTPs as fuel. In some embodiments, the dNTP concentration is sufficient for the primer exchange system to operate for long periods of time, and modulating concentration or replenishing dNTPs further extends this operating time. Further still, PER systems synthesize strands in situ. Primers localized inside fixed cells, for example, can be polymerized directly in place, thus overcoming the challenge of delivering a large oligonucleotide into a crowded cellular environment. This capability opens up a broad application space, with many possibilities for assembling (growing) large structures in situ. Even further still, PER systems, in some embodiments, have single molecule resolution, automatically growing one transcript per primer molecule in solution. Each transcript indicates the ordered set of states (history) it traversed in the state transition diagram graph over time, with course length information that can be read out on gels and more precise information that can be obtained with sequencing. These transcripts can be engineered, for example, to record transcripts of when environmental signals were present in solution over time.

In some embodiments, individual PER synthesis reactions can be programmed to be conditionally active (FIGS. 23A-23D and FIGS. 26A-26D), enabling a large and diverse set of possible programmable behavior, as well as opportunities for recording environmental signals in situ. FIGS. 23A-23D show how an oncogenic miRNA target, miR-19a, can trigger the synthesis of a DNAzyme, DZ-TWT, that has been shown to promote apoptosis in mouse cells[2]. DNAzyme behavior is validated by visualizing the cleavage of a fragment of the DZ-TWT target, TWT (FIG. 23E). FIGS. 26A-26D shows how primer exchange reactions can be used to record the order in which the same two targets, miR-19a and TWT, are encountered in solution.

Overall, the primer exchange reactions provided herein represent a new paradigm for molecular programming, with their catalytic activity, modularity, robustness, basic fuel species (dNTPs), in situ operation, and single-molecule transcript recording.

Primer Exchange Compositions and Systems

A catalytic nucleic acid molecule ("catalytic molecule") generally includes an unpaired (single-stranded) 3' toehold domain and a paired (double-stranded) domain S from (and, in some embodiments, directly adjacent to) the 3' toehold domain. "Catalytic hairpin molecules" also include a loop domain. The kinetics of primer exchange reactions can be controlled by modifying the length, composition and concentration of the catalytic molecules (e.g., one or more domains of the catalytic molecules), for example.

A catalytic hairpin (see FIG. 1A as an illustrative example) includes a 3' toehold domain ("1'") linked to a hairpin stem domain (e.g., formed by intramolecular binding of subdomain "2" to subdomain "2'") linked to a hairpin loop domain (loop-like structure). An example of a catalytic molecule without a loop domain is shown in FIG. 24 ("duplex"). The length of a catalytic molecule (e.g., catalytic hairpin molecule) may vary. In some embodiments, a catalytic molecule has a length of 25-300 nucleotides. For example, a catalytic molecule may have a length of 25-250, 25-200, 25-150, 25-100, 25-50, 50-300, 50-250, 50-200, 50-150 or 50-100 nucleotides. In some embodiments, a catalytic molecule has a length of 30-50, 40-60, 50-70, 60-80, 70-90, 80-100, 100-125, 100-150 or 100-200 nucleotides. In some embodiments, a catalytic molecule has a length of 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 nucleotides. A catalytic molecule, in some embodiments, is longer than 300 nucleotides, or shorter than 25 nucleotides.

A "toehold domain" refers to an unpaired sequence of nucleotides located at the 3' end of the catalytic molecule and is complementary to (and binds to) a nucleotide sequence of a primer (or primer domain of a primer). The length of a toehold domain may vary. In some embodiments, a toehold domain has a length of 5-40 nucleotides. For example, a toehold domain may have a length of 2-35, 2-30, 2-25, 2-20, 2-15, 2-10, 5-35, 5-30, 5-25, 5-20, 5-15, 5-10, 10-40, 10-35, 10-30, 10-25, 10-20, 10-15, 15-40, 15-35, 15-30, 15-25, 15-20, 20-40, 20-35, 20-30, 20-25, 25-40, 25-35, 25-30, 30-40, 30-35 or 35-40 nucleotides. In some embodiments, a toehold domain has a length of 5, 10, 15, 20, 25, 30, 35 or 40 nucleotides. In some embodiments, a toehold domain has a length of 10, 11, 12, 13, 14, 15, 16, 17, 18, 19, 20, 21, 22, 23, 24 or 25 nucleotides. A toehold domain, in some embodiments, is longer than 40 nucleotides, or shorter than 5 nucleotides.

An initial primer (or a primer domain) binds to a 3' unpaired (single-stranded) toehold domain of a catalytic molecule to initial the primer exchange reaction. In this reaction (see FIG. 1A as an illustrative example), the initial input primer ("1") binds to the toehold domain of a catalytic molecule ("1"'), and extension of the primer by a strand displacement polymerase present in the reaction solution displaces one of the subdomains ("2") of the stem domain of the catalytic molecule through a branch migration process. The overall effect is that one of the subdomains ("2") of the hairpin stem domain is replaced with the extended (newly synthesized) primer domain.

A "paired domain" or a "stem domain" of a catalytic molecule refers to a paired sequence of nucleotides (e.g., Watson-Crick nucleobase pairing) located 5' from (and, in some embodiments, directly adjacent to) the unpaired toehold domain of a catalytic molecule. The paired domain of a catalytic molecule us formed by nucleotide base pairing between a displacement strand and a template strand containing a toehold domain. The paired stem domain of a catalytic hairpin molecule is formed by intramolecular base pairing (base pairing between nucleotides within the same molecule) of two subdomains of a catalytic hairpin molecule: e.g., an internal/central subdomain located 5' from the toehold domain bound (hybridized) to a subdomain located at the 5' end of the catalytic hairpin. The length of a paired domain may vary. In some embodiments, a paired domain has a length of 5-40 nucleotides. For example, a paired domain may have a length of 5-35, 5-30, 5-25, 5-20, 5-15, 5-10, 10-40, 10-35, 10-30, 10-25, 10-20, 10-15, 15-40, 15-35, 15-30, 15-25, 15-20, 20-40, 20-35, 20-30, 20-25, 25-40, 25-35, 25-30, 30-40, 30-35 or 35-40 nucleotides. In some embodiments, a paired domain has a length of 5, 10, 15, 20, 25, 30, 35 or 40 nucleotides. In some embodiments, a paired domain has a length of 10, 11, 12, 13, 14, 15, 16, 17, 18, 19, 20, 21, 22, 23, 24 or 25 nucleotides. A paired domain, in some embodiments, is longer than 40 nucleotides, or shorter than 5 nucleotides.

While a paired domain is generally formed by intramolecular base pairing of two subdomains of a catalytic molecule, it should be understood that this paired domain may contain at least one mismatch pair (e.g., pairing of A with C or G, or pairing of T with C or G). In some embodiments, the stem domain has 1-5 mismatch nucleotide base pairs. For example, a paired domain may be have 1, 2, 3, 4 or 5 mismatch nucleotide base pairs.

In some embodiments, extension of a primer (bound to a primer-binding site) by a displacing polymerase is terminated by the presence of a molecule or modification in the catalytic molecule that terminates polymerization. Thus, in some embodiments, catalytic molecules of the present disclosure comprise a molecule or modification that terminates polymerization. A molecule or modification that terminates polymerization ("stopper") is typically located in a paired domain (e.g., stem domain) of a catalytic molecule such that polymerization terminates extension of the primer through the paired domain. For catalytic molecules arranged in the form of a hairpin, a molecule or modification that terminates polymerization may be located between the paired stem domain and the loop domain. In some embodiments, the molecule that terminate polymerization is a synthetic non-DNA linker, for example, a triethylene glycol spacer, such as the Int Spacer 9 (iSp9) or Spacer 18 (integrated DNA Technologies (IDT)). It should be understood that any non-native linker that terminates polymerization by a polymerase may be used as provided herein. Other non-limiting examples of such molecules and modifications include a three-carbon linkage (/iSpC3/) (IDT), ACRYDITE™ (IDT), adenylation, azide, digoxigenin (NHS ester), cholesteryl-TEG (IDT), I-LINKER™ (IDT), and 3-cyanovinylcarbazole (CNVK) and variants thereof. Typically, but not always, short linkers (e.g., iSp9) lead to faster reaction times.

In some embodiments, the molecule that terminates polymerization is a single or paired non-natural nucleotide sequence, such as iso-dG and iso-dC (IDT), which are chemical variants of cytosine and guanine, respectively. Iso-dC will base pair (hydrogen bond) with Iso-dG but not with dG. Similarly, Iso-dG will base pair with Iso-dC but not with dC. By incorporating these nucleotides in a pair on opposite sides of the hairpin, at the stopper position, the polymerase will be halted, as it does not have a complementary nucleotide in solution to add at that position.

In some embodiments, the efficiency of performance of a "stopper" modification is improved by lowering dNTP concentrations (e.g., from 200 µM) in a reaction to 100 µM, 10 µM, 1 µM, or less.

Inclusion of a molecule or modification that terminates polymerization often creates a "bulge" in a double-stranded domain of catalytic molecule (e.g., a stem domain for hairpin structures), because the molecule or modification is not paired. Thus, in some embodiments, catalytic molecules are designed to include, opposite the molecule or modification, a single nucleotide (e.g., thymine), at least two of same nucleotide (e.g., a thymine dimer (TT) or trimer (TTT)), or an non-natural modification.

A "loop domain" of a catalytic hairpin refers to a primarily unpaired sequence of nucleotides that form a loop-like structure at the end (adjacent to) of the stem domain. The length of a loop domain may vary. In some embodiments, an loop domain has a length 3-200 nucleotides. For example, a loop domain may have a length of 3-175, 3-150, 3-125, 3-100, 3-75, 3-50, 3-25, 4-175, 4-150, 4-125, 4-100, 4-75, 4-50, 4-25, 5-175, 5-150, 5-125, 5-100, 5-75, 5-50 or 5-25 nucleotides. In some embodiments, a loop domain has a length of 3-10, 3-15, 32-10, 3-25, 3-30, 3-35, 3-40, 3-35, 3-40, 3-45, 3-50, 4-10, 4-15, 4-10, 4-25, 4-30, 4-35, 4-40, 4-35, 4-40, 4-45 or 4-50 nucleotides. In some embodiments, a loop domain has a length of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 45, 46, 47, 48, 49 or 50 nucleotides. A loop domain, in some embodiments, is longer than 300 nucleotides.

In some embodiments, a catalytic molecule does not contain a hairpin loop domain. For example, a catalytic molecule may simply be a duplex comprising a 3' unpaired toehold domain adjacent to a paired domain (see, e.g., FIG. 24 "duplex"), similar to a stem domain (without the adjacent loop domain). Catalytic molecules that do not include a loop domain may be stabilized at the end opposite the 3' toehold domain through crosslinking or nucleotide base complementarity between a stretch (e.g., 10 or more) nucleotide base pairs.

Primer exchange reaction systems, in additional to catalytic hairpins, include primers, referred to as input primers or output primers. A "primer" is a nucleic acid that, when bound to another nucleic acid, is the starting point for polymerization in the presence of a polymerase. As used herein, a primer is typically a nucleic acid (e.g., single-stranded nucleic acid) have a nucleotide sequence (domain) complementary to a toehold domain of a catalytic molecule (see, e.g., molecule "1" of FIG. 1A, top left: see also molecule "1+2" of FIG. 1B, top left). An "input primer" is a primer that binds to a catalytic molecule to initiate a primer exchange reaction. An "output primer" is the extension product released from the catalytic molecule at the end of each step of a primer exchange reaction. An output primer, following dissociation from a catalytic molecule, may then serve as an input primer in another (subsequent) step of a primer exchange reaction.

A complete "step" of a primer exchange reaction is depicted in FIG. 1A. An input primer ("1") binds to a toehold domain ("1'") of a catalytic molecule to start the primer exchange reaction. Upon binding to the catalytic molecule in reaction solution containing polymerase (e.g., strand displacing polymerase) and dNTPs, the initial primer is extended through the paired domain, displacing a subdomain ("2") of the paired domain. The displaced subdomain ("2") then competes with the extended primer ("1+2") for binding (reannealing) with its complementary subdomain ("2'"), thereby displacing the extended output primer "1+2". This completes a step of the primer exchange reaction. The displaced output primer "1+2" may then go on to function as an input primer in the next step of the reaction.

For example, as shown in FIG. 1B, the displaced output primer "1+2," in another step of a primer exchange reaction, serves as an input primer, binding through its primer domain "2" to the toehold domain "2'" of another catalytic molecule, thereby initiating another step in the primer exchange reaction. Upon binding to the catalytic molecule in reaction solution containing polymerase and dNTPs, input primer "1+2" is extended through the paired domain, displacing a subdomain ("3") of the paired domain. The displaced subdomain ("3") then competes with the extended primer ("1+2+3") for binding (reannealing) with its complementary subdomain ("3'"), thereby displacing the extended output primer "1+2+3". This completes another step of the primer exchange reaction. The displaced output primer "1+2+3" may then go on to function as an input primer in the next step of the reaction.

In some embodiments, a primer or primer domain (the nucleotide sequence that binds to the toehold domain of a catalytic molecule) has a length of 10-50 nucleotides. For example, a primer or primer domain may have a length of 10-45, 10-40, 10-35, 10-30, 10-25, 10-20, 10-15, 15-50, 15-45, 15-40, 15-35, 15-30, 15-25, 15-20, 20-50, 20-45, 20-40, 20-35, 20-30, 20-25, 25-50, 25-45, 25-40, 25-35, 25-30, 30-50, 30-45, 30-40, 30-35, 35-50, 35-45, 35-40, 40-50, 40-45 or 45-50 nucleotides. In some embodiments, a primer or primer domain has a length of 10, 15, 20, 25, 30, 35, 40, 45 or 50 nucleotides. In some embodiments, a primer or primer domain has a length of 15, 16, 17, 18, 19, 20, 21, 22, 23, 24 or 25 nucleotides. A primer or primer domain, in some embodiments, is longer than 50 nucleotides, or shorter than 10 nucleotides. It should be understood that the full length of a primer depends, at least in part, on the number and length of appended (polymerized) sequences, which depends on the number and length of catalytic molecules present in a reaction.

A primer, as provided herein, may be linked to (labeled with) a detectable molecule (e.g., a molecule that emits a detectable signal, such as a fluorescent or chemiluminescent signal). In some embodiments, the label is a fluorophore. A primer linked to a fluorophore or other fluorescent/chemiluminescent molecule is referred to simply as a "fluorescent primer." Examples of fluorophores that may be used herein include, without limitation, hydroxycoumarin, methoxycoumarin, Alexa fluor, aminocoumarin, Cy2, FAM, Alexa fluor 405, Alexa fluor 488, Fluorescein FITC, Alexa fluor 430, Alexa fluor 532, HEX, Cy3, TRITC, Alexa fluor 546, Alexa fluor 555, R-phycoerythrin (PE), Rhodamine Red-X, Tamara, Cy3.5 581, Rox, Alexa fluor 568, Red 613, Texas Red, Alexa fluor 594, Alexa fluor 633, Allophycocyanin, Alexa fluor 647, Cy5, Alexa fluor 660. Cy5.5, TruRed, Alexa fluor 680, Cy7 and Cy7.5. Other fluorophores and molecules that emit a detectable signal are encompassed by the present disclosure.

In some embodiments, a detectable molecule is linked to a catalytic molecule rather than the primer.

Figures 27A, 27B, 27C, 27D, 27E:
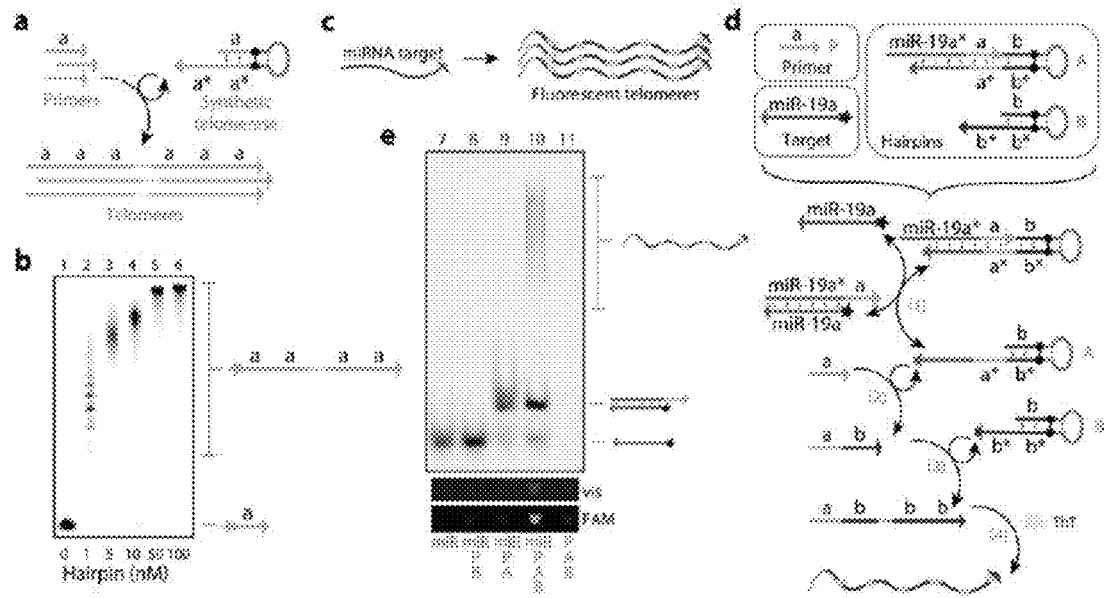

In some embodiments, a detectable molecule is incorporated into a growing nucleic acid strand, as shown, for example, in FIG. 27D. Thus, in some embodiments, a detectable molecule is Thioflavin (ThT), which intercalates into concatenate repeats of the human telomeric sequence TTAGGG. Other intercalating detectable molecule are encompassed herein.

In some embodiments, a primer is linked to a biomolecule. Biomolecules include, for example, nucleic acids (e.g., DNA or RNA) and proteins. A biomolecule may be a therapeutic, prophylactic, diagnostic or imaging molecule. In some embodiments, a biomolecule is a disease-related or drug-related biomolecule, such as a cancer-related gene or protein, or an FDA-approved or potential drug target. In some embodiments, a biomolecule is an enzyme, an antigen, a receptor, a ligand, a membrane protein, a secreted protein, or a transcription factor.

In some embodiments, a catalytic molecule is linked to a biomolecule.

Primer exchange reactions require the use of a polymerase. In some embodiments, the polymerase is a DNA polymerase (DNAP), such as a DNA polymerase having DNA strand displacement activity (a strand displacement polymerase). "Strand displacement" describes the ability to displace downstream DNA encountered during synthesis. Examples of polymerases having DNA strand displacement activity that may be used as provided herein include, without limitation, phi29 DNA polymerase (e.g., NEB #M0269), Bst DNA polymerase, large fragment (e.g., NEB #M0275), or Bsu DNA polymerase, large fragment (e.g., NEB #M0330). Other polymerases having strand displacement activity may be used. In some embodiments, the polymerase is a RNA polymerase.

In some embodiments, the polymerase is phi29 DNA polymerase. In such embodiments, the reaction conditions may be as follows: 1× reaction buffer (e.g., 50 mM Tris-HCl, 10 mM MgCl$_2$, 10 mM (NH$_4$)$_2$SO$_4$, 4 mM DTT) supplement with purified bovine serum albumin (BSA), pH 7.5, incubated at 30° C.

In some embodiments, the polymerase is Bst DNA polymerase, large fragment. In such embodiments, the reaction conditions may be as follows: 1× reaction buffer (e.g., 20 mM Tris-HCl, 10 mM (NH$_4$)$_2$SO$_4$, 10 mM KCl, 2 mM MgSO$_4$, 0.1% TRITON® X-100). pH 8.8, incubated at 65° C.

In some embodiments, the polymerase is Bsu DNA polymerase. In such embodiments, the reaction conditions may be as follows: IX reaction buffer (e.g., 50 mM NaCl, 10 mM Tris-HCl, 10 mM MgCl$_2$, 1 mM DTT), pH 7.9, incubated at 37° C.

The concentration of primer, catalytic molecules and dNTPs in a primer exchange reaction system may be varied depending, for example, on the particular application and kinetics required for that particular application.

The concentration of primer in a primer exchange reaction may be, for example, 10 nM to 1000 nM. In some embodiments, the primer concentration in a primer exchange reaction is 10-20, 10-30, 10-40, 10-50, 10-60, 10-70, 10-80, 10-90, 10-100, 10-125, 10-150, 10-200, 25-50, 25-75, 25-100, 25-150, 25-200, 50-75, 50-100, 50-150 or 50-200 nM. In some embodiments, the primer concentration in a primer exchange reaction is 100-200, 100-300, 100-400, 100-500, 100-600, 100-70, 100-800, 100-900 or 100-1000 nM. In some embodiments, the primer concentration in a primer exchange reaction is 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195 or 200 nM. In some embodiments, the primer concentration in a primer exchange reaction is 100, 200, 300, 400, 500, 600, 700, 800, 900 or 1000 nM. The concentration of primer in a primer exchange reaction may be less than 10 nM or greater than 1000 nM.

The concentration of catalytic molecules (e.g., catalytic hairpins) in a primer exchange reaction may be, for example, 5 nM to 1000 nM. In some embodiments, the catalytic molecule concentration in a primer exchange reaction is 5-10, 5-20, 5-30, 5-40, 5-50, 5-60, 5-70, 5-80, 5-90, 5-100, 5-125, 5-150, 5-200, 10-50, 10-75, 10-100, 10-150, 10-200, 25-75, 25-100, 25-125 or 25-200 nM. In some embodiments, the catalytic molecule concentration in a primer exchange reaction is 10-200, 10-300, 10-400, 10-500, 10-600, 10-70, 10-800, 10-900 or 10-100 nM. In some embodiments, the catalytic molecule concentration in a primer exchange reaction is 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195 or 200 nM. In some embodiments, the catalytic molecule concentration in a primer exchange reaction is 10, 20, 30, 40, 50, 60, 70, 80, 90 or 100 nM. The concentration of catalytic molecule in a primer exchange reaction may be less than 5 nM or greater than 1000 nM.

The ratio of primer to catalytic molecule in primer exchange reaction may be 2:1 to 100:1. In some embodiments, the ratio of primer to catalytic molecule is 2:1, 3:1, 4:1, 5:1, 6:1, :1, 8:1, 9:1, 10:1, 11:1, 12:1, 13:1, 14:1, 15:1, 16:1, 17:1, 18:1, 19:1 or 20:1. In some embodiments, the ratio of primer to catalytic molecule is 30:1, 40:1, 50:1, 60:1, 70:1, 80:1 or 90:1.

The number of different catalytic molecules in a primer exchange reaction in non-limiting. A primer exchange reaction may comprise 1-10$^{10}$ different catalytic molecules (each with a specific toehold domain sequence, for example). In some embodiments, a primer exchange reaction comprises 1-10, 1-10$^2$, 1-10$^3$, 1-10$^4$, 1-10, 1-10$^1$, 1-10$^7$, 1-10$^8$, 1-10, 1-10$^{10}$, or more, different catalytic molecules. In some embodiments, a primer exchange reaction comprises 1-5, 1-10, 1-15, 1-20, 1-25, 1-30, 1-35, 1-40, 1-45, 1-50, 1-55, 1-60, 1-65, 1-70, 1-75, 1-80, 1-85, 1-90, 1-95, 1-100, 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 10-15, 10-20, 10-25, 10-30, 10-35, 10-40, 10-45, 10-50, 10-55, 10-60, 10-65, 10-70, 10-75, 10-80, 10-85, 10-90, 10-95 or 10-100 different catalytic molecules. In some embodiments, a primer exchange reaction comprises 1, 2, 3, 4, 5, 6, 7, 8, 9, 10, 11, 12, 13, 14, 15, 16, 17, 28, 19, 20, 21, 22, 23, 24 or 25 different catalytic molecules. Catalytic molecules are different from each other if their toehold domains differ from each other, for example.

The kinetics of a primer exchange reaction may be controlled by varying temperature, time, buffer/salt conditions, and deoxyribonucleotide triphosphate (dNTP) concentrations, for example. Polymerases, like most enzymes, are sensitive to many buffer conditions, including ionic strength, pH and types of metal ions present (e.g., sodium ions vs. magnesium ions). Thus, the temperature at which a primer exchange reaction is performed may vary from, for example, 4° C. to 65° C. (e.g., 4° C., 25° C., 37° C., 42° C. or 65° C.). In some embodiments, the temperature at which a primer exchange reaction is performed is 4-25° C., 4-30° C., 4-35° C., 4-40° C., 4-45° C., 4-50° C., 4-55° C., 4-60° C., 10-25° C., 10-30° C. 10-35° C., 10-40° C., 10-45° C., 10-50° C., 10-55° C., 10-60° C., 25-30° C., 25-35° C., 25-40° C., 25-45° C., 25-50° C., 25-55° C., 25-60° C., 25-65° C., 35-40° C., 35-45° C., 35-50° C., 35-55° C., 35-60° C., or 35-65° C. In some embodiments, a primer exchange reaction is performed at mom temperature, while in other embodiments, a primer exchange reaction is performed at 37° C.

A primer exchange reaction may be performed (incubated) for 30 minutes (min) to 24 hours (hr). In some embodiments, a primer exchange reaction is carried out for 10 min, 35 min, 40 min, 45 min, 50 min, 55 min, 60 min, 1 hr, 2 hr, 3 hr, 4 hr, 5 hr, 6 hr, 7 hr, 8 hr, 9 hr, 10 hr, 11 hr, 12 hr, 18 hr or 24 hr.

Deoxyribonucleotides (dNTPs) are the "fuel" that drives a primer exchange reaction. Thus, the kinetics of a primer exchange reaction, in some embodiments, depends heavily on the concentration of dNTPs in a reaction. The concentration of dNTPs in a primer exchange reaction may be, for example, 2-1000 μM. In some embodiments, the dNTP concentration in a primer exchange reaction is 2-10 μM, 2-15 μM, 2-20 μM, 2-25 μM, 2-30 μM, 2-35 μM, 2-40 μM, 2-45 μM, 2-50 μM, 2-55 μM, 2-60 μM, 2-65 μM, 2-70 μM, 2-75 μM, 2-80 μM, 2-85 μM, 2-90 μM, 2-95 μM, 2-100 μM, 2-110 μM, 2-120 μM, 2-130 μM, 2-140 μM, 2-150 μM, 2-160 μM, 2-170 μM, 2-180 μM, 2-190 μM, 2-200 μM, 2-250 μM, 2-300 μM, 2-350 μM, 2-400 μM, 2-450 μM, 2-500 μM, 2-600 μM, 2-700 μM, 2-800 μM, 2-900 μM or 2-1000 μM. For example, the dNTP concentration in a primer exchange reaction may be 2 μM, 5 μM, 10 μM, 15 μM, 20 μM, 25 μM, 30 μM, 35 μM, 40 μM, 45 μM, 50 μM, 55 μM, 60 μM, 65 μM, 70 μM, 75 μM, 80 μM, 85 μM, 90 μM, 95 μM, 100 μM, 105 μM, 110 μM, 115 μM, 120 μM, 125 μM, 130 μM, 135 μM, 140 μM, 145 μM, 150 μM, 155 μM, 160 μM, 165 μM, 170 μM, 175 μM, 180 μM, 185 μM, 190 μM, 195 μM or 200 μM. In some embodiments, the dNTP concentration in a primer exchange reaction is 10-20 μM, 10-30 μM, 10-40 μM, 10-50 μM, 10-60 μM, 10-70 μM, 10-80 μM, 10-90 μM or 10-100 μM.

In some embodiments, dNTP variants are used. For example, PER systems may use hot start/clean amp dNTPs, phosphorothioate dNTPs, or fluorescent dNTPs. Other dNTP variants may be used. Because some modified dNTPs are less favorable than normal (unmodified) DNA-DNA binding, the hairpin back displacement process may be increased with their usage. Similarly, a hairpin comprised of a different type of nucleic acid (e.g., LNA, RNA or interspersed modified bases such as methyl dC or super T IDT modifications) may be used in some embodiments to increase the speed of a PER by forming stronger bonds than the synthesized primer with respect to the catalytic molecule.

In some embodiments, catalytic molecules are covalently linked to biomolecules such as fluorophores or proteins. In some embodiments, catalytic molecules contain a biotin modification, so they may be tethered to surfaces by a biotin-streptavidin bond. In some embodiments, catalytic molecules contain a modification such as an azide modification within one of the subdomains that allows them to be covalently linked to other molecules such as an alkyne through click chemistry. Other chemical and biological linkages are encompassed by the present disclosure.

It should be understood that the nucleic acids of the present disclosure do not occur in nature. Thus, the nucleic acids may be referred to as "engineered nucleic acids." An "engineered nucleic acid" is a nucleic acid (e.g., at least two nucleotides covalently linked together, and in some instances, containing phosphodiester bonds, referred to as a phosphodiester "backbone") that does not occur in nature. Engineered nucleic acids include recombinant nucleic acids and synthetic nucleic acids. A "recombinant nucleic acid" is a molecule that is constructed by joining nucleic acids (e.g., isolated nucleic acids, synthetic nucleic acids or a combination thereof) and, in some embodiments, can replicate in a living cell. A "synthetic nucleic acid" is a molecule that is amplified or chemically, or by other means, synthesized. A synthetic nucleic acid includes those that are chemically modified, or otherwise modified, but can base pair with (also referred to as "binding to," e.g., transiently or stably) naturally-occurring nucleic acid molecules. Recombinant and synthetic nucleic acids also include those molecules that result from the replication of either of the foregoing.

While an engineered nucleic acid, as a whole, is not naturally-occurring, it may include wild-type nucleotide sequences. In some embodiments, an engineered nucleic acid comprises nucleotide sequences obtained from different organisms (e.g., obtained from different species). For example, in some embodiments, an engineered nucleic acid includes a murine nucleotide sequence, a bacterial nucleotide sequence, a human nucleotide sequence, a viral nucleotide sequence, or a combination of any two or more of the foregoing sequences. In some embodiments, an engineered nucleic acid contain one or more random bases.

In some embodiments, an engineered nucleic acid of the present disclosure may comprise a backbone other than a phosphodiester backbone. For example, an engineered nucleic acid, in some embodiments, may comprise phosphoramide, phosphorothioate, phosphorodithioate, O-methylphophoroamidite linkages, peptide nucleic acids or a combination of any two or more of the foregoing linkages. An engineered nucleic acid may be single-stranded (ss) or double-stranded (ds), as specified, or an engineered nucleic acid may contain portions of both single-stranded and double-stranded sequence. In some embodiments, an engineered nucleic acid contains portions of triple-stranded sequence, or other non-Watson-Crick base pairing such as G-quartets, G-quadruplexes, and i-motifs. An engineered nucleic acid may comprise DNA (e.g., genomic DNA, cDNA or a combination of genomic DNA and cDNA), RNA or a hybrid molecule, for example, where the nucleic acid contains any combination of deoxyribonucleotides and ribonucleotides (e.g., artificial or natural), and any combination of two or more bases, including uracil, adenine, thymine, cytosine, guanine, inosine, xanthine, hypoxanthine, isocytosine and isoguanine.

Engineered nucleic acids of the present disclosure may be produced using standard molecular biology methods (see, e.g., Green and Sambrook, *Molecular Cloning*, A Laboratory Manual, 2012, Cold Spring Harbor Press). In some embodiments, nucleic acids are produced using GIBSON ASSEMBLY® Cloning (see, e.g., Gibson, D. G. et al. *Nature Methods*, 343-345, 2009; and Gibson, D. G. et al. *Nature Methods*, 901-903, 2010, each of which is incorporated by reference herein). GIBSON ASSEMBLY® typically uses three enzymatic activities in a single-tube reaction: 5' exonuclease, the 3' extension activity of a DNA polymerase and DNA ligase activity. The 5' exonuclease activity chews back the 5' end sequences and exposes the complementary sequence for annealing. The polymerase activity then fills in the gaps on the annealed domains. A DNA ligase then seals the nick and covalently links the DNA fragments together. The overlapping sequence of adjoining fragments is much longer than those used in Golden Gate Assembly, and therefore results in a higher percentage of correct assemblies. Other methods of producing engineered nucleic acids are known in the art and may be used in accordance with the present disclosure.

Reference is made herein to DNA origami "scaffold" and "staple" strands. These are terms known in the art.[60] A scaffold strand is typically a long single-stranded nucleic acid (e.g., DNA) having a length of greater than 200 nucleotides. A staple strand is typically a short single-stranded nucleic acid (oligonucleotide) having a length of 200 nucleotides or less. It should be understood that the length of 200 nucleotide (longer than or shorter than) is not itself important in defining the components of a DNA origami system, but rather the relative lengths are typically important. A DNA scaffold strand is longer than the multiple, shorter staple strands such that the shorter staple strands are used (through nucleotide base complementarity) to fold the longer scaffold strand into an arbitrary shape (e.g., 2D or 3D structure).

Primer Exchange Methods and Applications

During embryonic development, kinetic pathways combined with environmental signals lead to the assemblage of complex and functional structures such as organs and limbs. It is from this intimate relationship between kinetics, signaling and structures, as well as the incredible level of programmability and complexity in biological systems, that the present disclosure is based, at least in part. To date, it has been largely impossible to dynamically create shapes in response to environmental signals that are even close to the complexity of structures that can be formed with annealing protocols. The primer exchange technology provided herein bridges this gap. Examples of several applications in which PER may be used as a tools are depicted in FIGS. 6, 7, 11 and 18 and described below.

Triggered Growth and Folding of Structures

Primer exchange reactions (PERs), in some embodiments, are used to synthesize long, fixed length nucleic acid strands (FIG. 7A). The length of the nucleic acid strands depends on several factors, including the length and number of catalytic molecules in a reaction. Each catalytic reaction (including primer binding, strand displacing elongation of the primer and branch migration; see FIG. 1) adds a domain to the growing nucleic acid strand. Because all primer and catalytic molecule components are relatively small, strand synthesis can be engineered in crowded environments, such as those in fixed cells, where direct delivery of the fully synthesized nucleic acid scaffolds may not be feasible.

Each step of prescribed 1D growth (assembly) adds a new primer sequence (see, e.g., FIG. 2 bottom panel), therefore primer exchange reactions can be used to program a folded shape based on complementary nucleic acid domains through any number of annealing protocols (FIG. 7B).[9,27,38,51-53] Because primer exchange operates isothermally and its kinetics can be tuned to operate under a wide range of temperature and salt conditions, this method can be used to trigger assembly of complex structures. These complex structures may be used, for example, as markers for Cryo-EM (electron microscopy) and other types of imaging, or as scaffolds for the patterning of proteins and other biomolecules.

In addition to assembling structures by folding scaffold strands (e.g., long single-stranded nucleic acids having a length of greater than 100 nucleotides) into specific shapes, primer exchange reactions may be used to construct large structures in a time efficient fashion by designing structures with exponential growth kinetics. For example, large structures may be produced by assembling a dendritic scaffolding backbone (FIG. 7C). This backbone, in some embodiments, may be folded into different 2D and 3D shapes. Using the branching method depicted in FIGS. 10A-10C (see Example 5), for example, structures of similar size can be assembled in a much shorter period of time than the linear scaffold synthesis methods, with a time that scales sublinearly with the total length of the backbone. This permits much more time efficient construction of large shapes in situ.

Molecular Clocks and Timers

The primer exchange reaction system of the present disclosure is a modular technology that may also be used, for example, for engineering synthetic systems capable of measuring time between arbitrary molecular events (e.g., exposure to a physical or chemical signal) and encoding them in DNA in situ (functioning as "molecular clocks"). PER can be used to measures signal directly in their native environment, and, in some embodiments, without any fluorescent tagging or barcoding that could disrupt kinetics as well as the potential to detect multiple signals simultaneously. In some embodiments, PER systems may be used to record time by continually appending bases to the ends of strands during the time between the sensed events. The distribution of lengths of these strands can be used as an indicator for the amount of time between the two molecular signals, and this distribution can be read out directly on a denaturing gel, for example. Because the speed of the reaction can be controlled with the hairpin concentration, it is possible to measure time across many different timescales (e.g., minutes to hours, or more).

In addition to measuring the time between signals, primer exchange reactions may be used, in some embodiments, to measure signals over time (referred to as "molecular timers") (FIG. 11). By programming a set of state transitions and modifying the concentrations of catalytic hairpins for each state transition, timers can be used to release an output signal (output primer dissociates from catalytic hairpin) at a specific interval of time after the occurrence of an input signal. This type of control is useful, for example, for programmable materials and synthetic gene regulation. Further, this delay in time can be programmed across several timescales.

PER-based molecular clock and timer systems may be scaled up (multiplexed), in some embodiments, to detect and actuate on multiple signals at once. These systems perform complex logic operations and affect gene regulatory networks in several ways, adding to the myriad tools available to synthetic biologists. Additionally, the temporal control of signals and genes can be used to perform in vitro experiments on biomolecules, for example, to study their functional properties.

Environmentally Responsive Recorders

Organisms develop from single cells, self-assembling from a genomic program, with molecular signals directing the traversal of specialized developmental pathways. Inspired by these incredibly efficient and robust developmental pathways, synthetic developmental self-assembly is provided by the primer exchange reaction systems of the present disclosure, whereby different structures form as a result of temporal and spatial variations in signal concentrations. Using the structure synthesis framework and the signal detection and actuation capabilities described above, developmental self-assembly is programmed, in some embodiments, whereby structures grow and change shape in response to the different environmental signals they encounter over time. These structures will follow prescribed kinetic pathways while dynamically recording molecular events and assembling into specified structures for applications in imaging, systems biology, and biological signal processing. These reactions execute isothermally, and reaction kinetics can be modified to match the desired operating temperature, speed, and ionic concentration of the system. The successful implementation of this approach introduces a profound paradigm shift in the field of synthetic self-assembly, due to both its ability to adapt to different environmental conditions and its ability to run for extended periods of time with little or no human intervention. The primer exchange reaction systems as provided herein can be used to pattern and direct the growth of structures as markers for imaging, construct scaffolds for the patterning biomolecules, or even synthesize structures that form around a specific target molecule to capture it, for example.

PER encoding of detected signals into a nucleic acid strand can also be extended to implement "ticker tapes" capable of recording multiple signals over long periods of time. Because the entire history of every molecule that traverses the reaction step is recorded in a transcript, and these molecules have specific and consistent kinetic properties, these ticker tape transcripts can be used to calculate exact time traces of arbitrary signals in solution over time. These systems can be used to track system dynamics over time in situ and in vivo and provide an unparalleled technology capable of recording arbitrary signals over arbitrary amounts of time.

Figures 41A, 41B, 41C, 41D:
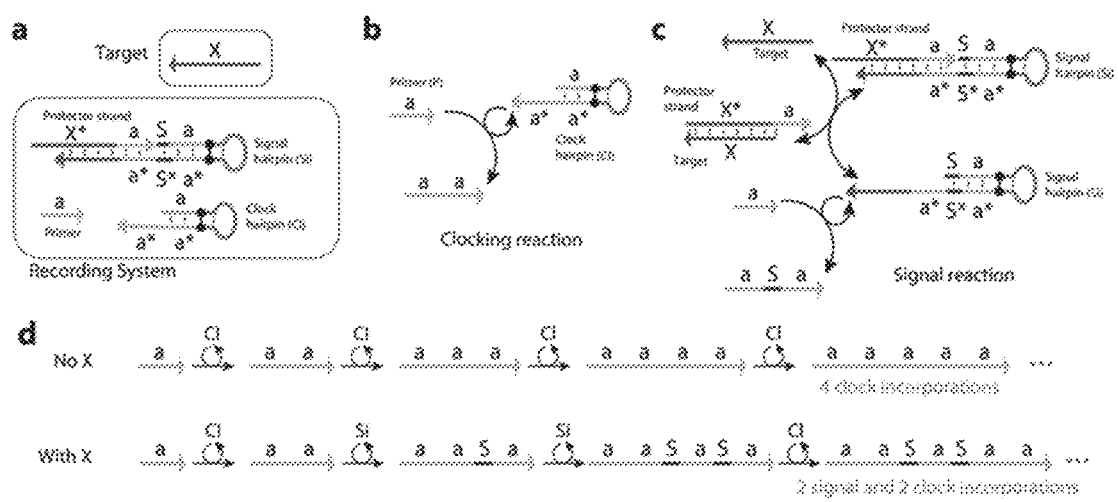

FIG. 41A shows an example of a molecular recording system that detects a target strand X that includes four components: a signal hairpin (Si), a protector strand that blocks the signal hairpin's primer binding site a*, a primer a, and a clock hairpin (Cl). A "protector strand" refers to a single-stranded nucleic acid that binds to the both the target and the 3' toehold domain of a catalytic molecule comprising a signal sequence. In some embodiments, the protector strand is longer than the 3' toehold domain (e.g., at least 1, 2, 3, 4, 5, 6, 7, 8, 9, or 10 nucleotides longer). FIG. 41B shows how a single clock incorporation is performed by the clock hairpin (Cl), which is programmed to concatenate an additional a domain onto a primer sequence ending in a. Because this clock is included at a constant concentration throughout the experiment, the rate of a incorporations onto growing primer strands stays roughly constant through time. This means the number and positions of the a domains in the final transcripts reflects the amount of time that passed between molecular events, similarly to the molecular clock fitting described in FIG. 13. As depicted in FIG. 41C, for example, in the presence of a target, a signal hairpin becomes active. This happens when the target X binds to an exposed single-stranded region on the protector strand and displaces that protector strand from the signal hairpin through a toehold exchange reaction. This exposes the primer binding site a* on the hairpin, so that the signal hairpin may append the sequence S a onto a primer ending in domain a. The sequence S represents a barcode sequence specific to target X that is used to indicate this reaction (a signal incorporation) happened instead of the clocking reaction (a clock incorporation). Because the toehold exchange system reaches a predictable equilibrium state, the rate of signal incorporations at a given point in time reflects the concentration of the target X at that time. Thus, the relative rate of signal to clock incorporations can be used to fit a concentration curve of the target B over the experiment time. As shown in FIG. 41D, for example, when no target is present, there are no signal barcodes in the transcripts, so all incorporations are clocks. However, when target is present, the signal incorporations (S a) are intercalated into the concatenations of the repeated domain B, and their time-varying frequencies are lit to recover the time-varying concentration values for target B.

Figures 42A, 42B, 42C, 42D:
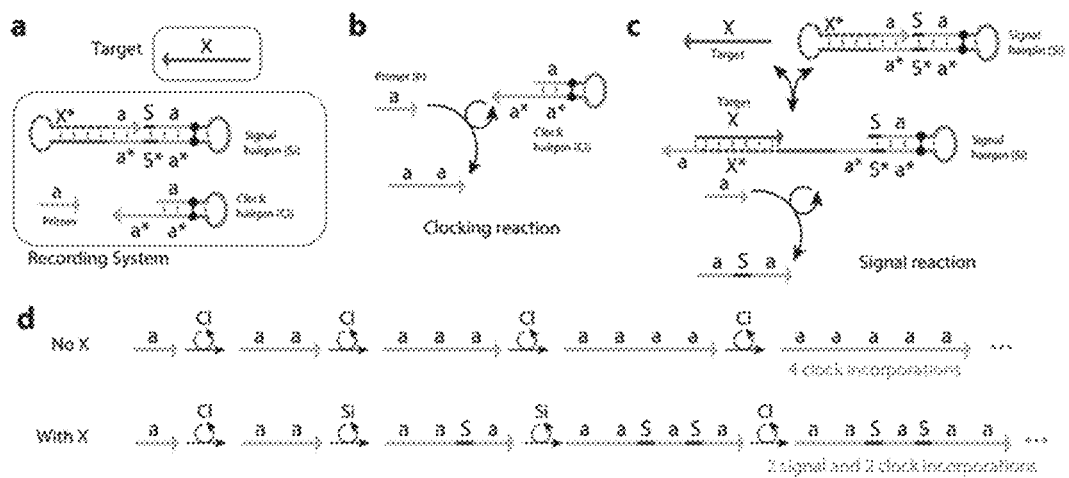

FIG. 42A depicts an example of a molecular recording system that detects a target strand B that includes three components: a signal hairpin (Si) that folds into a configuration that initially blocks the primer binding site a*, a primer a, and a clock hairpin (Cl). FIG. 42B shows an example of how a single clock incorporation is performed by the clock hairpin (Cl), which is programmed to concatenate an additional a domain onto a primer sequence ending in a. Because this clock is included at a constant concentration throughout the experiment, the rate of a incorporations onto growing primer strands stays approximately constant through time. Thus, the number and positions of the a domains in the final transcripts reflects the amount of time that passed between molecular events, similarly to the molecular clock fitting described in FIG. 13. As depicted in FIG. 42C, for example, in the presence of a target, a signal hairpin becomes active. This happens when the target X binds to an exposed single-stranded loop region on the signal hairpin and displaces the strand that is blocking the primer binding site a* through a toehold exchange reaction. This allows the signal hairpin to append the sequence S a onto a primer ending in domain a. The sequence S represents a barcode sequence specific to target X that is used to indicate this reaction (a signal incorporation) happened instead of the clocking reaction (a clock incorporation). Because the toehold exchange system reaches a predictable equilibrium state, the rate of signal incorporations at a given point in time reflects the concentration of the target X at that time. Thus, the relative rate of signal to clock incorporations can be used to fit a concentration curve of the target X over the experiment time. As depicted in FIG. 42D, for example, when no target is present, there are no signal barcodes in the transcripts, so all incorporations are clocks. However, when target is present, the signal incorporations (S a) are intercalated into the concatenations of the repeated domain a, and their time-varying frequencies are fit to recover the time-varying concentration values for target X. In general, additional signal hairpins with target-specific signal sequence barcodes can be used for multiplexed monitoring of many different targets over time. A two-signal example of a ticker tape is shown in FIG. 20.

Additional Applications

Triggered synthesis of cryo-EM markers in situ. The triggered growth of large, structurally sound DNA nanostructures upon proteins can be used as a marker for structure determination using cryo-EM. With an asymmetric marker of a known shape, the process of class averaging and 3D reconstruction of protein structure should be easier. This approach is particularly useful, for example, for mapping the structure of proteins that are otherwise difficult to image.

Long term environmental surveillance of pollutants. Primer exchange reactions are powered by dNTPs and can run for extended periods of time. Molecular recorders that measure pollutant levels in a solution over long periods of time can be implemented through the tethering of primer exchange reactants to the side of a chamber exposed to the environment.

Construction of pH, temperature meters. Changes in pH and temperature have predictable effects on polymerase and reaction kinetics, thus PER systems can be used to keep track of the temperature or pH to which they are exposed. Because pH and temperature affect polymerase kinetics, an external clock, such as the proposed light gated mechanism, may be used for precise time traces.

Programmed obsolescence for transient materials. Using programmable pulses of protein synthesis, for example, a primer exchange system can detect a particular environmental signal and then first produce a reagent that polymerizes the solution and then a set amount of time later produce a reagent that completely destroys the polymerized substrate.

Drug delivery on a schedule. By implementing reaction cycles, oscillations of actuating periods can be programmed with primer exchange reactions. This recurring state can activate the periodic release of a particular signal, which subsequently can be transduced to a protein signal through a toehold switch. Due to the modularity of primer exchange reactions and toehold switches, the output of the system can be a therapeutic protein produced after specific intervals and only in response to particular environmental signals.

Conditional gene synthesis for environmental control. Primer exchange reactions implemented with RNA, and/or encoded in the genome, can be used to record and modulate gene expression through the synthesis of functional RNA regulators or mRNA transcripts. In some embodiments, PER is used for conditional gene regulation.

Triggered encapsulation of toxins in situ. Because growth of structures is triggered by primers and can be conditional on the presence of environmental signals, a signal detection method is also provided, whereby the detection of a particular pathogenic marker is immediately followed by the triggered growth of a structure surrounding and inactivating the toxin.

In situ signal amplification. Growth of long telomeric concatemers may be used for in situ signal amplification for imaging, for example. Multiple telomerization reactions can be run in parallel to multiplex the signal amplification. See, e.g., FIG. 25.

Protein Detection. Conditional primer exchange reactions can also be adapted to detect proteins in addition to amino acids by using an aptamer sequence that conditionally exposes the requisite primer binding site. This enables a large range of molecular behaviors, as the synthesis could interface with many different molecular entities for recording and programming behavior.

In Vivo Applications

In some embodiments, implementing PER cascades in vivo enables programmable, dynamic synthesis of nucleic acids within cells. These systems can be responsive on a single-cell level, creating a population of transcripts synthesized according to the particular cellular environment. These transcripts may be records of signals detected over time, or they may be functional RNA transcripts that cause cells to have a programmed response to specific cellular conditions.

With RNA PER in eukaryotic cells, as an example, localization markers such as the Nuclear Localization Signal (NLS) sequences can be appended dynamically to an mRNA sequence before it leaves the nucleus to direct the synthesized protein back into the nucleus. This spatial programmability can be useful for specific activation or deactivation of proteins.

In general, PER cascades are largely sequence-independent, so that arbitrary sequences can be synthesized de novo or appended to extant oligonucleotides. Each cell type requires a strand displacing polymerase, ideally an RNA polymerase already provided in cells to limit disruption to cell processes. Any proteins used to implement the stop sequence for hairpins should be incorporated as well. One example is to use a dCas9 protein, possibly evolved to have stronger binding, as it has been successfully introduced to prokaryotes and eukaryotes.

Real-time synthesis can be monitored by using the dynamically synthesized output sequences to activate or inhibit a fluorescent reporter gene. For example, DNAzyme may be synthesized to cleave the mRNA of a GFP protein. Alternatively, a guide RNA can be synthesized to inhibit a reporter gene. If the sequence information encoded in the transcripts does not need to be recovered immediately, then the records produced within cells can be later sequenced to extract the temporal recording information.

Because the PER hairpins act catalytically, the rate of the reaction can be tuned over several orders of magnitude in vitro. In the cells, factors like copy number of plasmids could be adjusted according to necessary synthesis rates in order to control the concentrations. In some instances, performance may first be evaluated in an in vitro transcription/translation system such as PURExpress length resolution and/or a cell extract if available for the desired cell type.

As one example, synthesized strands can inhibit genes through cleaving mRNAs, generating context-specific guide RNAs, synthesizing an antisense transcript, or by activating an siRNA pathway. mRNA transcripts may also be synthesized or extended in a modular fashion to create new proteins on demand that have domains tailored to each context. Many types of regulatory nucleic acids and proteins can be detected and recorded over time.

Having a highly programmable in vivo synthesis platform, which can dynamically synthesize sequences and respond to different environmental conditions, has major applications in synthetic biology. Target proteins can be equipped with primers that record hairpins localized to different parts of the cell to elucidate spatio-temporal information about the target of interest. In general, PER in vivo brings an entirely new method of dynamic and responsive nucleic acid synthesis in the cell, and its highly programmable nature makes the possibilities of the technology applicable in many different contexts.

Molecular Motors

Also provided herein are molecular motor systems that inspect molecular environments at the molecular level. To do this, the unit operation should occur at a local scale and the subsequent operations should happen in a sequential manner along neighboring sites. The unit interaction should have a well-defined distance-dependent behavior. The reaction rate of a unit step depends on the lengths of different parts of the crawlers and templates, and on the distance between sites. A "molecular crawler" is a snake-like molecular species that roams around a track, spanning across the whole trajectory as it grows from the first track site to the final track site (see, e.g., FIG. 31A). As the crawler moves between sites, it copies the information from the sites and records the information in its growing body (nucleic acid). A "molecular walker" moves between sites, leaving the previous site after each step (see, e.g., FIG. 32A). While traveling along a track, the walker grows its body, copying and retaining the information from the track sites.

The mechanisms of the unit operation on a single site are shown in the top rows of FIGS. 31A and 32A. In both systems, the reaction is initiated by binding of a primer (input signal; 'a' in FIG. 31A and '1' in FIG. 32A) onto their complementary primer-binding region of the site. The next step is elongation of the primers by a polymerase along the template until the polymerase hits the "polymerase stopper" points (a molecule that terminates polymerization). DNA base monomers (dNTPs) are supplied in the system for the polymerase to add to the newly synthesized part. The stopping points can be encoded by one of the following two ways, for example. A non-nucleotide chemical spacer (e.g., triethylene glycol spacer) may be added as a stopper, or a subset of bases may be used in a system and the excluded base used as the stopper. Other molecules that terminate polymerization are described elsewhere herein. For example, if a three-letter code with A, T, and C in the template is used, their complement base monomers, A, T, and G, are supplied in the system, and G's are embedded at the end of the template. The polymerase cannot extend the new strand because the system does not have the complement base monomer, C. When the polymerase finishes the synthesis of the new domain and reaches the stopper point, it leaves (dissociates from) the template. Then, since the newly synthesized domain shares the same sequence as the template, it can undergo a random walk branch migration process. If the original template displaces the newly synthesized domain, a new primer for the next reaction is exposed.

After the unit operation, in both molecular motor systems, the first site has a newly synthesized domain that can now act as a primer for the next site. Since the molecular motor molecule (e.g., crawler or walker) is still anchored on the first site—the lengths of the relevant parts in the molecule will be designed to satisfy this condition—the new primer only acts locally on the sites in proximity. The movement mechanisms to the next sites are different between the two systems. In the molecular crawler system, the new primer binds the primer-binding region of the next site through complementarity, and the unit operation is repeated. The outcome is a crawler with an extended body along the second site (middle row of FIG. 31A). Note that the primer-binding domains (e.g., domain b* of the second site) should be protected against primer extension, to prevent spontaneous release of the crawler in the middle of the track; such protection is achieved by incorporating non-extendable bases, such as inverted-dT at the 3-end of the strand, for example.

In the molecular walker system, the walker molecule undergoes a competitive branch migration process between the current and the next sites (middle row of FIG. 32A). If the second site displaces the corresponding part of the first site, the walker can be transported to the second site; the lengths of the primers should be designed such that the binding of one primer to its complement (e.g., between domains 1 and 1*) is weak enough to release the walker from the previous site, while the binding of two consecutive primers to their complement (e.g., between domains 1-2 and 2*-1*) is strong enough to hold the walker on the next site. However, since the walker still contains a domain that is complementary to the primer-binding region of the previous site, the motion of a walker is reversible (can walk back). This can be a feature in cases where revisits of multiple sites are necessary, e.g., in maze solving. Note that the track sites recover their original form after a walker leaves the sites, thus becoming reusable.

After repeating the steps along three adjacent sites (bottom rows of FIGS. 28A and 29A), the snake-like crawler now spans across the whole track, while the walker has traversed to the final site. The release of the crawlers, for retrieval of the record and history, can be implemented by multiple methods. In one example, at the end of recording reaction, a "reverse primer" can be added to synthesize a complement copy of the crawler, displacing the crawler off of the template tracks. For example, a primer with the domain "d*" in the case of the snake-like crawler, and a primer with the domain "5*" in the case of walker, can initiate such a reverse copy process. As another example, a special kind of track site that directs a reverse copy process in an autonomous fashion can be embedded just after the final site. Primers containing domains "d*" and "5*", in the respective cases, can be incorporated at the special site to initiate the reverse copy process when the motors come in proximity. As yet another example, a more simple mechanism, based on heat-mediated dehybridization of motors can be used. While system-wide heat could denature the platform structures or some components, selective detection of target signals is possible, when combined, for example, with PCR amplification with specific primers.

In some embodiments, a variably-long string of concatenated barcodes may be generated with probes repeatedly used as provided herein, enabling parallel operation of the relatively slow steps of stem-encoded template copying, release, and downstream binding. As depicted in FIG. 44A, in addition to the primer binding site of domain "a," probes include another primer binding site (domain "b") appended to the 3' end of the probe. Also, in a some embodiments, the "stopper pair" is the unnatural base pair iso-dC:iso-dG (Integrated DNA Technologies), and the unextended primer contains a phosphorothioate bond between the final two bases. These modifications stop the polymerase after copying hairpin template "b-C" (stopper pair) and bias the equilibrium state of the hairpin probe and extended primer such that the extended primer is more likely single-stranded and the hairpin is closed. Domain "t" represents a random barcode or other probe-specific information. Free primers, in excess to hairpin probes, initially bind the probe as usual and are extended by a displacing polymerase (FIG. 44B). Instead of copying a palindromic domain in APR, new domain "b*" is capable of binding domain "b" on the free 3' end of any other probe.

In some embodiments, domain lengths or sequences are adjusted to limit or prevent self-binding. When "b*" is bound to another probe, any one of several methods shown (methylated RNA bases on probe, a mismatch at the terminal nucleotide between "b*" and "b," an iso-dC nucleotide on the probe and a corresponding iso-dG nucleotide on the 5' end of each "a*" primer, or similar) can be used to slow or stop further polymerization. In the case of methylated RNA nucleotides, for example, polymerases like Bst (Integrated DNA Technologies) or Bsm (Thermo Fisher) were found to be slowed from further extension. In the case of a mismatch nucleotide, this allows close but imperfect matching of DNA ends, slowing or preventing further polymerization but still allowing "sloppy" ligases (e.g., T4 DNA ligase) to ligate the connection. If the slow/stopper fails, the reaction proceeds as with previous crawler designs for that step. As with the crawler designs, the new, concatenated barcode strand can be terminated by occasionally binding a low-concentration, free "b" domain strand, which results in a polymerase copying the new concatenated strand, releasing it from all probes, and thus re-generating probes for further use (FIG. 44D). The final result, as with the crawler, is a somewhat random patchwork of concatenated barcode copies, at first bound to their respective probes but later released and repeated in a potentially different pattern (FIG. 44E). As before, strand content may be analyzed by PCR, hybridization, next generation sequencing, or other means. FIG. 44F provides examples of probe sequences, with their respective domains denoted.

Molecular motor systems, in some embodiments, use molecular instruments for parallel "bottom-up" inspection of large populations of molecular-scale targets. Molecular records may be repeatedly created along the molecular landscape of the given targets, each labeled with a unique DNA barcode, without disturbing or destroying the targets themselves, and later read by high-throughput sequencing for computational reconstruction of the image of the underlying targets. With sample and "instrument" on the same scale, this technology addresses many challenges associated with microscope-based technologies. For example, high spatial resolution of dynamic processes can be recorded; molecular instruments, being the same size of their targets, will have "ultra-sharp molecular vision." As another example, with each target (rather than target species) uniquely barcoded, the molecular motor systems offer high multiplexing to follow the spatial and temporal distribution of every molecule. As yet another example, the molecular motors can record processes in a massively parallel manner, enabling ultra-high throughput molecular imaging. As still another example, the molecular motors can access molecular targets in situ without the structural or environmental constrains of top-down microscopy, and avoid harsh and damaging sample processing. The potential of the molecular motor system to in situ identify, follow, and record the landscapes of individual molecules in a massively parallel fashion, followed by reading and re-assembly of the information, enables the computational re-creation of the images of molecular structures with high precision. Molecular motors further enable quantification of molecular targets within a space that is not resolvable by microscopy, and ultra-high resolution visualization of biological structures, true connectivity and dynamics data from individual networks, for example. The molecular motor systems transform fundamental biological research, drug discovery, and diagnostics, by providing a highly useful tool for parallel and multiplexed examination of molecular landscapes.

Track sites for molecular motors (e.g., crawler molecules and walker molecules), in some embodiments, comprise (i) an unpaired 3' toehold domain and (ii) a paired domain located 5' from the toehold domain that is formed by base pairing between nucleotides of a displacement strand and nucleotides of a template strand containing the toehold domain. Examples of track sites having this configuration are shown in FIG. 31A and FIG. 32A.

With reference to FIG. 31A, the unpaired 3' toehold domain (similar to the toehold domain of the PER system discussed above) is denoted by 'a*'. The nucleic acid strand containing the unpaired toehold domain is referred to as the "template strand." This is the strand to which the primer anneals to initiate polymerization. The opposing strand, to which the template strand is bound (paired, hybridized) is referred to as the "displacement strand." Subdomains '1' and 'b' of the displacement strand pair respectively with subdomains '1*' and 'b*' of the template strand to form the paired domain located 5' from the toehold domain. During polymerization initiated by binding of the primer to the toehold domain of the template strand, the displacement strand is initially displaced by the elongation product. Subsequently, however, the displacement strand displaces the elongation product and binds again to template strand (a process referred to as branch migration) (top row). The elongation product, now containing information from the initial molecular site is then free to function as a primer and bind to the toehold domain of another molecular site, starting another cycle of the elongation/branch migration process (middle row). With each cycle, a record of information from each molecular site is added to a growing nucleic acid polymer strand, referred to as the crawler molecule (bottom row, '1+2+3').

With reference to FIG. 32A, the unpaired 3' toehold domain is denoted by '1*'+'2*'. The nucleic acid strand containing the unpaired toehold domain is the template to which primer '1' anneals to initiate polymerization. The opposing strand, to which the template strand is bound (paired, hybridized) is the displacement strand. Subdomain '3' of the displacement strand pairs with subdomain '3*' of the template strand to form the paired domain located 5' from the toehold domain. During polymerization initiated by binding of the primer to the toehold domain of the template strand, the displacement strand is initially displaced by the elongation product. Subsequently, however, the displacement strand displaces the elongation product and binds again to template strand (top row). The elongation product, now containing information from the initial molecular site is then free to function as a primer and bind to the toehold domain (in this case, to subdomain '3*' of the toehold domain) of another molecular site, starting another cycle of the elongation/branch migration process (middle row). With each cycle, a record of information from each molecular motor (each interaction between molecular motors) is added to a growing nucleic acid polymer strand, referred to as the walker molecule (bottom row, '1+2+3+4+5').

A track site for a molecular motor, as discussed above, generally includes an unpaired (single-stranded) 3' toehold domain and a paired (double-stranded) stem domain located 5' from the 3' toehold domain. In some embodiments, the paired domain is directly adjacent to the toehold domain.

The length of a track site molecule may vary. In some embodiments, a molecular motor has a length of 25-300 nucleotides. For example, a track site molecule may have a length of 25-250, 25-200, 25-150, 25-100, 25-50, 50-300, 50-250, 50-200, 50-150 or 50-100 nucleotides. In some embodiments, a track site molecule has a length of 30-50, 40-60, 50-70, 60-80, 70-90, 80-100, 100-125, 100-150 or 100-200 nucleotides. In some embodiments, a track site molecule has a length of 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 nucleotides. A track site molecule, in some embodiments, is longer than 300 nucleotides, or shorter than 25 nucleotides.

A "toehold domain," discussed above, refers to an unpaired sequence of nucleotides located at the 3' end of a track site molecule and is complementary to (and binds to) a nucleotide sequence of a primer (or primer domain of a primer). The length of a toehold domain may vary. In some embodiments, a toehold domain has a length of 5-40 nucleotides. For example, a toehold domain may have a length of 2-35, 2-30, 2-25, 2-20, 2-15, 2-10, 5-35, 5-30, 5-25, 5-20, 5-15, 5-10, 10-40, 10-35, 10-30, 10-25, 10-20, 10-15, 15-40, 15-35, 15-30, 15-25, 15-20, 20-40, 20-35, 20-30, 20-25, 25-40, 25-35, 25-30, 30-40, 30-35 or 35-40 nucleotides. In some embodiments, a toehold domain has a length of 5, 10, 15, 20, 25, 30, 35 or 40 nucleotides. In some embodiments, a toehold domain has a length of 10, 11, 12, 13, 14, 15, 16, 17, 18, 19, 20, 21, 22, 23, 24 or 25 nucleotides. A toehold domain, in some embodiments, is longer than 40 nucleotides, or shorter than 5 nucleotides.

In some embodiments, a toehold domain has subdomains (e.g., two subdomains), as depicted, for example, in FIG. 32A. In such embodiments, a primer typically binds to the most 3' subdomain ('1*'). That is, the primer used in the molecular motor reaction does not necessarily span the entire length of the toehold domain—it may bind to only a subdomain (a portion of) the toehold domain.

A "paired domain" of a track site molecule refers to a paired sequence of nucleotides (e.g., Watson-Crick nucleobase pairing) located adjacent to (and 5' from) the unpaired toehold domain of a track site. The paired domain of a track site molecule is formed by base pairing between domain(s) of the template strand and domain(s) of the displacement strand. The length of a paired domain may vary. In some embodiments, a paired domain has a length of 5-40 nucleotides. For example, a paired domain may have a length of 5-35, 5-30, 5-25, 5-20, 5-15, 5-10, 10-40, 10-35, 10-30, 10-25, 10-20, 10-15, 15-40, 15-35, 15-30, 15-25, 15-20, 20-40, 20-35, 20-30, 20-25, 25-40, 25-35, 25-30, 30-40, 30-35 or 35-40 nucleotides. In some embodiments, a paired domain has a length of 5, 10, 15, 20, 25, 30, 35 or 40 nucleotides. In some embodiments, a paired domain has a length of 10, 11, 12, 13, 14, 15, 16, 17, 18, 19, 20, 21, 22, 23, 24 or 25 nucleotides. A paired domain, in some embodiments, is longer than 40 nucleotides, or shorter than 5 nucleotides.

In some embodiments, extension of a primer (bound to a primer-binding site) by a strand displacement polymerase is terminated by the presence of a molecule or modification in the track site that terminates polymerization. Thus, in some embodiments, track sites molecular motors of the present disclosure comprise a molecule or modification that terminates polymerization. A molecule or modification that terminates polymerization ("stopper") is typically located in a paired domain on the template strand of a track site such that polymerization terminates extension of the primer through the paired domain. In some embodiments, the molecule that terminates polymerization is a synthetic non-DNA linker, for example, a triethylene glycol spacer, such as the Int Spacer 9 (iSp9) or Spacer 18 (Integrated DNA Technologies (IDT)). It should be understood that any non-native linker that terminates polymerization by a polymerase may be used as provided herein. Other non-limiting examples of such molecules and modifications include a three-carbon linkage (/iSpC3/) (IDT). ACRYDITE™ (IDT), adenylation, azide, digoxigenin (NHS ester), cholesteryl-TEG (IDT), I-LINKER™ (IDT), and 3-cyanovinylcarbazole (CNVK)

and variants thereof. Typically, but not always, short linkers (e.g., iSp9) lead to faster reaction times.

In some embodiments, the molecule that terminates polymerization is a single or paired non-natural nucleotide sequence, such as iso-dG and iso-dC (IDT), which are chemical variants of cytosine and guanine, respectively. Iso-dC will base pair (hydrogen bond) with Iso-dG but not with dG. Similarly, Iso-dG will base pair with Iso-dC but not with dC. By incorporating these nucleotides in a pair on opposite sides of the paired domain, at the stopper position, the polymerase will be halted, as it does not have a complementary nucleotide in solution to add at that position.

In some embodiments, the efficiency of performance of a "stopper" modification is improved by lowering dNTP concentrations (e.g., from 200 µM) in a reaction to 100 µM, 10 µM, 1 µM, or less.

Inclusion of a molecule or modification that terminates polymerization often creates a "bulge" in a double-stranded domain of catalytic molecule (e.g., a stem domain for hairpin structures), because the molecule or modification is not paired. Thus, in some embodiments, track sites for molecular motors include, opposite the molecule or modification, a single nucleotide (e.g., thymine), at least two of same nucleotide (e.g., a thymine dimer (TT) or trimer (TTT)), or an non-natural modification.

Molecular motor systems, in additional to track site molecules, include primers, referred to as input primers or output primers, which get extended to become crawler molecules and/or walker molecules. Primers are described elsewhere herein.

A complete "step" of a molecular motor reaction is depicted in FIG. 31A. An input primer ('a') binds to a toehold domain ('a*') of a track site molecule to start the reaction. Upon binding to the track site molecule in reaction solution containing polymerase (e.g., strand displacing polymerase) and dNTPs, the initial primer is extended through the paired domain, displacing the displacement strand (subdomains '1+b') of the paired domain. The displaced strand then competes with the extended primer for binding (reannealing) with its complementary binding domain on the template strand, thereby displacing the extended output primer. This completes a step of the reaction. The displaced output primer "1+b" may then go on to function as an input primer in the next step of the reaction.

In some embodiments, a primer or primer domain (the nucleotide sequence that binds to the toehold domain of a track site molecule) has a length of 10-50 nucleotides. For example, a primer or primer domain may have a length of 10-45, 10-40, 10-35, 10-30, 10-25, 10-20, 10-15, 15-50, 15-45, 15-40, 15-35, 15-30, 15-25, 15-20, 20-50, 20-45, 20-40, 20-35, 20-30, 20-25, 25-50, 25-45, 25-40, 25-35, 25-30, 30-50, 30-45, 30-40, 30-35, 35-50, 35-45, 35-40, 40-50, 40-45 or 45-50 nucleotides. In some embodiments, a primer or primer domain has a length of 10, 15, 20, 25, 30, 35, 40, 45 or 50 nucleotides. In some embodiments, a primer or primer domain has a length of 15, 16, 17, 18, 19, 20, 21, 22, 23, 24 or 25 nucleotides. A primer or primer domain, in some embodiments, is longer than 50 nucleotides, or shorter than 10 nucleotides. It should be understood that the full length of a primer depends, at least in part, on the number and length of appended (polymerized) sequences, which depends on the number and length of track site molecule present in a reaction.

A primer, as provided herein, may be linked to (labeled with) a detectable molecule (e.g., a molecule that emits a detectable signal, such as a fluorescent or chemiluminescent signal). In some embodiments, the label is a fluorophore. A primer linked to a fluorophore or other fluorescent/chemiluminescent molecule is referred to simply as a "fluorescent primer." Examples of fluorophores that may be used herein include, without limitation, hydroxycoumarin, methoxycoumarin, Alexa fluor, aminocoumarin, Cy2, FAM, Alexa fluor 405, Alexa fluor 488, Fluorescein FITC, Alexa fluor 430, Alexa fluor 532, HEX, Cy3, TRITC, Alexa fluor 546, Alexa fluor 555, R-phycoerythrin (PE), Rhodamine Red-X, Tamara, Cy3.5 581, Rox, Alexa fluor 568, Red 613, Texas Red, Alexa fluor 594, Alexa fluor 633, Allophycocyanin, Alexa fluor 647, Cy5, Alexa fluor 660, Cy5.5, TruRed, Alexa fluor 680, Cy7 and Cy7.5. Other fluorophores and molecules that emit a detectable signal are encompassed by the present disclosure.

In some embodiments, a detectable molecule is linked to the track site molecule rather than the primer.

In some embodiments, a track site molecule is linked to a biomolecule. Biomolecules include, for example, nucleic acids (e.g., DNA or RNA) and proteins. A biomolecule may be a therapeutic, prophylactic, diagnostic or imaging molecule. In some embodiments, a biomolecule is a disease-related or drug-related biomolecule, such as a cancer-related gene or protein, or an FDA-approved or potential drug target. In some embodiments, a biomolecule is an enzyme, an antigen, a receptor, a ligand, a membrane protein, a secreted protein, or a transcription factor.

Molecular motor systems require the use of a polymerase. In some embodiments, the polymerase is a DNA polymerase (DNAP), such as a DNA polymerase having DNA strand displacement activity. "Strand displacement" describes the ability to displace downstream DNA encountered during synthesis. Examples of polymerases having DNA strand displacement activity that may be used as provided herein include, without limitation, phi29 DNA polymerase (e.g., NEB #M0269), Bst DNA polymerase, large fragment (e.g., NEB #M0275), or Bsu DNA polymerase, large fragment (e.g., NEB #M0330). Other polymerases having strand displacement activity may be used. In some embodiments, the polymerase is a RNA polymerase.

In some embodiments, the polymerase is phi29 DNA polymerase. In such embodiments, the reaction conditions may be as follows: 1× reaction buffer (e.g., 50 mM Tris-HCl, 10 mM MgCl$_2$, 10 mM (NH$_4$)$_2$SO$_4$, 4 mM DTT) supplement with purified bovine serum albumin (BSA), pH 7.5, incubated at 30° C.

In some embodiments, the polymerase is Bst DNA polymerase, large fragment. In such embodiments, the reaction conditions may be as follows: 1× reaction buffer (e.g., 20 mM Tris-HCl, 10 mM (NH$_4$)$_2$SO$_4$, 10 mM KCl, 2 mM MgSO$_4$, 0.1% TRITON® X-100), pH 8.8, incubated at 65° C.

In some embodiments, the polymerase is Bsu DNA polymerase. In such embodiments, the reaction conditions may be as follows: 1× reaction buffer (e.g., 50 mM NaCl, 10 mM Tris-HCl, 10 mM MgCl$_2$, 1 mM DTT), pH 7.9, incubated at 37° C.

The concentration of primer, molecular tracks and dNTPs in a reaction system may be varied depending, for example, on the particular application and kinetics required for that particular application.

The concentration of primer in a reaction may be, for example, 10 nM to 1000 nM. In some embodiments, the primer concentration in a reaction is 10-20, 10-30, 10-40, 10-50, 10-60, 10-70, 10-80, 10-90, 10-100, 10-125, 10-150, 10-200, 25-50, 25-75, 25-100, 25-150, 25-200, 50-75, 50-100, 50-150 or 50-200 nM. In some embodiments, the primer concentration in a reaction is 100-200, 100-300, 100-400, 100-500, 100-600, 100-70, 100-800, 100-900 or 100-1000 nM. In some embodiments, the primer concentration in a reaction is 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195 or 200 nM. In some embodiments, the primer concentration in a reaction is 100, 200, 300, 400, 500, 600, 700, 800, 900 or 1000 nM. The concentration of primer in a reaction may be less than 10 nM or greater than 1000 nM.

The concentration of track site molecules in a reaction may be, for example, 5 nM to 1000 nM. In some embodiments, the track site molecule concentration in a reaction is 5-10, 5-20, 5-30, 5-40, 5-50, 5-60, 5-70, 5-80, 5-90, 5-100, 5-125, 5-150, 5-200, 10-50, 10-75, 10-100, 10-150, 10-200, 25-75, 25-100, 25-125 or 25-200 nM. In some embodiments, the track site molecule concentration in a reaction is 10-200, 10-300, 10-400, 10-500, 10-600, 10-70, 10-800, 10-900 or 10-100 nM. In some embodiments, the track site molecule concentration in a reaction is 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195 or 200 nM. In some embodiments, the track site molecule concentration in a reaction is 10, 20, 30, 40, 50, 60, 70, 80, 90 or 100 nM. The concentration of track site molecule in a reaction may be less than 5 nM or greater than 1000 nM.

The ratio of primer to track site molecule in reaction may be 2:1 to 100:1. In some embodiments, the ratio of primer to molecular motor is 2:1, 3:1, 4:1, 5:1, 6:1, :1, 8:1, 9:1, 10:1, 11:1, 12:1, 13:1, 14:1, 15:1, 16:1, 17:1, 18:1, 19:1 or 20:1. In some embodiments, the ratio of primer to track site molecule is 30:1, 40:1, 50:1, 60:1, 70:1, 80:1 or 90:1.

The number of different track site molecules in a reaction in non-limiting. A reaction may comprise $1-10^{10}$ different track site molecules (each with a specific toehold domain sequence, for example). In some embodiments, a reaction comprises 1-10, 1-102, $1-10^3$, $1-10^1$, $1-10^1$, $1-10^6$, $1-10^7$, $1-10^8$, $1-10^9$, $1-10^{10}$, or more, different track site molecule. In some embodiments, a reaction comprises 1-5, 1-10, 1-15, 1-20, 1-25, 1-30, 1-35, 1-40, 1-45, 1-50, 1-55, 1-60, 1-65, 1-70, 1-75, 1-80, 1-85, 1-90, 1-95, 1-100, 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 10-15, 10-20, 10-25, 10-30, 10-35, 10-40, 10-45, 10-50, 10-55, 10-60, 10-65, 10-70, 10-75, 10-80, 10-85, 10-90, 10-95 or 10-100 different track site molecule. In some embodiments, a reaction comprises 1, 2, 3, 4, 5, 6, 7, 8, 9, 10, 11, 12, 13, 14, 15, 16, 17, 28, 19, 20, 21, 22, 23, 24 or 25 different track site molecule. Track site molecule are different from each other if their toehold domains differ from each other, for example.

The kinetics of a reaction may be controlled by varying temperature, time, buffer/salt conditions, and deoxyribonucleotide triphosphate (dNTP) concentrations, for example. Polymerases, like most enzymes, are sensitive to many buffer conditions, including ionic strength, pH and types of metal ions present (e.g., sodium ions vs. magnesium ions). Thus, the temperature at which a reaction is performed may vary from, for example, 4° C. to 65° C. (e.g., 4° C., 25° C., 37° C., 42° C. or 65° C.). In some embodiments, the temperature at which a reaction is performed is 4-25° C., 4-30° C., 4-35° C., 4-40° C., 4-45° C., 4-50° C., 4-55° C., 4-60° C., 10-25° C., 10-30° C., 10-35° C., 10-40° C., 10-45° C., 10-50° C., 10-55° C., 10-60° C., 25-30° C., 25-35° C., 25-40° C., 25-45° C., 25-50° C., 25-55° C., 25-60° C., 25-65° C., 35-40° C., 35-45° C., 35-50° C., 35-55° C., 35-60° C., or 35-65° C. In some embodiments, a reaction is performed at room temperature, while in other embodiments, a reaction is performed at 37° C.

A reaction may be performed (incubated) for 30 minutes (min) to 24 hours (hr). In some embodiments, a reaction is carried out for 10 min, 35 min, 40 min, 45 min, 50 min, 55 min, 60 min, 1 hr, 2 hr, 3 hr, 4 hr, 5 hr, 6 hr, 7 hr, 8 hr, 9 hr, 10 hr, 11 hr, 12 hr, 18 hr or 24 hr.

The concentration of dNTPs in a reaction may be, for example, 2-1000 µM. In some embodiments, the dNTP concentration in a reaction is 2-10 µM, 2-15 µM, 2-20 µM, 2-25 µM, 2-30 µM, 2-35 µM, 2-40 µM, 2-45 µM, 2-50 µM, 2-55 µM, 2-60 µM, 2-65 µM, 2-70 µM, 2-75 µM, 2-80 µM, 2-85 µM, 2-90 µM, 2-95 µM, 2-100 µM, 2-110 µM, 2-120 µM, 2-130 µM, 2-140 µM, 2-150 µM, 2-160 µM, 2-170 µM, 2-180 µM, 2-190 µM, 2-200 µM, 2-250 µM, 2-300 µM, 2-350 µM, 2-400 µM, 2-450 µM, 2-500 µM, 2-600 µM, 2-700 µM, 2-800 µM, 2-900 µM or 2-1000 µM. For example, the dNTP concentration in a reaction may be 2 µM, 5 µM, 10 µM, 15 µM, 20 µM, 25 µM, 30 µM, 35 µM, 40 µM, 45 µM, 50 µM, 55 µM, 60 µM, 65 µM, 70 µM, 75 µM, 80 µM, 85 µM, 90 µM, 95 µM, 100 µM, 105 µM, 110 µM, 115 µM, 120 µM, 125 µM, 130 µM, 135 µM, 140 µM, 145 µM, 150 µM, 155 µM, 160 µM, 165 µM, 170 µM, 175 µM, 180 µM, 185 µM, 190 µM, 195 µM or 200 µM. In some embodiments, the dNTP concentration in a reaction is 10-20 µM, 10-30 µM, 10-40 µM, 10-50 µM, 10-60 µM, 10-70 µM, 10-80 µM, 10-90 µM or 10-100 µM.

In some embodiments, dNTP variants are used. For example, molecular motor systems may use hot start/clean amp dNTPs, phosphorothioate dNTPs, or fluorescent dNTPs. Other dNTP variants may be used.

In some embodiments, molecular motors may be used for protein "fingerprinting," based on identification of individual protein molecules at the single-molecule level or of purified protein samples. The sequence information of proteins may be transformed into the sequence information of nucleic acids, which can then be recorded and reported by molecular crawlers, for example.

Protein fingerprinting is achieved, in some embodiments, by the following method (FIG. 40). (1) Protein molecules are attached to a surface and denatured and stretched. Protein molecules can be fixed on a surface by N-terminal or C-terminal specific chemical coupling methods. The surface-bound protein molecules can be denatured by common denaturants such as urea or sodium dodecyl sulfate, and can be stretched by applying external forces, e.g. by attaching a magnetic bead at the end far from the surface and applying magnetic field, or by using an electrically charged particle and electric field in a similar fashion. (2) Amino acid residues are specifically labeled by DNA strands containing a unique identifier. Chemical coupling between DNA and amino acid residues can be accomplished through amino-acid-specific chemical modification methods. For example, lysine residues can be modified with NHS-ester chemistry and cysteine residues can selectively interact with the maleimide group. DNA strands bound to amino acids can either just encode the identity information of the target amino acids, or also include unique molecular information for the specific site (e.g., by randomized sequences). (3) Molecular crawlers inspect the labeled sites and record the sequence information. Molecular crawlers operate based on a principle that allows downstream molecular components to be synthesized in situ in a programmed fashion, copying the information from the target molecules. Swarms of molecular crawlers roam around the space, and examine and report quantitative and geometric information of the molecular landscape in a massively parallel fashion. Multiple crawlers can act on the same target and generate partially redundant records. (4) Records are released and collected. Records can be released by in situ synthesis of a complementary strand, or by heat-mediated dehybridization. (5) Retrieved records are analyzed by polymerase chain reaction and gel electrophoresis or by next-generation sequencing. (6) The redundant and partially overlapping sequence information from records is used to reconstruct the sequence of the labeled amino acids. The labeled amino acids represent a subset of the full amino acid sequence of the target protein. This sub-sequence information is then compared and matched to the library of all genetically identified protein-coding sequences from whole genome sequencing, and the identity of the protein can thus be revealed.

Molecular Rulers

Biological research requires tools that can report quantitative, sensitive and systems-level information about molecular interactions. These tools must deal with the sheer number and variety of such interactions while also being capable of reporting interactions for long periods of time at the level of single molecules. Also provided here are molecular recording systems, referred to as "molecular rulers," which record nanoscale distances between target molecules by recording distance information within DNA molecules (FIGS. 31A-31B). The length of the produced DNA record directly corresponds to the distance being measured. In addition, each DNA record encodes the identity of the target molecules as part of its sequence. One round of record production proceeds as follows (see FIG. 34B): (a) Targets are seeded with precursors of DNA records. (b) Precursors grow with the aid of a strand displacement polymerase and catalytic molecules (e.g., catalytic hairpins), until they meet a partner nucleic acid. Partners hybridize and extend into records, each using the other as a template. (c) Records are released and the targets are reset, enabling further rounds of recording. Multiple rounds of recording result in records reporting distances with multiple neighbors and also changes/differences in distance.

Distances are encoded in the length of the DNA records (unary encoding), which are produced autonomously, and multiple records are produced for each target pair. Molecular rulers can keep track of changing distances and reports a distance distribution (super-resolution fitting). Read-out of the records produced is reported through gel electrophoresis, making it accessible to almost any research laboratory.

The molecular ruler can record distances in a solution of target molecules, or in solid-phase or in situ. Molecular rulers enable almost any lab to make molecular distance measurements by using conventional and inexpensive reagents and instruments. Since the output is in the form of DNA molecules, which can concisely encode a lot of information, the technique has massive multiplexing capability. Depending on particular needs, the output can be read with quick and convention assays, such as gel electrophoresis, or one can leverage the high throughput and single molecule capabilities of next-generation sequencing. These features enable the molecular ruler technology provided herein, for example, to assay protein interactions, study protein complex assembly and reveal chromosome conformation.

Molecular rulers, in some embodiments, comprise a plurality of free (unbound) catalytic molecules (described above) that interact with catalytic molecules bound to target biomolecules. These interactions are initiated by primers present in a molecular ruler reaction and are mediated by displaced elongation products (output primers in one cycle that function as input primers in a subsequence cycle. An example of a molecular ruler system is depicted in FIGS. 36A-36H.

Figure 36A:
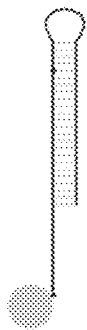
Figure 36A:
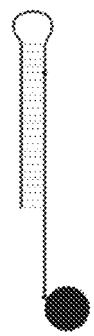
Figure 36B:
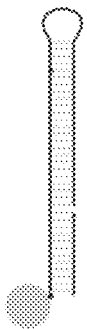
Figure 36B:
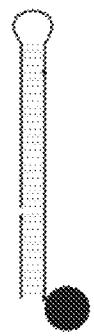
Figure 36C:
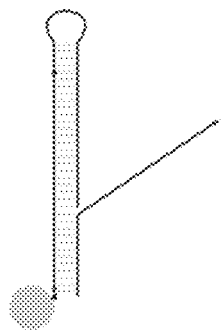
Figure 36C:
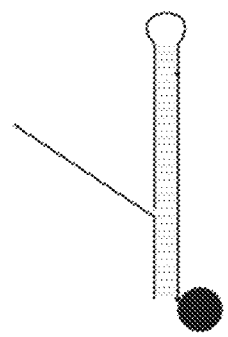
Figure 36D:
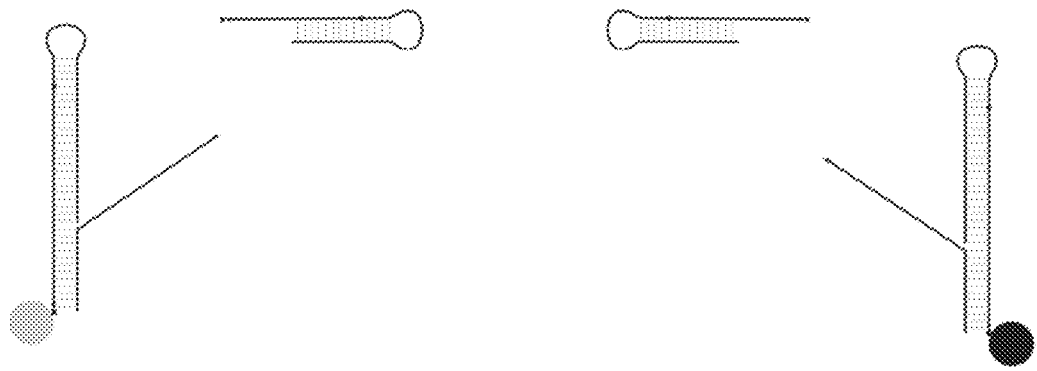
Figure 36E:
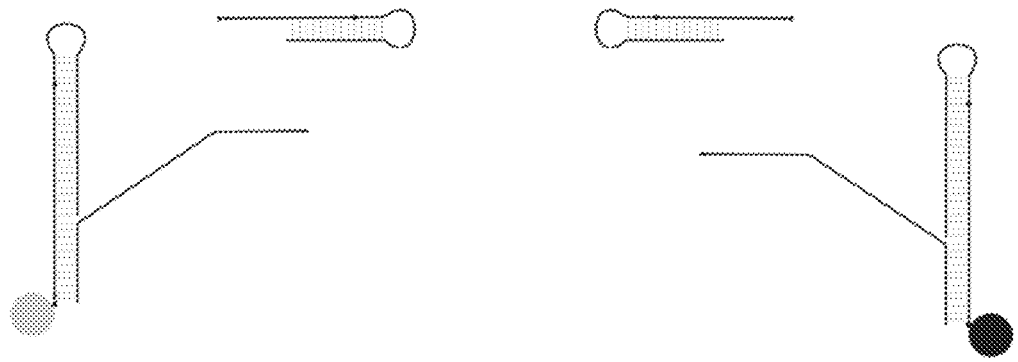
Figure 36F:
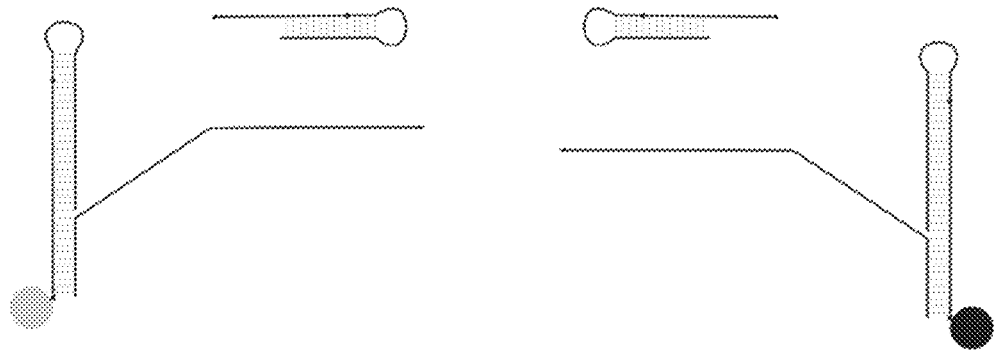
Figure 36G:
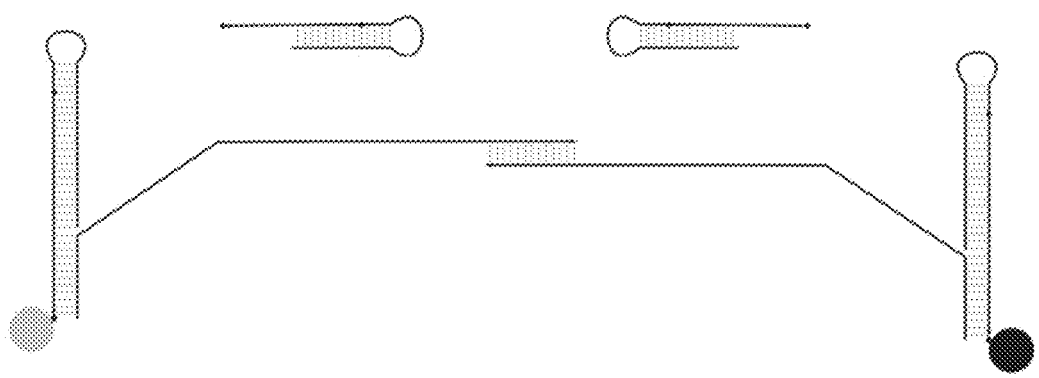
Figure 36H:
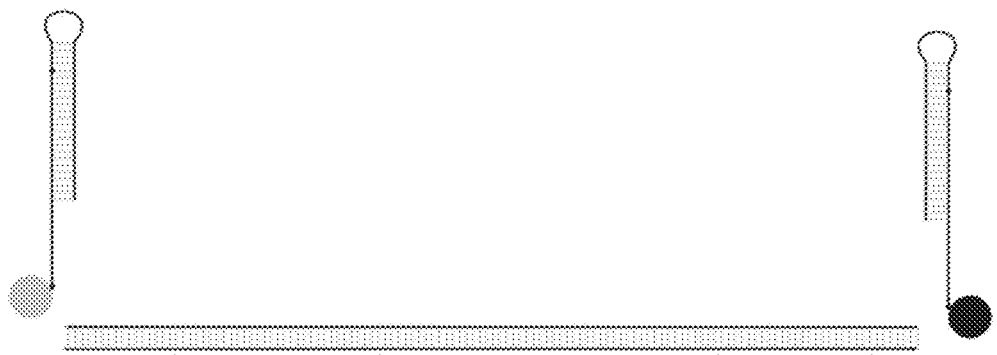

Each target biomolecule (gray circle and black circle) is linked to a catalytic molecule (a hairpin in this example) (FIG. 36A). The reaction also includes a primer that binds to a toehold domain of one of the catalytic molecules, and another primer that binds to the toehold domain of the other catalytic molecule (FIG. 36B). Binding of the primers to the toehold domains, in the presence of strand displacement polymerase and dNTPs, initiates the elongation process for each molecule. The primers are extended through the paired domains, disrupting base pairing in the paired domain. The displaced strand competes with the extension product to re-form the original paired domain (FIG. 36C), and the displaced extension product then serves as a primer for binding to additional free catalytic molecules present in the reaction (FIG. 36D). Binding of the displaced extension product to a free catalytic molecule (FIG. 36E) initiates polymerization through the paired domain of the free catalytic molecule and subsequent displacement of the further extended product (now containing information (DNA) from both the catalytic molecule bound to the biomolecule and information (DNA) from the free catalytic molecule (FIG. 36F). This process continues with other free catalytic molecules in the reaction, with each cycle adding a new piece of information to polymers growing the catalytic molecules linked to the biomolecules, until the two polymers meet and bind to each other (FIG. 36G). At this point polymerization proceeds through the length of the polymers to form a double-stranded nucleic acid record of all the molecular ruler interactions (FIG. 36H). The length of the nucleic acid record corresponds to the distance between the two biomolecules.

FIG. 37A shows another example of a molecular ruler recording a distance between two ends of a double stranded DNA rod. DNA sequence domains are denoted as letters, sometimes with subscripts (for example s, b, a1 etc.). A '*' symbol indicates the sequence complement of a domain (for example, r* is the sequence complement of r). The recording proceeds autonomously but can be conceptually understood as occurring in four steps. (1) Seed: Precursors hybridize to the DNA rod. (2) Activate: Precursors copy a barcode sequence (a1 or a2 in this example) and an activation domain (r r r or r* r* r*) with the aid of a strand displacing polymerase (e.g., BST Large Fragment) and dNTPs. They are stopped by a 'stopping sequence' (here s or s*). A stopping sequence is a stretch of one or more DNA bases/nucleotides (e.g., GOG) without corresponding nucleotides (e.g. dGTPs) supplied in the solution. Thus, they are able to stop the polymerase from copying further nucleotides. Other molecules that terminate polymerization may be used. (3) Grow: The activation domain (here r r r and r* r* r*) allows the precursors to interact with catalytic hairpins to repeatedly add a sequence domain (here r and r*). (4A) Release: When the precursors grow to a sufficient length they can meet each other and hybridize through complementary domains (here r and r*). Then the polymerase can extend them, each using the other as a template, until they are released into solution. The released records are a measure of the distance between the ends of the DNA rod. (4B) Reset: The DNA rod can now seed further precursors and produce more records, resulting in repeated measurements of distance.

FIGS. 37B and 37C show more details of an example of a growth step (Step 3 in FIG. 37A). In a growth step, a short sequence domain (r or r*) is repeatedly and autonomously added to the end of an activated precursor molecule. The activated precursor (a1 r r r and a2 r* r* r* in FIG. 37A) hybridizes to the toehold of the catalytic growth hairpin. The sequence is extended by a single domain (r or r*) with the aid of a strand displacing polymerase and dNTPs. They are stopped from further extension by a stop sequence (x). At this point the newly copied domain can be displaced from the catalytic hairpin. The short toehold domain (r r r or r* r* r*) spontaneously dissociates from the complex. The dissociated activated precursor molecule can now again take part in a growth step via its terminal three domains (r r r or r* r* r*).

Molecular rulers are a variation on the catalytic molecules (e.g., catalytic hairpin molecules) described above. The length of a molecular ruler (e.g., the nucleic acid molecule bound to a target biomolecule) may vary. In some embodiments, a molecular ruler has a length of 25-300 nucleotides. For example, a molecular ruler may have a length of 25-250, 25-200, 25-150, 25-100, 25-50, 50-300, 50-250, 50-200, 50-150 or 50-100 nucleotides. In some embodiments, a molecular ruler has a length of 30-50, 40-60, 50-70, 60-80, 70-90, 80-100, 100-125, 100-150 or 100-200 nucleotides. In some embodiments, a molecular ruler has a length of 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 nucleotides. A molecular ruler, in some embodiments, is longer than 300 nucleotides, or shorter than 25 nucleotides.

A "toehold domain," discussed above, refers to an unpaired sequence of nucleotides located at the 3' end of the molecular ruler and is complementary to (and binds to) a nucleotide sequence of a primer (or primer domain of a primer). The length of a toehold domain may vary. In some embodiments, a toehold domain has a length of 5-40 nucleotides. For example, a toehold domain may have a length of 2-35, 2-30, 2-25, 2-20, 2-15, 2-10, 5-35, 5-30, 5-25, 5-20, 5-15, 5-10, 10-40, 10-35, 10-30, 10-25, 10-20, 10-15, 15-40, 15-35, 15-30, 15-25, 15-20, 20-40, 20-35, 20-30, 20-25, 25-40, 25-35, 25-30, 30-40, 30-35 or 35-40 nucleotides. In some embodiments, a toehold domain has a length of 5, 10, 15, 20, 25, 30, 35 or 40 nucleotides. In some embodiments, a toehold domain has a length of 10, 11, 12, 13, 14, 15, 16, 17, 18, 19, 20, 21, 22, 23, 24 or 25 nucleotides. A toehold domain, in some embodiments, is longer than 40 nucleotides, or shorter than 5 nucleotides.

A "paired domain" of a molecular ruler refers to a paired sequence of nucleotides (e.g., Watson-Crick nucleobase pairing) located adjacent to (and 5 from) the unpaired toehold domain of a molecular ruler. The paired domain of a molecular ruler is formed by base pairing between domain(s) of a template strand and domain(s) of a displacement strand, or by intramolecular base pairing between domains of the same nucleic acid strand (to form a hairpin structure). The length of a paired domain may vary. In some embodiments, a paired domain has a length of 5-40 nucleotides. For example, a paired domain may have a length of 5-35, 5-30, 5-25, 5-20, 5-15, 5-10, 10-40, 10-35, 10-30, 10-25, 10-20, 10-15, 15-40, 15-35, 15-30, 15-25, 15-20, 20-40, 20-35, 20-30, 20-25, 25-40, 25-35, 25-30, 30-40, 30-35 or 35-40 nucleotides. In some embodiments, a paired domain has a length of 5, 10, 15, 20, 25, 30, 35 or 40 nucleotides. In some embodiments, a paired domain has a length of 10, 11, 12, 13, 14, 15, 16, 17, 18, 19, 20, 21, 22, 23, 24 or 25 nucleotides. A paired domain, in some embodiments, is longer than 40 nucleotides, or shorter than 5 nucleotides.

In some embodiments, extension of a primer (bound to a primer-binding site) by a strand displacement polymerase is terminated by the presence of a molecule or modification in the molecular ruler that terminates polymerization. Thus, in some embodiments, molecular rulers of the present disclosure comprise a molecule or modification that terminates polymerization. A molecule or modification that terminates polymerization ("stopper") is typically located in a paired domain on the template strand of a molecular ruler such that polymerization terminates extension of the primer through the paired domain. In some embodiments, the molecule that terminate polymerization is a synthetic non-DNA linker, for example, a triethylene glycol spacer, such as the Int Spacer 9 (iSp9) or Spacer 18 (Integrated DNA Technologies (IDT)). It should be understood that any non-native linker that terminates polymerization by a polymerase may be used as provided herein. Other non-limiting examples of such molecules and modifications include a three-carbon linkage (/iSpC3/) (IDT). ACRYDITE™ (IDT), adenylation, azide, digoxigenin (NHS ester), cholesteryl-TEG (IDT), I-LINKER™ (IDT), and 3-cyanovinylcarbazole (CNVK) and variants thereof. Typically, but not always, short linkers (e.g., iSp9) lead to faster reaction times.

In some embodiments, the molecule that terminates polymerization is a single or paired non-natural nucleotide sequence, such as iso-dG and iso-dC (IDT), which are chemical variants of cytosine and guanine, respectively. Iso-dC will base pair (hydrogen bond) with Iso-dG but not with dG. Similarly, Iso-dG will base pair with Iso-dC but not with dC. By incorporating these nucleotides in a pair on opposite sides of the hairpin, at the stopper position, the polymerase will be halted, as it does not have a complementary nucleotide in solution to add at that position.

In some embodiments, the efficiency of performance of a "stopper" modification is improved by lowering dNTP concentrations (e.g., from 200 µM) in a reaction to 100 µM, 10 µM, 1 µM, or less.

Inclusion of a molecule or modification that terminates polymerization often creates a "bulge" in a double-stranded domain of catalytic molecule (e.g., a stem domain for hairpin structures), because the molecule or modification is not paired. Thus, in some embodiments, molecular rulers are designed to include, opposite the molecule or modification, a single nucleotide (e.g., thymine), at least two of same nucleotide (e.g., a thymine dimer (TT) or trimer (TTT)), or an non-natural modification.

Molecular ruler reaction systems also include primers, referred to as input primers or output primers. Primers are described elsewhere herein.

A complete "step" of a molecular ruler reaction is depicted in FIGS. 37A-37C.

In some embodiments, a primer or primer domain (the nucleotide sequence that binds to the toehold domain of a molecular ruler) has a length of 10-50 nucleotides. For example, a primer or primer domain may have a length of 10-45, 10-40, 10-35, 10-30, 10-25, 10-20, 10-15, 15-50, 15-45, 15-40, 15-35, 15-30, 15-25, 15-20, 20-50, 20-45, 20-40, 20-35, 20-30, 20-25, 25-50, 25-45, 25-40, 25-35, 25-30, 30-50, 30-45, 30-40, 30-35, 35-50, 35-45, 35-40, 40-50, 40-45 or 45-50 nucleotides. In some embodiments, a primer or primer domain has a length of 10, 15, 20, 25, 30, 35, 40, 45 or 50 nucleotides. In some embodiments, a primer or primer domain has a length of 15, 16, 17, 18, 19, 20, 21, 22, 23, 24 or 25 nucleotides. A primer or primer domain, in some embodiments, is longer than 50 nucleotides, or shorter than 10 nucleotides. It should be understood that the full length of a primer depends, at least in part, on the number and length of appended (polymerized) sequences, which depends on the number and length of free (not linked to a biomolecule such as a protein) catalytic molecules present in a reaction as well as the distance between to target biomolecules to which catalytic molecules are linked.

A primer, as provided herein, may be linked to (labeled with) a detectable molecule (e.g., a molecule that emits a detectable signal, such as a fluorescent or chemiluminescent signal). In some embodiments, the label is a fluorophore. A primer linked to a fluorophore or other fluorescent/chemiluminescent molecule is referred to simply as a "fluorescent primer." Examples of fluorophores that may be used herein include, without limitation, hydroxycoumarin, methoxycoumarin, Alexa fluor, aminocoumarin, Cy2, FAM, Alexa fluor 405, Alexa fluor 488, Fluorescein FITC, Alexa fluor 430, Alexa fluor 532, HEX, Cy3, TRITC, Alexa fluor 546, Alexa fluor 555, R-phycoerythrin (PE), Rhodamine Red-X, Tamara, Cy3.5 581, Rox, Alexa fluor 568, Red 613, Texas Red, Alexa fluor 594, Alexa fluor 633, Allophycocyanin, Alexa fluor 647, Cy5, Alexa fluor 660, Cy5.5, TruRed, Alexa fluor 680, Cy7 and Cy7.5. Other fluorophores and molecules that emit a detectable signal are encompassed by the present disclosure.

In some embodiments, a detectable molecule is linked to the molecular ruler rather than the primer.

In some embodiments, a molecular ruler is linked to a biomolecule. Biomolecules include, for example, nucleic acids (e.g., DNA or RNA) and proteins. A biomolecule may be a therapeutic, prophylactic, diagnostic or imaging molecule. In some embodiments, a biomolecule is a disease-related or drug-related biomolecule, such as a cancer-related gene or protein, or an FDA-approved or potential drug target. In some embodiments, a biomolecule is an enzyme, an antigen, a receptor, a ligand, a membrane protein, a secreted protein, or a transcription factor.

Molecular ruler reactions require the use of a polymerase. In some embodiments, the polymerase is a DNA polymerase (DNAP), such as a DNA polymerase having DNA strand displacement activity. "Strand displacement" describes the ability to displace downstream DNA encountered during synthesis. Examples of polymerases having DNA strand displacement activity that may be used as provided herein include, without limitation, phi29 DNA polymerase (e.g., NEB #M0269), Bst DNA polymerase, large fragment (e.g., NEB #M0275), or Bsu DNA polymerase, large fragment (e.g., NEB #M0330). Other polymerases having strand displacement activity may be used. In some embodiments, the polymerase is a RNA polymerase.

In some embodiments, the polymerase is phi29 DNA polymerase. In such embodiments, the reaction conditions may be as follows: 1× reaction buffer (e.g., 50 mM Tris-HCl, 10 mM $MgCl_2$, 10 mM $(NH_4)SO_4$, 4 mM DTT) supplement with purified bovine serum albumin (BSA), pH 7.5, incubated at 30° C.

In some embodiments, the polymerase is Bst DNA polymerase, large fragment. In such embodiments, the reaction conditions may be as follows: 1× reaction buffer (e.g., 20 mM Tris-HCl, 10 mM $(NH_4)_2SO_4$, 10 mM KCl, 2 mM $MgSO_4$, 0.1% TRITON® X-100), pH 8.8, incubated at 65° C.

In some embodiments, the polymerase is Bsu DNA polymerase. In such embodiments, the reaction conditions may be as follows: 1× reaction buffer (e.g., 50 mM NaCl, 10 mM Tris-HCl, 10 mM $MgCl_2$, 1 mM DTT), pH 7.9, incubated at 37° C.

The concentration of primer, catalytic molecules and dNTPs in a reaction system may be varied depending, for example, on the particular application and kinetics required for that particular application.

The concentration of primer in a reaction may be, for example, 10 nM to 1000 nM. In some embodiments, the primer concentration in a reaction is 10-20, 10-30, 10-40, 10-50, 10-60, 10-70, 10-80, 10-90, 10-100, 10-125, 10-150, 10-200, 25-50, 25-75, 25-100, 25-150, 25-200, 50-75, 50-100, 50-150 or 50-200 nM. In some embodiments, the primer concentration in a reaction is 100-200, 100-300, 100-400, 100-500, 100-600, 100-70, 100-800, 100-900 or 100-1000 nM. In some embodiments, the primer concentration in a reaction is 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195 or 200 nM. In some embodiments, the primer concentration in a reaction is 100, 200, 300, 400, 500, 600, 700, 800, 900 or 1000 nM. The concentration of primer in a reaction may be less than 10 nM or greater than 1000 nM.

The concentration of molecular rulers and/or catalytic molecules in a reaction may be, for example, 5 nM to 1000 nM. In some embodiments, the molecular ruler and/or catalytic molecule concentration in a reaction is 5-10, 5-20, 5-30, 5-40, 5-50, 5-60, 5-70, 5-80, 5-90, 5-100, 5-125, 5-150, 5-200, 10-50, 10-75, 10-100, 10-150, 10-200, 25-75, 25-100, 25-125 or 25-200 nM. In some embodiments, the molecular ruler and/or catalytic molecule concentration in a reaction is 10-200, 10-300, 10-400, 10-500, 10-600, 10-70, 10-800, 10-900 or 10-100 nM. In some embodiments, the molecular ruler and/or catalytic molecule concentration in a reaction is 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195 or 200 nM. In some embodiments, the molecular ruler and/or catalytic molecule concentration in a reaction is 10, 20, 30, 40, 50, 60, 70, 80, 90 or 100 nM. The concentration of molecular ruler and/or catalytic molecule in a reaction may be less than 5 nM or greater than 1000 nM.

The ratio of primer to molecular rulers and/or catalytic molecules in reaction may be 2:1 to 100:1. In some embodiments, the ratio of primer to molecular ruler and/or catalytic molecule is 2:1, 3:1, 4:1, 5:1, 6:1, :1, 8:1, 9:1, 10:1, 11:1, 12:1, 13:1, 14:1, 15:1, 16:1, 17:1, 18:1, 19:1 or 20:1. In some embodiments, the ratio of primer to molecular ruler and/or catalytic molecule is 30:1, 40:1, 50:1, 60:1, 70:1, 80:1 or 90:1.

The number of different molecular rulers and/or catalytic molecules in a reaction in non-limiting. A reaction may comprise $1-10^{10}$ different molecular rulers and/or catalytic molecules (each with a specific toehold domain sequence, for example). In some embodiments, a molecular ruler reaction comprises 1-10, $1-10^2$, 1-10, $1-10^4$, $1-10^5$, $1-10^6$, $1-10^7$, 1-108, $1-10^9$, $1-10^{10}$, or more, different molecular rulers and/or catalytic molecules. In some embodiments, a reaction comprises 1-5, 1-10, 1-15, 1-20, 1-25, 1-30, 1-35, 1-40, 1-45, 1-50, 1-55, 1-60, 1-65, 1-70, 1-75, 1-80, 1-85, 1-90, 1-95, 1-100, 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 10-15, 10-20, 10-25, 10-30, 10-35, 10-40, 10-45, 10-50, 10-55, 10-60, 10-65, 10-70, 10-75, 10-80, 10-85, 10-90, 10-95 or 10-100 different molecular rulers and/or catalytic molecules. In some embodiments, a reaction comprises 1, 2, 3, 4, 5, 6, 7, 8, 9, 10, 11, 12, 13, 14, 15, 16, 17, 28, 19, 20, 21, 22, 23, 24 or 25 different molecular rulers and/or catalytic molecules. Molecular rulers are different from each other if their toehold domains differ from each other, for example.

The kinetics of a reaction may be controlled by varying temperature, time, buffer/salt conditions, and deoxyribonucleotide triphosphate (dNTP) concentrations, for example. Polymerases, like most enzymes, are sensitive to many buffer conditions, including ionic strength, pH and types of metal ions present (e.g., sodium ions vs. magnesium ions). Thus, the temperature at which a reaction is performed may vary from, for example, 4° C. to 65° C. (e.g., 4° C., 25° C., 37° C., 42° C. or 65° C.). In some embodiments, the temperature at which a reaction is performed is 4-25° C. 4-30° C., 4-35° C., 4-40° C., 4-45° C., 4-50° C., 4-55° C., 4-60° C., 10-25° C., 10-30° C., 10-35° C., 10-40° C., 10-45° C., 10-50° C., 10-55° C., 10-60° C., 25-30° C., 25-35° C., 25-40° C., 25-45° C., 25-50° C., 25-55° C., 25-60° C., 25-65° C., 35-40° C., 35-45° C., 35-50° C., 35-55° C., 35-60° C., or 35-65° C. In some embodiments, a reaction is performed at room temperature, while in other embodiments, a reaction is performed at 37° C.

A reaction may be performed (incubated) for 30 minutes (min) to 24 hours (hr). In some embodiments, a reaction is carried out for 10 min, 35 min, 40 min, 45 min, 50 min, 55 min, 60 min, 1 hr, 2 hr, 3 hr, 4 hr, 5 hr, 6 hr, 7 hr, 8 hr, 9 hr, 10 hr, 11 hr, 12 hr, 18 hr or 24 hr.

The concentration of dNTPs in a reaction may be, for example, 2-1000 µM. In some embodiments, the dNTP concentration in a reaction is 2-10 µM, 2-15 µM, 2-20 µM, 2-25 µM, 2-30 µM, 2-35 µM, 2-40 µM, 2-45 µM, 2-50 µM, 2-55 µM, 2-60 µM, 2-65 µM, 2-70 µM, 2-75 µM, 2-80 µM, 2-85 µM, 2-90 µM, 2-95 µM, 2-100 µM, 2-110 µM, 2-120 µM, 2-130 µM, 2-140 µM, 2-150 µM, 2-160 µM, 2-170 µM, 2-180 µM, 2-190 µM, 2-200 µM, 2-250 µM, 2-300 µM, 2-350 µM, 2-400 µM, 2-450 µM, 2-500 µM, 2-600 µM, 2-700 µM, 2-800 µM, 2-900 µM or 2-1000 µM. For example, the dNTP concentration in a reaction may be 2 µM, 5 µM, 10 µM, 15 µM, 20 µM, 25 µM, 30 µM, 35 µM, 40 µM, 45 µM, 50 µM, 55 µM, 60 µM, 65 µM, 70 µM, 75 µM, 80 µM, 85 µM, 90 µM, 95 µM, 100 µM, 105 µM, 110 µM, 115 µM, 120 µM, 125 µM, 130 µM, 135 µM, 140 µM, 145 µM, 150 µM, 155 µM, 160 µM, 165 µM, 170 µM, 175 µM, 180 µM, 185 µM, 190 µM, 195 µM or 200 µM. In some embodiments, the dNTP concentration in a reaction is 10-20 µM, 10-30 µM, 10-40 µM, 10-50 µM, 10-60 µM, 10-70 µM, 10-80 µM, 10-90 µM or 10-100 µM.

In some embodiments, dNTP variants are used. For example, molecular ruler systems may use hot start/clean amp dNTPs, phosphorothioate dNTPs, or fluorescent dNTPs. Other dNTP variants may be used.

The present disclosure further provides embodiments encompassed by the following numbered paragraphs:

1. A primer exchange reaction (PER) system, comprising:
   (a) an initial catalytic hairpin molecule comprising (i) an unpaired 3' toehold domain, (ii) a paired stem domain formed by intramolecular nucleotide base pairing between a 3' subdomain of the molecule and a 5' subdomain of the molecule, and (iii) a linkage domain;
   (b) an initial primer that is complementary to and binds to the 3' toehold domain; and
   (c) polymerase having strand displacement activity.
2. The PER system of paragraph 1, wherein the linkage domain is a loop domain.
3. The PER system of paragraph 1 or 2 further comprising (d) a second catalytic hairpin molecule comprising (i) an unpaired 3' toehold domain, (ii) a paired stem domain formed by intramolecular nucleotide base pairing between a 3' subdomain of the second hairpin molecule and a 5' subdomain of the second hairpin molecule, and (iii) a loop domain, wherein the 3' toehold domain of the second hairpin molecule is complementary to the 5' subdomain of the initial hairpin molecule.
4. The PER system of paragraph 3 further comprising a second primer comprising nucleotides complementary to nucleotides located in the unpaired 3' toehold domain of the second hairpin molecule.
5. The PER system of any one of paragraphs 1-4 further comprising (e) a third catalytic hairpin molecule comprising (i) an unpaired 3' toehold domain, (ii) a paired stem domain formed by intramolecular nucleotide base pairing between a 3' subdomain of the third hairpin molecule and a 5' subdomain of the third hairpin molecule, and (iii) a loop domain, wherein the 3' toehold domain of the third hairpin molecule is complementary to the 5' subdomain of the second hairpin molecule.
6. The PER system of paragraph 5 further comprising a third primer complementary to the unpaired 3' toehold domain of the third hairpin molecule.
7. The PER system of paragraph 5 or 6 further comprising a plurality of catalytic hairpin molecules, each hairpin molecule comprising (i) an unpaired 3' toehold domain, (ii) a paired stem domain formed by intramolecular nucleotide base pairing between a 3' subdomain of a hairpin molecule of the plurality and a 5' subdomain of a hairpin molecule of the plurality, and (iii) a loop domain, wherein the 3' toehold domain of each hairpin molecule is complementary to the 5' subdomain of one other hairpin molecule of the plurality.
8. The PER system of paragraph 7 further comprising a plurality of primers, each primer complementary to an unpaired 3' toehold domain of one of the hairpin molecules of the plurality.
9. The PER system of any one of paragraphs 1-8, wherein the primer is linked to a detectable molecule.
10. The PER system of any one of paragraphs 1-9, wherein the primer is linked to a biomolecule.
11. The PER system of paragraph 10, wherein the biomolecule is a protein.
12. The PER system of any one of paragraphs 1-11, wherein the polymerase is phi29 DNA polymerase, Bst DNA polymerase or Bsu DNA polymerase.
13. The PER system of any one of paragraphs 1-12 further comprising deoxyribonucleotide triphosphates (dNTPs).
14. A primer exchange reaction (PER) system, comprising:
   (a) an initial catalytic hairpin molecule comprising (i) an unpaired 3' toehold domain, (ii) a paired stem domain formed by intramolecular nucleotide base pairing between a 5' subdomain of the molecule and a 3' subdomain of the molecule, and (iii) a loop domain;
   (b) a second catalytic hairpin molecule comprising (i) an unpaired 3' toehold domain, (ii) a paired stem domain formed by intramolecular nucleotide base pairing between a 3' subdomain of the second hairpin molecule and a 5' subdomain of the second hairpin molecule, and (iii) a linkage domain, wherein the 3' toehold domain of the second hairpin molecule is complementary to the 5' subdomain of the initial hairpin molecule; and
   (c) an initial primer complementary to the unpaired 3' toehold domain of the initial hairpin molecule.

15. The PER system of paragraph 14, wherein the linkage domain is a loop domain.
16. The PER system of paragraph 14 or 15 further comprising a second primer complementary to the unpaired 3' toehold domain of the second hairpin molecule.
17. The PER system of paragraph 14 or 16 further comprising a polymerase having strand displacement activity.
18. The PER system of any one of paragraphs 14-17 further comprising deoxyribonucleotide triphosphates (dNTPs).
19. A primer exchange reaction method, comprising: combining in reaction buffer
    (a) an initial catalytic hairpin molecule comprising (i) an unpaired 3' toehold domain, (ii) a paired stem domain formed by intramolecular nucleotide base pairing between a 3' subdomain of the molecule and a 5' subdomain of the molecule, and (iii) a linkage domain,
    (b) a second catalytic hairpin molecule comprising (i) an unpaired 3' toehold domain, (ii) a paired stem domain formed by intramolecular nucleotide base pairing between a 3' subdomain of the second hairpin molecule and a 5' subdomain of the second hairpin molecule, and (iii) a loop domain, wherein the 3' toehold domain of the second hairpin molecule is complementary to the 5' subdomain of the initial hairpin molecule,
    (c) a primer complementary to the unpaired 3' toehold domain of the initial hairpin molecule,
    (d) a polymerase having strand displacement activity, and
    (e) deoxyribonucleotide triphosphates (dNTPs), thereby forming a reaction mixture; and
    incubating the reaction mixture under conditions that result in nucleic acid polymerization, strand displacement and annealing, for a time sufficient to produce a single-stranded nucleic acid record.
20. The primer exchange reaction of paragraph 19, wherein the linkage domain is a loop domain.
21. A primer exchange reaction, comprising
    (a) contacting an input primer with a catalytic molecule, in the presence of polymerase having strand displacement activity and deoxyribonucleotide triphosphates (dNTPs), wherein the catalytic molecule comprises (i) an unpaired 3' toehold domain and (ii) a paired domain located 5' from the toehold domain that is formed by nucleotide base pairing between a displacement strand and a template strand containing the toehold domain, wherein the input primer is complementary to the 3' toehold domain of the catalytic molecule;
    (b) extending the primer through the paired domain of the catalytic molecule, thereby displacing the displacement strand and forming an extended output primer;
    (c) displacing the extended output primer from the hairpin molecule through intramolecular nucleotide base pairing between the displacement strand and the template strand; and
    (d) contacting the displaced extended output primer of (c) with a second catalytic molecule, in the presence of polymerase having strand displacement activity and dNTPs, wherein the second catalytic molecule comprises (i) an unpaired 3' toehold domain and (ii) a paired domain located 5' from the toehold domain that is formed by nucleotide base pairing between a displacement strand and a template strand containing the toehold domain, and wherein the extended output primer is complementary to the 3' toehold domain of the second catalytic molecule.
22. A method of producing a single-stranded nucleic acid, comprising:
    combining in reaction buffer
    (a) an initial hairpin molecule comprising (i) an unpaired 3' toehold domain, (ii) a paired stem domain formed by intramolecular nucleotide base pairing between a 3' subdomain of the molecule and a 5' subdomain of the molecule, and (iii) a hairpin loop domain,
    (b) a plurality of different hairpin molecules, each hairpin molecule comprising (i) an unpaired 3' toehold domain, (ii) a paired stem domain formed by intramolecular nucleotide base pairing between a 3' subdomain of a hairpin molecule of the plurality and a 5' subdomain of a hairpin molecule of the plurality, and (iii) a loop domain, wherein the 3' toehold domain of each hairpin molecule is complementary to the 5' subdomain of one other hairpin molecule of the plurality;
    (c) an initial primer complementary to the 3' toehold domain of the initial hairpin molecule,
    (d) a polymerase having strand displacement activity, and
    (e) deoxyribonucleotide triphosphates (dNTPs), thereby forming a reaction mixture; and
    incubating the reaction mixture under conditions that result in nucleic acid polymerization, strand displacement and annealing, for a time sufficient to produce a single-stranded nucleic acid record that is longer than the initial primer.
23. The method of paragraph 22, wherein the single-stranded nucleic acid produced in (e) comprises a concatemer of nucleotide domains complementary to stem domains of the hairpin molecules of the plurality.
24. The method of paragraph 22 or 23, wherein the single-stranded nucleic acid produced in (e) comprises domains of self-complementarity.
25. The method of paragraph 24 further comprising incubating the reaction mixture under conditions that result in folding of the single-stranded nucleic acid produced in (e) through intramolecular nucleotide base pairing between the domains of self-complementarity.
26. The method of any one of paragraphs 22-25 further comprising incubating the reaction mixture in the presence of nucleic acid staple strands under conditions that result in folding of the single-stranded nucleic acid produced in (e) through nucleotide base pairing between domains of the single-stranded nucleic acid and the nucleic acid staple strands.
27. A cell comprising the PER system of any one of paragraphs 1-13.
28. The cell of paragraph 27, wherein the cell is a prokaryotic cell or a eukaryotic cell.
29. The cell of paragraph 28, wherein the cell is a mammalian cell.
30. A vector comprising at least two nucleic acids, each encoding a catalytic hairpin molecule that comprises (i) an unpaired 3' toehold domain, (ii) a paired stem domain formed by intramolecular nucleotide base pairing between a 3' subdomain of a catalytic hairpin molecule and a 5' subdomain of the same catalytic hairpin molecule, and (iii) a loop domain.

31. The vector of paragraph 30, wherein the vector encodes at least three, at least four, or at least five nucleic acids, each encoding a catalytic hairpin molecule that comprises (i) an unpaired 3' toehold domain, (ii) a paired stem domain formed by intramolecular nucleotide base pairing between a 3' subdomain of a catalytic hairpin molecule and a 5' subdomain of the same catalytic hairpin molecule, and (iii) a loop domain.

32. A cell comprising the vector of paragraph 30 or 31.

33. The cell of paragraph 32 further comprising an initial primer that is complementary to and binds to the 3' toehold domain of a catalytic molecule.

34. The cell of paragraph 32 or 33 further comprising a polymerase having strand displacement activity.

35. A composition, comprising:
   (a) a catalytic hairpin molecule comprising (i) an unpaired 3' toehold domain, (ii) a paired stem domain formed by intramolecular nucleotide base pairing between a 3' subdomain of the molecule and a 5' subdomain of the molecule, and (iii) a linkage domain, wherein the domains of (a)(i) and (a)(ii) form tandem repeat sequences;
   (b) at least one other catalytic hairpin molecule comprising (i) a 3' toehold domain, (ii) a paired stem domain formed by intramolecular nucleotide base pairing between a 3' subdomain of the molecule and a 5' subdomain of the molecule, and (iii) a linkage domain, wherein the domains of (b)(i) and (b)(ii) form tandem repeat sequences interrupted by a signal sequence, and wherein the 3' toehold domain of (b)(i) is irreversibly bound to a protector strand; and
   (c) a nucleic acid primer comprising a domain complementary to the 3' toehold domain of the catalytic hairpin molecule of (a) and complementary to the 3' toehold domain of the catalytic hairpin molecule of (b).

36. The composition of paragraph 35, wherein the linkage domain of (a)(iii) and/or (b)(iii) is a loop domain.

37. The composition of paragraph 35, wherein the linkage domain of (a)(iii) and/or (b)(iii) comprises at least one covalently crosslinked nucleotide.

38. The composition of paragraph 35, wherein the linkage domain is a stable paired domain having a length of at least 10 nucleotides.

39. The composition of any one of paragraphs 35-38, wherein the signal sequence has a length of 2-20 nucleotides.

40. The composition of any one of paragraphs 35-39, wherein the signal sequence is barcoded specifically to a target molecule.

41. The composition of any one of paragraphs 35-40, wherein the primer comprises an experiment-specific barcode.

42. The composition of any one of paragraphs 35-41, wherein the protector strand is linked to the 3' toehold domain of the at least one other catalytic hairpin molecule of (b), optionally through a loop domain.

43. The composition of any one of paragraphs 35-42 further comprising a target molecule.

44. The composition of paragraph 43, wherein the target molecule is a nucleic acid.

45. The composition of paragraph 44, wherein the nucleic acid is a single-stranded nucleic acid or a double-stranded nucleic acid.

46. The composition of paragraph 43, wherein the target molecule is a biomolecule selected from proteins, peptides, lipids, carbohydrates, fats, and small molecules having a molecular weight of less than 900 Daltons.

47. The composition of any one of paragraphs 43-46, wherein the protector strand is capable of binding to the target molecule.

48. The composition of paragraph 47, wherein the target molecule comprises or is linked to a nucleotide sequence that is complementary to the protector strand.

49. The composition of any one of paragraphs 35-48 further comprising a polymerase having strand displacement activity.

50. A method of detecting a target molecule, comprising combining in reaction buffer containing a target molecule, strand displacement polymerase, and deoxyribonucleotide triphosphates (dNTPs):
   (a) a catalytic hairpin molecule comprising (i) an unpaired 3' toehold domain, (ii) a paired stem domain formed by intramolecular nucleotide base pairing between a 3' subdomain of the molecule and a 5' subdomain of the molecule, and (iii) a linkage domain, wherein the domains of (a)(i) and (a)(ii) form tandem repeat sequences;
   (b) at least one other catalytic hairpin molecule comprising (i) a 3' toehold domain, (ii) a paired stem domain formed by intramolecular nucleotide base pairing between a 3' subdomain of the molecule and a 5' subdomain of the molecule, and (iii) a linkage domain, wherein the domains of (b)(i) and (b)(ii) form tandem repeat sequences interrupted by a signal sequence, and wherein the 3' toehold domain of (b)(i) is irreversibly bound to a protector strand that is capable of binding to the target molecule; and
   (c) a nucleic acid primer comprising a domain complementary to the 3' toehold domain of the catalytic hairpin molecule of (a) and complementary to the 3' toehold domain of the catalytic hairpin molecule of (b)
   incubating the reaction mixture under conditions that result in nucleic acid polymerization, strand displacement and annealing, for a time sufficient to produce a single-stranded nucleic acid record that is longer than the initial primer and comprises at least one of the signal sequences.

51. A method of measuring time between molecular events, comprising:
   combining in reaction buffer
      (a) an initial catalytic hairpin molecule comprising (i) an unpaired 3' toehold domain, (ii) a paired stem domain formed by intramolecular nucleotide base pairing between a 3' subdomain of the molecule and a 5' subdomain of the molecule, and (iii) a hairpin loop domain,
      (b) a plurality of different catalytic hairpin molecules, each hairpin molecule comprising (i) an unpaired 3' toehold domain, (ii) a paired stem domain formed by intramolecular nucleotide base pairing between a 3' subdomain of a hairpin molecule and a 5' subdomain of a hairpin molecule, and (iii) a loop domain, wherein the 3' toehold domain of each hairpin molecule is complementary to the 5' subdomain of one other hairpin molecule of the plurality;
      (c) an initial primer complementary to the unpaired 3' toehold domain of the initial hairpin molecule,
      (d) a polymerase having strand displacement activity, and (e) deoxyribonucleotide triphosphates (dNTPs), thereby forming a reaction mixture;
exposing the reaction mixture to a first molecular event;
incubating the reaction mixture under conditions that result in nucleic acid polymerization, strand displacement and annealing, for a time sufficient to produce a single-stranded nucleic acid record; and
exposing the reaction mixture to a second molecular event.

52. The method of paragraph 51, wherein the first molecular event initiates DNA polymerization.

53. The method of paragraph 51 or 52, wherein the second molecular event terminates DNA polymerization.

54. The method of any one of paragraphs 51-53 further comprising determining an interval of time between the first molecular event and the second molecular event based on length of the single-stranded nucleic acid produced.

55. A primer exchange reaction (PER) system, comprising:
(a) an initial catalytic molecule comprising an unpaired 3' toehold domain and a paired domain located 5' from the toehold domain and formed by nucleotide base pairing between a displacement strand and a template strand containing the toehold domain;
(b) an initial primer complementary to the unpaired 3' toehold domain; and
(c) polymerase having strand displacement activity.

56. The PER system of paragraph 55 further comprising a second catalytic molecule comprising an unpaired 3' toehold domain and a paired domain located 5' from the toehold domain and formed by nucleotide base pairing between a displacement strand and a template strand that comprises the toehold domain, wherein the 3' toehold domain of the second catalytic molecule is complementary to the displacement strand of the paired domain of the initial catalytic molecule.

57. A molecular motor system, comprising:
(a) an initial nucleic acid molecule comprising (i) an unpaired 3' toehold domain and (ii) a paired domain located 5' from the toehold domain that is formed by nucleotide base pairing between a displacement strand and a template strand containing the toehold domain;
(b) a second nucleic acid molecule comprising (i) an unpaired 3' toehold domain and (ii) a paired domain located 5' from the toehold domain that is formed by nucleotide base pairing between a displacement strand and a template strand containing the toehold domain, wherein the unpaired 3' toehold domain of the second nucleic acid molecule is complementary to the displacement strand of the initial nucleic acid molecule; and
(c) a primer complementary to nucleotides located in the unpaired 3' toehold domain of the initial nucleic acid molecule.

58. The molecular motor system of paragraph 57 further comprising a polymerase having strand displacement activity.

59. The molecular motor system of paragraphs 57 or 58, wherein the paired domain of the initial nucleic acid molecule comprises a molecule that terminates polymerization.

60. The molecular motor system of any one of paragraphs 57-59, wherein the paired domain of the second nucleic acid molecule comprises a molecule that terminates polymerization.

61. The molecular motor system of any one of paragraphs 57-59, wherein the 3' toehold domain of the second nucleic acid molecule comprises a 3' molecule that stops polymerization.

62. The molecular motor system of any one of paragraphs 57-61 further comprising a plurality of nucleic acid molecules, each molecule comprising (i) an unpaired 3' toehold domain and (ii) a paired domain located 5' from the toehold domain that is formed by nucleotide base pairing between a displacement strand and a template strand containing the toehold domain, wherein the unpaired 3' toehold domain of a molecule of the plurality is complementary to a displacement strand of one other nucleic acid molecule of the plurality.

63. The molecular motor system of any one of paragraphs 57-62, wherein at least one of the nucleic acid molecules is attached to a target biomolecule.

64. The molecular motor system of paragraph 63, wherein each of the nucleic acid molecules is attached to a different target biomolecule.

65. A method of recording distances between target biomolecules, comprising:
combining in reaction buffer
(a) an initial nucleic acid molecule comprising (i) an unpaired 3' toehold domain and (ii) a paired domain located 5' from the toehold domain that is formed by nucleotide base pairing between a displacement strand and a template strand containing the toehold domain, wherein the initial nucleic acid molecule is linked to a target biomolecule,
(b) a second nucleic acid molecule comprising (i) an unpaired 3' toehold domain and (ii) a paired domain located 5' from the toehold domain that is formed by nucleotide base pairing between a displacement strand and a template strand containing the toehold domain, wherein the unpaired 3' toehold domain of the second nucleic acid molecule is complementary to the displacement strand of the initial nucleic acid molecule, and wherein the second nucleic acid molecule is linked to a target biomolecule,
(c) a primer complementary to the unpaired 3' toehold domain of the initial nucleic acid molecule,
(d) a polymerase having strand displacement activity, and
(e) deoxyribonucleotide triphosphates (dNTPs), thereby forming a reaction mixture; and
incubating the reaction mixture under conditions that result in nucleic acid polymerization, strand displacement and annealing, for a time sufficient to produce a single-stranded nucleic acid record.

66. The method of paragraph 65, wherein the reaction mixture further comprises a plurality of nucleic acid molecules, each molecule comprising (i) an unpaired 3' toehold domain and (ii) a paired domain located 5' from the toehold domain that is formed by nucleotide base pairing between a displacement strand and a template strand containing the toehold domain, wherein the unpaired 3' toehold domain of a nucleic acid molecule of the plurality is complementary to a displacement strand of one other nucleic acid molecule of the plurality, and wherein each nucleic acid molecule of the plurality is linked to a target biomolecule.

67. A molecular recording system, comprising:
(a) an initial hairpin molecule comprising (i) an unpaired 3' toehold domain, (ii) a paired stem domain formed by intramolecular nucleotide base pairing between a 3' subdomain of the molecule and a 5' subdomain of the molecule, and (iii) a loop domain, wherein the initial hairpin molecule is linked to a target biomolecule;

(b) a second hairpin molecule comprising (i) an unpaired 3' toehold domain, (ii) a paired stem domain formed by intramolecular nucleotide base pairing between a 3' subdomain of the molecule and a 5' subdomain of the molecule, and (iii) a loop domain, wherein the second hairpin molecule is linked to a target biomolecule, and wherein the 5' subdomain of the initial hairpin molecule is complementary to the 5' subdomain of the second hairpin molecule;

(c) two primers, one of which is complementary to the unpaired 3' toehold domain of the initial hairpin molecule and the other of which is complementary to the unpaired 3' toehold domain of the second hairpin molecule;

(d) a plurality of catalytic hairpin molecules, each molecule comprising (i) an unpaired 3' toehold domain, (ii) a paired stem domain formed by intramolecular nucleotide base pairing between a 3' subdomain of the molecule and a 5' subdomain of the molecule, and (iii) a loop domain, wherein the 5' subdomain of each hairpin molecule of the plurality is complementary to the 5' subdomain of one other hairpin molecule of the plurality, wherein the 3' toehold domain of one of the hairpin molecules of the plurality is complementary to the 5' subdomain of the initial hairpin molecule, and wherein the 3' toehold domain of another of the hairpin molecules of the plurality is complementary to the 5' subdomain of the second hairpin molecules; and (e) polymerase having strand displacement activity.

68. A method of recording distances between target biomolecules, comprising combining in reaction buffer
(a) an initial hairpin molecule comprising (i) an unpaired 3' toehold domain, (ii) a paired stem domain formed by intramolecular nucleotide base pairing between a 3' subdomain of the molecule and a 5' subdomain of the molecule, and (iii) a loop domain, wherein the initial hairpin molecule is linked to a target biomolecule, (b) a second hairpin molecule comprising (i) an unpaired 3' toehold domain, (ii) a paired stem domain formed by intramolecular nucleotide base pairing between a 3' subdomain of the molecule and a 5' subdomain of the molecule, and (iii) a loop domain, wherein the second hairpin molecule is linked to a target biomolecule, and wherein the 5' subdomain of the initial hairpin molecule is complementary to the 5' subdomain of the second hairpin molecule, (c) two primers, one of which is complementary to the unpaired 3' toehold domain of the initial hairpin molecule and the other of which is complementary to the unpaired 3' toehold domain of the second hairpin molecule, (d) a plurality of hairpin molecules, each molecule comprising (i) an unpaired 3' toehold domain, (ii) a paired stem domain formed by intramolecular nucleotide base pairing between a 3' subdomain of the molecule and a 5' subdomain of the molecule, and (iii) a loop domain, wherein the 5' subdomain of each hairpin molecule of the plurality is complementary to the 5' subdomain of one other hairpin molecule of the plurality, wherein the 3' toehold domain of one of the hairpin molecules of the plurality is complementary to the 5' subdomain of the initial hairpin molecule, and wherein the 3' toehold domain of another of the hairpin molecules of the plurality is complementary to the 5' subdomain of the second hairpin molecule, and (e) polymerase having strand displacement activity, and deoxyribonucleotide triphosphates (dNTPs), thereby forming a reaction mixture; and incubating the reaction mixture under conditions that result in nucleic acid polymerization, strand displacement and annealing, for a time sufficient to produce a double-stranded nucleic acid record.

EXAMPLES

The Examples below demonstrate, inter alia, the design and implementation of several systems utilizing the PER molecular primitive, which provides a general framework for isothermally synthesizing arbitrary ssDNA sequences in situ. The data shows how primer exchange reactions (PER) can be chained together to form reaction cascades that synthesize fixed length oligos. A nanodevice that synthesized a functional DNAzyme in response to sensing an oncogenic miRNA marker, a label-free biosensor capable of detecting and amplifying the signal detection of a miRNA target with a synthetic telomerase, logic circuits capable of detecting orthogonal RNA inputs, and a molecular recorder that memorized the order of two input signals were all successfully implemented, as described below. In many cases, the logic of the system can be implemented by reconfiguring the same molecular inputs and hairpins into different pathways.

Primer exchange reactions require no thermal cycling to facilitate the catalytic elongation of nascent primer strands and are fueled by dNTPs, which are inexpensive and readily available to molecular biologists. Further, the reaction rates can be tuned by the concentration of hairpins and magnesium ions in solution. The environmental responsiveness of PER was demonstrated in the nanodevice, biosensor, logic circuits, and recorder and presents a powerful new method for using the dynamic synthesis of DNA as a signal processing and actuation platform. Additionally, the ability to prescribe the sequence of the single-stranded output provides the opportunity to interface directly with any number of extant nanodevices in addition to DNAzymes, such as toehold switches (Alexander A Green, et al. Cell, 159(4): 925-939, 2014) or DNA strand displacement circuits (David Yu Zhang and Georg Seelig. Nature chemistry, 3(2):103-113, 2011). Moreover, the environmental responsiveness of PER might be further be extended to protein detection through aptamers and dynamic gene synthesis. The programmable recording, processing, and actuation capabilities of PER circuits fuels a new paradigm of molecular programming applications.

Of particular interest, for example, are the molecular recording applications PER pathways enable. Because long polymers can be grown following different pathways depending on the current state of the environment, PER pathways could be used to create molecular "ticker tapes" that record environmental signal information over long periods of time. These information-rich DNA polymers tapes can then be sequenced to recover the molecular event reports. This type of recording behavior has a profound impact on the study of dynamic biological systems, for example, by recording information about diverse molecular species and events without themselves perturbing the system in a significant way.

Example 1

This Example demonstrates that primer exchange reactions can be used to elongate nucleic acid strands according to prescribed pathways. The first reaction was incubated for 2 hours at 37° C. using Cy5-labeled primers at a concentration of 100 nM and hairpins at a concentration of 10 nM (FIG. 3A). The second reaction was incubated for 4 hours at 37° C. using a FAM-labeled primer incubated for 1 hour before a Cy5-label primer was introduced. The primers were used at a concentration of 100 nM and hairpins were used at a concentration of 10 nM. Heat deactivation of the polymerase by incubation at 80° C. for 20 minutes halted the reactions. Reactions may also be stopped by heat deactivation of the polymerase or by introduction of a chelator (e.g., EDTA).

In another reaction, primers and hairpins were incubated together under different conditions to validate and characterize the basic single primer exchange reaction (FIG. 1C(iv)). The system comprised two components, the fluorophore-labeled primer and hairpin depicted in FIG. 1C(ii), and denaturing gel electrophoresis was used to track the progression of the basic primer exchange reaction. Lane 1 shows the band corresponding to the primer with no hairpin, and lanes 2-11 depict the time progression of a single primer exchange reaction at 10 minute intervals with a 100:1 primer to hairpin ratio. Lanes 12-22 show the same reaction incubated for 90 minutes with different amounts of starting hairpin. These data confirm the catalytic recycling of the hairpin in solution and demonstrate the versatility of hairpin concentrations that can be used to tune the rate of PER systems.

There are several considerations that are taken into account when designing a primer's binding affinity with the hairpin. Firstly, the primer should be short enough to spontaneously dissociate from the hairpin in the last step, for both maintaining the growing strand's predominantly single-stranded state and also for facilitating any subsequent primer exchange reactions. On the other hand, the primer should be made long enough to bind the hairpin for enough time to be extended by the polymerase. This length range may be, for example, 7-10 base pairs using a particular combination of polymerase, temperature, salt, and buffer conditions.

Example 2

Primer exchange reactions can be chained together to form PER cascades that grow strands of a fixed length following a prescribed reaction pathway. The first PER pathway we implemented was a cascade of 5 elongation steps mediated by a set of catalytic hairpin species in solution with dNTPs, polymerase, magnesium, and primers (FIG. 2A(i)). With all 5 hairpins and the primer present in solution, the pathway proceeds through 5 elongation steps (FIG. 2A(ii)). Hairpin A catalyzes the extension of the primer domain a with domain b. Then, hairpin B catalyzes the extension of domain b with domain c. And hairpins C through E catalyze the extension of c with d, d with e, and e with f, respectively.

Denaturing gel electrophoresis validates the ordered elongation of the primer strand when mixed with different subsets of the hairpins (FIG. 2A(iii)). Lane 1 shows a reaction where just the primer and no hairpins were incubated together. Lane 2 shows the primer incubated with hairpins B through E, which is all hairpins except the one that initiates the growth, hairpin A. This control shows no detectable leakage. Lane 3 shows the first elongation step with the primer and hairpin A incubated together. Lane 4 shows two elongations when the primer is incubated with the first two hairpins, A and B. Lanes 5, 6, and 7 show three, four, and five elongation steps of the primer when incubated with hairpins A through C, A through D. and A through E, respectively. Lengths of product bands were further verified by imaging gels after Sybr Gold staining. Catalytic turnover of all hairpins was verified through the nearly complete conversion of all primers to the last state, despite the hairpins being present at ⅒th the primer concentration.

To see whether it was possible to further scale up PER synthesis, the staples for a DNA origami structure were synthesized in a one-pot reaction. A structure comprised of a 3-letter code scaffold held together by 40 staple strands was designed to fold into a compact rectangular shape that aggregates along its short end to produce chains of origami structures. A total of 80 hairpins were designed to synthesize the 40 staple strands from 40 primers (FIG. 2A(iv)), each in two reaction steps. The 80 reactions were all run in parallel through incubation with polymerase for 1 hour at 37° C. After heat inactivation, the scaffold strand was introduced directly into the PER mix and annealed for one hour. Origami structures were then visualized through atomic force microscopy to verify proper structure formation.

Examples of primer exchange reactions with low leakage and high conversion rates are further described in this Example. A primer exchange reaction was used to construct a synthetic telomerase, allowing for an arbitrary sequence to be continuously duplicated, resulting in its elongation by up to hundreds of bases in just a few hours (FIG. 4). The synthetic telomerase construct (FIG. 3) used Cy5 labeled primers at 100 nM final concentrations, and hairpin concentrations of 10 nM-100 nM. The Bst large fragment polymerase was mixed with 1× ThermoPol buffer (20 mM Tris-HCl, 10 mM, $(NH_4)_2SO_4$, 10 mM KCl, 2 mM $MgSO_4$, and 0.1% TritonrX-100), 10 mM $MgSO_4$, and 100 μM dATP, dCTP, and dTTP, 20 μL reactions were prepared at 4° C. and incubated for 4 hours at 37° C., after a 15 minute pre-incubation period with a specialized sequence that cleans up residual dGTPs. Heat deactivation of the polymerase by incubation at 80° C. for 20 minutes halted the reactions. After incubation, reactions were mixed with 10 μL 100% formamide, and 5 μL was loaded into each gel lane of a 15% PAGE denaturing gel (1×TBE and 7M Urea). Gels were run at 200V for 35 minutes at 65 C and scanned with the Cy5 channel. Gels were also stained with Sybr Gold and subsequently imaged with the Sybr Gold channel (data not shown).

More complex state transitions, such as the extension of a strand by a given number of elongation steps, were also programmed (FIG. 5). The multi-step reactions (FIG. 4) used primer concentrations of 100 nM, hairpin concentrations of 10 nM, and 10 μM dATP, dCTP, and dTTP. All other reaction and imaging conditions remain the same as the telomerase construct. No pre-incubation cleanup step was performed.

Both of these experiments used the Bst DNA polymerase, Large Fragment, which has sufficient strand displacing activity at the incubation temperature of 37° C. to facilitate the primer exchange reactions. Domains 1 through 6 (FIG. 5) were made up of a three-letter code composed of the bases C, A, and T, so that the G base could be used as a stop sequence to halt the polymerase. The primer sequences were each 8-9 base pairs in length, designed to be long enough that they could bind to the hairpins stably enough to be copied, but also short enough to spontaneously dissociate from of the hairpin after copying. The primer sequence lengths may be longer for higher temperature reactions or shorter for lower temperature reactions.

Example 3. Triggered Assembly of Long Polymers

In one experiment, hairpin sequences were designed to copy 10 bases per primer exchange reaction step for 5 steps (FIG. 5), resulting in a total addition of 50 bases. Using one hairpin per sequence addition, primer exchange reactions were used to extend a 9 nucleotide primer sequence by 10 nucleotide in each of 5 sequential elongation reactions. Reactions were incubated for 4 hours at 37° C. This elongation can be increased using two complementary approaches (FIGS. 8A-8B). First, orthogonal primer sequences (e.g., at least 30 primer sequences) can be designed to increase the number of steps in the reaction graph. The number of bases on each hairpin that are copied can also be increased. Each hairpin can be programmed to permit an arbitrary sequence to be copied before the next primer sequence, although, in some instances, the processivity of the polymerase enzyme and increased time for the back strand displacement process impose some practical constraints on the length of this region.

In another experiment, the primer exchange reaction conditions are such that at least 30 bases are copied per elongation. Thus, a scaffold of at least 900 bases in length is synthesized. A staged assembly strategy is used, where each hairpin is introduced sequentially to elongate a primer strand docked to a surface, with washing steps in between. Because there are no other hairpins in solution at any given point in time, the probability of spurious priming events occurring is minimal. For this reason, this method can be easily scaled up to the larger lengths. Staple strands are then introduced after the scaffolds are assembled in situ, to avoid off-pathway binding events. An autonomous strategy, where all hairpins are included in solution during scaffold synthesis, is also utilized.

Methods. All DNA strands are synthesized commercially and suspended in 1×TE buffer (10 mM Tris-HCl and 1 mM EDTA) for long term storage at −20° C. DNA sequences are designed using the NUPACK software package, as well as developed software to optimize for primers with the desired binding energies. Primers are initially HPLC purified, and hairpins are ordered unpurified with the inverted dT modification on their 3' ends to prevent extension by polymerases. For reactions, DNA are combined with the Bst strand displacing polymerase (or Phi29, Bsu large fragment, or Klenow (exo-)) and 1× ThermoPol buffer (20 mM Tris-HCl, 10 mM, $(NH_4)_2SO_4$, 10 mM KCl, 2 mM $MgSO_4$, and 0.1% TritonrX-100). Supplemented magnesium can dramatically increase the reaction rate (data not shown), so $MgSO_4$ concentrations are varied from 5 mM to 50 mM to adjust the speed of the reaction while still maintaining specificity. Primers are run at 100 nM final concentrations, and hairpin concentrations are varied from 1 nM to 1 µM, dNTP concentration are varied from 10 µM to 100 µM. The 8-9 bp primer sequence is labeled with the Cy5 dye on its 5' end, and PAGE denaturing gels (15% gel with 1×TBE and 7M Urea) are used to validate the controlled growth of a fixed-length strand. The strand can further be validated with sequencing. To test the staged assembly approach, primers are labeled with biotin on their 5' ends and docked onto a surface coated with streptavidin. Magnetic streptavidin coated beads are used so that the strands are pulled down with magnets for buffer exchange. For washing, 1×PBS buffer is used, to ensure compatibility with cell fixing conditions. Reactions are incubated at 37° C. for times ranging between 2-10 hours for the one-pot synthesis reaction or for 1 hour per staged assembly reaction.

Example 4. Triggered Assembly and Folding of 2D and 3D Structures

In this example, long, fixed length strands are used as scaffolds to fold arbitrary 2D and 3D shapes. For the traditional DNA origami approach, the long strand is used as a scaffold and folded into a shape. A rasterization strategy is used, where the scaffold strand is threaded back and forth through the structure area (FIG. 9A). With this strategy, the scaffold strand is routed through the 2D or 3D shape and then tethered together with staple strands that are complementary to domains on the scaffold that should be localized. In order to assembly structures with features that are large enough to be visualized through microscopy, the 900 bp scaffold produced in Example 3 is used. Approximately 20 staple strands (each having a length of 42-45 base pairs) are used.

Another approach for assembling structures of prescribed shape with primer exchange is to synthesize DNA single-stranded tile (SST) structures that self-assemble into a brick structure (FIG. 9B). With this approach, many small DNA strands cooperatively assemble into complex shapes based on their complementary regions. Each strand is encoded in a single hairpin, so that the number of distinct hairpin species is equal to the number of distinct SST monomers. Alternatively, all SST sequences are synthesized on a single-stranded scaffold and then later cut apart by a restriction enzyme. This strategy permits the use of fewer hairpins using the copy regions in Example 3, although there is potential for the long strand to hybridize with itself and slow down the elongation, due to the co-localization of all SST sequences on one strand.

Yet another approach for assembling structures is to use the synthesized strand as a scaffold for single-stranded DNA origami (FIG. 9C). With this approach, a strand is designed to fold onto itself in an unknotted fashion to create a shape. No staple strands are necessary for the folding because the binding interactions are programmed to be intramolecular. In some instances, all of the binding regions intercalated with the primer regions in such a way that the binding regions are all within the region on hairpin that is copied before the next primer sequence, so that they don't interfere with the extension reactions.

Methods. Methods for incubation reactions are the same as those in Example 3. In some instances, additional magnesium is supplemented to facilitate structure folding and stability after the primer exchange reactions have completed, and concentrations ranging from 10 mM to 100 mM extra cations are used. Agarose gel electrophoresis (2%, stained with Sybr Gold dye) is used to visualize structure formation in bulk. The gel bands corresponding to the fully formed structures are cut out and eluted in buffer with the same salt conditions for validation with transmission electron microscopy (TEM) and/or atomic force microscopy (AFM) imaging. DNA-PAINT super resolution imaging may also be used to directly visualize and evaluate the spatial conformation of individual structures grown. All primer exchange reactions are incubated at 37° C., and structures are folded either at this temperature or room temperature to ensure compatibility with fixed cell conditions.

Example 5. Efficient Growth of Branched Structures

In this example, branched structures are assembled using primer exchange reactions. Because the elongation of new primers should only happen once they have bound to the structure, the hairpins should recognize this co-localization to facilitate copying. This can be achieved by using a priming sequence composed of the two sequences (FIG. 10A). The two individual primer regions (a1 and a2 in FIG. 10A) should by themselves bind too weakly to the hairpin to bind long enough to initiate a priming reaction. When co-localized, however, they should have similar kinetics to the 8-9 base pair primers previously utilized with primer exchange hairpins so that they are short enough to spontaneously dissociate from the hairpins but long enough to successfully initiate strand displacing priming. Because 8-9 base pairs was sufficient for primer lengths in normal primer exchange reactions, a1 and a2 primer regions ranging from 4-6 base pairs are used.

Methods. The methods for incubating and evaluating structures remain the same as in Example 4.

Example 6. Nanodevices

Figures 26A, 26B, 26C, 26D, 26E:
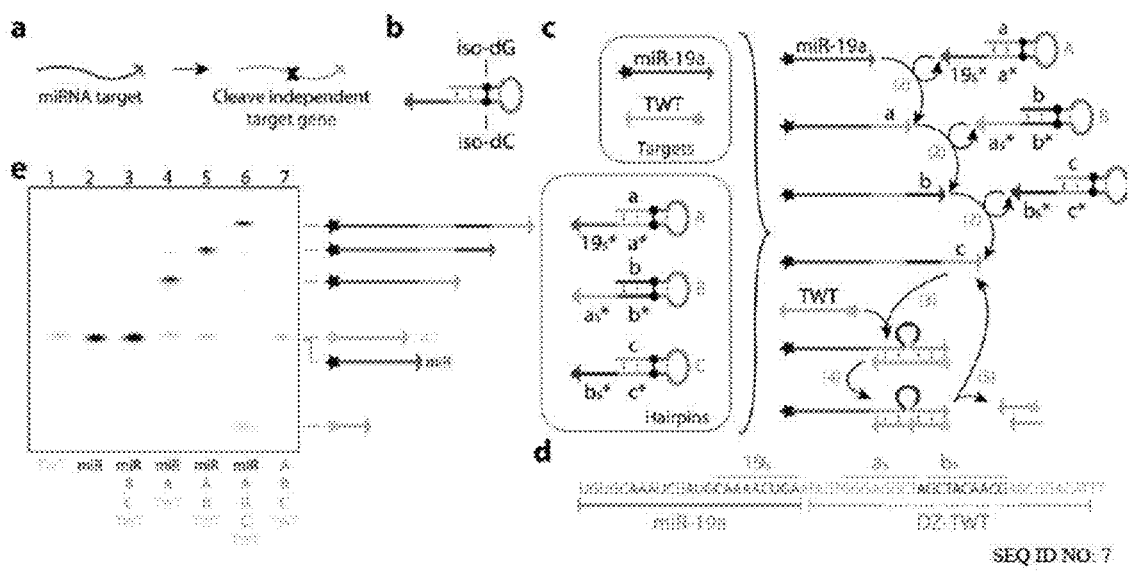

As a demonstration of the versatility of primer exchange reaction applications, we implemented a nanodevice that detects the oncogenic miR-19a signal and subsequently synthesizes a functional DNAzyme that is programmed to cut an independent RNA transcript (FIG. 26A). For target detection, we designed a hairpin to bind the shared 3' region of the oncogenic microRNAs miR-19a and miR-19b. In response to detection, a PER pathway synthesizes a DNAzyme (DZ-TWT) that has been shown to cleave the full length mRNA of the Twist gene and promote apoptosis in vivo.

For this application, a pair of synthetic nucleotides, iso-dG and iso-dC, were utilized as a stop sequence on all hairpins (FIG. 26B). This allowed us to utilize all four DNA bases in the synthesized sequences. As an example of an output construct for PER pathways, we chose to use the DZ-TWT DNAzyme, which has already been validated in vivo.

DZ-TWT is part of the class of 10-23 DNAzymes that have a 15 nt catalytic domain that cuts a specific purine-pyrimidine bond between two arms that are designed to be complementary to a cognate RNA sequence and can be re-programmed to cleave arbitrary RNA sequences. To implement the system logic, three PER hairpins were designed to synthesize the DZ-TWT sequence only upon detection of the target microRNA (FIG. 26C). When the target is present, the A hairpin patterns the synthesis of domain a onto the target strand (step 1). The B and C hairpins can subsequently pattern the appendage of domains b and c, respectively (steps 2-3). The completed a b c sequence forms the DZ-TWT sequence, which can bind to the 24 bp TWT RNA fragment in solution to form a loop that catalyzes the cleavage of the TWT mRNA at a particular base (steps 4-5). The DNAzyme can then be recycled after it dissociates from the cleaved fragments (step 6).

The sequences of the full DNAzyme appended to the target are shown in FIG. 26D. The three domains we split the DZ-TWT sequence into are shown in different colors. The lengths of the primer binding sites on the hairpins (19s*, as*, and bs* on hairpins A, B, and C respectively) were adjusted to bind 8-9 bp of the nascent strand to ensure the nascent strand could dissociate from hairpins after copying.

To evaluate the nanodevice function, we included different subsets of hairpins and the FAM-labeled TWT fragment with and without the Cy5-labeled miRNA target (FIG. 26E). Lanes 1 and 2 show the TWT fragment and miR-19a bands when incubated without any hairpins present. Lane 3 shows that there is no elongation of the miRNA in the presence of the last two hairpins, B and C, but not the first, A. Lane 4 shows the first step of extension when the miRNA is incubated with just the A hairpin and TWT fragment. Lane 5 shows incubation of the target with the first two hairpins, A and B, which results in two step elongation. When the target is mixed with all three hairpins (Lane 6), the full DZ-TWT sequence is appended to it and can successfully cleave the TWT fragment. But when all the hairpins are mixed without target, no cleavage of the TWT fragment occurs (Lane 7). Catalytic turnover of the DNAzyme construct is indicated by essentially complete cleavage of 20 nM TWT RNA with only 10 nM of miRNA target.

Example 7. Label-Free Biosensor

With the nanodevice, we were able to synthesize an arbitrary biologically relevant DNA sequence in response to an arbitrary input sequence. This programmability of PER pathways to transduce one sequence into another presents a powerful modular framework for environmentally responsive synthetic systems, which we explored further with several additional applications. We started by implementing a single-hairpin system that synthesizes long strands of repeated sequence domains, which we call a synthetic telomerase, and then used this construct as a form of signal amplification for a label-free biosensor which grows fluorescent concatemers upon detecting a particular miRNA input (FIG. 27C).

The synthetic telomerase system comprises a single primer sequence (with domain a) and a hairpin that catalyzes the appendage of a repeated domain a onto the growing strand (FIG. 27A). For this demonstration, we chose the 10 bp sequence ATCTCTTATT (SEQ ID NO: 1) as the repeated domain, with the hairpin binding region corresponding to the last 9 bp of the sequence. As before, the primer was labeled with a Cy5 fluorophore for gel visualization and the hairpin was fitted with an inverted dT on its 3' end to prevent its extension.

We validated the construct using a similar experimental setup as previous demonstrations and showed how the reaction rate can be tuned by changing the hairpin concentration over several orders of magnitude (FIG. 27B). Hairpins were incubated with the primer after 15 minutes of incubation with a specialized hairpin species designed to consume extraneous dGTP. Lane 1 shows the primer band with no hairpin added, and lanes 2 through 6 show telomeres grown with hairpin concentrations ranging from 1 to 100 nM. The rate of the reaction can easily be tuned by adjusting the concentration of hairpin in the system, which provides us with a large dynamic range of reaction rates that can be controlled. We also discovered that the magnesium concentration can be used to modulate the telomerization rate, providing yet another method for adjusting reaction kinetics. We subsequently devised a strategy for implementing a label-free biosensor that could conditionally grow this type of telomeric output only in response to the presence of a particular miRNA signal (FIG. 27A). By designing the sequences to bind a particular fluorescent dye, we were able to make these synthesized telomeres fluorescent, allowing for direct visualization of the result under a blue light. The fluorescence is achieved through the binding of the Thioflavin T (ThT) dye, which has been shown to become more fluorescent once intercalated into the quadruplex motifs formed by repeats of the human telomeric sequence TTAGGG. The target we chose was an oncogenic miRNA, miR-19a.

Three components are required to implement the detector-telomerase system (FIG. 27D): a primer (P), a gated hairpin (A), and a telomerase hairpin (B). To transduce target detection into the synthesis of the human telomeric sequence, a toehold exchange reaction was designed such that the primer binding site of a PER hairpin (A) is only exposed in the presence of the cognate miR-19a signal. The miRNA target can bind onto a short exposed domain on the protector strand bound to the A hairpin and branch migrate through the remaining complementary sequence. Once the complementary miR-19a* domain has been fully displaced, the protector strand can spontaneously dissociate from the protected PER hairpin, exposing the primer binding site a* on the A hairpin (step 1). Once exposed, this PER hairpin facilitates the appendage of the b domain onto the a domain of a primer (step 2). The b domain corresponds to the human telomeric sequence TTAGGG, which is subsequently telomerized by a constitutively active telomerase hairpin B (step 3). Finally, these telomeres form a quadruplex structure, into which the ThT dye intercalates and becomes fluorescent (step 4).

To evaluate the conditional telomerization reaction, we incubated reactions with different subsets of components and visualized the results on a native PAGE gel (FIG. 27E). Lane 1 shows a reaction with just the miRNA and none of the molecular program components. With the primer P and telomerase hairpin B but no gated hairpin A, the miRNA target does not bind to any oligos, and there is no telomerization (Lane 2). With the primer P and gated hairpin A, but no telomerase hairpin B, the miRNA binds to the protector strand as indicated by the shift in its band (Lane 3). Telomerization only occurs when all three of P, A, and B are present with the miRNA target (Lane 4). In the control reaction, which contains none of the miRNA target, elements P, A, and B produce almost no background telomerization (Lane 5).

As a simpler readout method, the fluorescence of the reactions can be visualized using a Safe imager 2.0 Transilluminator, through the amber filter unit (vis). This provides a safe, cost effective, and time efficient manner of reading out the signal. The tubes may also be visualized on a fluorescence scanner under the FAM channel (FAM) (see Methods section for full details).

Example 8. Logic Computation

Signal processing of target sequences through logic expression evaluation has emerged as a valuable framework for programming complex dynamic molecular behaviors. Below, we show how PER can be used to implement AND, OR, and NOT logic for arbitrary sequences simply by programming which primer sequences get appended based on the presence (or absence) of target strands. The basic strategy is to equilibrate the RNA targets with the gated hairpins, introduce the primer, and read out the result by length on a gel after incubation (FIG. 28A).

An OR gate for two RNA inputs can be implemented with two of the gated hairpins introduced in the sensor and recorder applications (FIG. 8 B). Each target can activate one of the two hairpins, and when one or both of the two hairpins are activated, the b domain can be appended onto the primer's a domain. Results were validated with a denaturing gel, which shows no extended products when neither target is present (lane 1). However, if one or both targets are present, the primer is extended by one domain (lanes 2-4). To evaluate whether two targets are both present (AND logic), their presence was checked in a stepwise manner (FIG. 8C). The primer domain a does not get extended if neither target is present (lane 5) or if just the TWT target is present (lane 6). If just the miR-19a target is present, the primer is extended by one domain to a b (lane 7). However, if both targets are present, the primer gets extended to the full a b c sequence, indicating successful evaluation of the AND expression (lane 8).

Implementing NOT logic requires a separation of timescales between target acceptance and rejection (FIG. 8D). This can be achieved by including a target-dependent sink reaction at a much higher concentration than the hairpin that evaluates to True (b c). Thus, if the target, miR-21 in this case, is present, then the b primers get funneled into an inactive (gray) state. However, if no target is present, at a slow rate all of the b primers will get converted to b c. The gate was validated by comparing incubation results without (lane 9) and with (lane 10) the target, respectively.

Figures 28A, 28B, 28C, 28D, 28E:
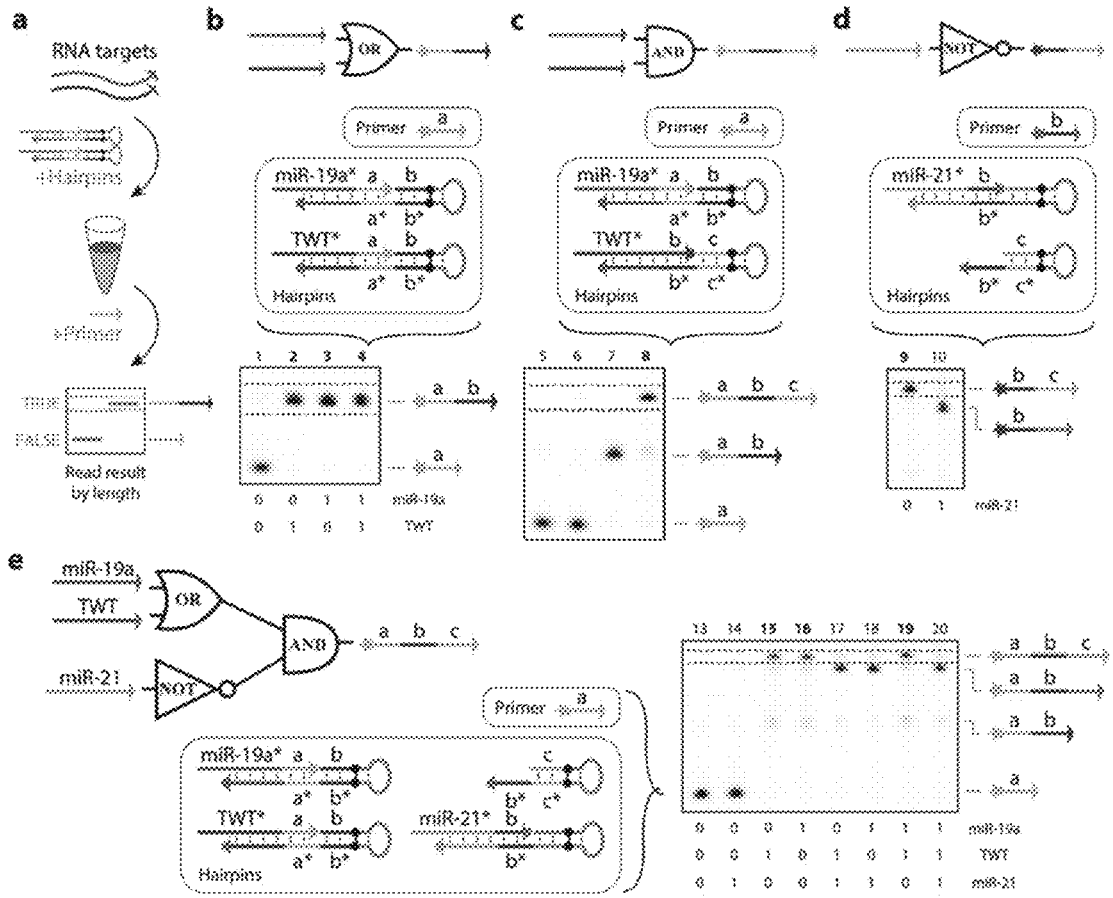

Finally, we demonstrated that several of these types of gates can be hooked together to compute the expression (miR-19a OR TWT) AND (NOT miR-21) (FIG. 28E). This computation is achieved through the cascading of the result of the miR-19a OR TWT gate from FIG. 28B into the NOT miR-21 gate from FIG. 28D. The results were validated as before through gel electrophoresis. Primers remain predominantly in their unextended state when either no inputs or just the miR-21 target are present (lanes 13 and 14). When either just the TWT or just the miR-19a is present, the expression evaluates to True as indicated by the fully extended abc product (lanes 15 and 16). However, when one of these is present in addition to miR-21, the primer is funneled into an inactive state (lanes 17 and 18). Having both miR-19a and TWT but no miR-21 again results in a True result (lane 19), but when all three targets are present the expression again evaluates to False (lane 20). These circuit components demonstrate the modularity of the PER method. The results of one logical evaluation can be easily cascaded into each other by matching synthesized and binding primer domains, and this type of reconfiguration could theoretically be extended to any primer domain given any single-stranded RNA or DNA inputs.

Example 9. Event Recorder

With the previous systems, we showed how PER presents a modular framework to implement environmentally responsive behaviors because the output sequences can be entirely independent from the input sequence. To further demonstrate the programmability of PER, and its applications in molecular signal processing, we created a temporal recording system capable of encoding the order in which two RNA targets are witnessed into dynamically synthesized transcripts (FIG. 29A).

Figures 29A, 29B, 29C, 29D:
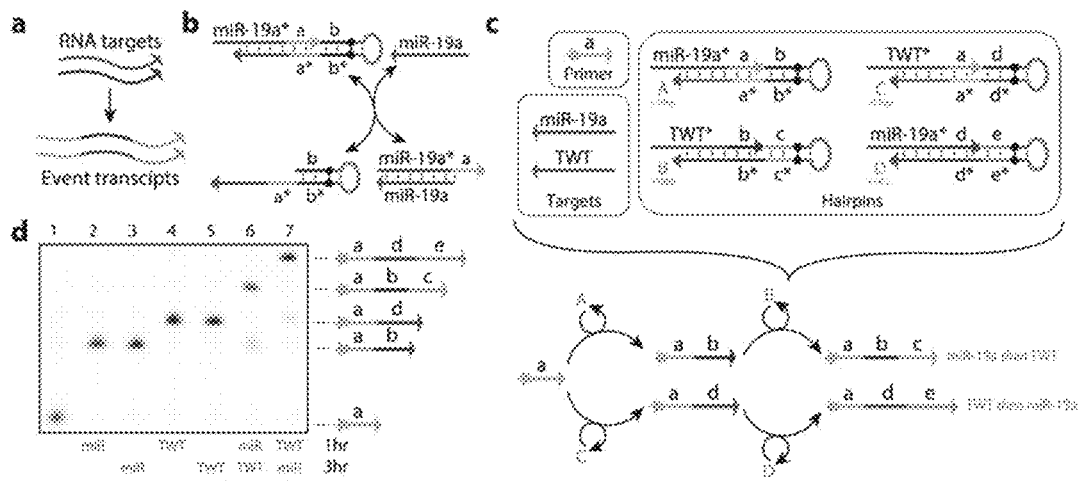

Each of the four hairpins used in this application utilize the same method of toehold exchange for target detection as the label-free biosensor, whereby the binding site of a gated PER hairpin is conditionally exposed only in the presence of a cognate signal, in this case miR-19a (FIG. 29B). Gated hairpins A through D pattern the dynamic elongation of a primer (FIG. 29C), with hairpins A and D becoming activated only in the presence of the miR-19a signal and hairpins B and C becoming activated in the presence of a fragment of the Twist gene, TWT (FIG. 29C).

Depending on the order in which the two RNA signals are introduced, a primer will undergo one of two elongation pathways. If miR-19a is introduced first, then the initial primer gets extended with the b via hairpin A. Then, if the TWT target is introduced, hairpin B can append c to the primer. If, on the other hand. TWT is introduced first, then d gets added to the a primer sequence with the exposed C hairpin, and hairpin D can then append e if the miR-19a signal is encountered later on.

Because the hairpins are designed to copy different numbers of nucleotides per addition, differentiation of the sequence length is achieved based on the order in which the signals are introduced in solution. These results can be read out on a PAGE denaturing gel (FIG. 29D). By introducing signals at either 1 or 3 hours into a 5 hour incubation with the primer and hairpins A through D, the recording behavior was evaluated. Lane 1 shows the system with no targets introduced and shows no extension due to the continuous protection of all four hairpins. Lanes 2 and 3 show a single extension of 10 bp step patterned by hairpin A when miR-19a (miR) was introduced at 1 and 3 hours, respectively. Introducing TWT at 1 or 3 hours results in a single extension of 14 bp by the exposed C hairpin (lanes 4 and 5). Introducing first the miRNA and then TWT results in two 10 bp extensions to form the a b c sequence. Finally, introducing first the TWT target and then the miRNA results in two 14 bp extension steps to form a d e, thus validating our ability to read out the temporal relationship of the two RNA signals in the length of synthesized DNA.

The dynamic and environmentally responsive synthesis of strands via PER is what enables this type of programmable temporal recording and represents a critical advantage of the PER technology to create transcripts of molecular events. We have complete sequence programmability at every step, enabling the detection of arbitrary target sequences and subsequent transduction of signal information into sequence identity and length as a form of molecular memory.

Example 10. Implementing PER In Vivo

Because PER provides a new way to couple the reading and writing of independent nucleic acid sequences, implementing it in vivo enables a highly programmable gene regulation and recording platform within cells. PER cascades are already designed to operate at 37° C., a standard cell incubation temperature, although primer lengths could be adjusted to allow PER to operate at a different temperature. The reactions have been validated under a wide range of magnesium concentrations, from 2 mM to 22 mM, which is compatible with biological samples.

Provided herein are at least two approaches to implement PER in vivo, with different applications for each (FIG. 30). The first approach is to directly transform or transfect the target cell population with the PER hairpins (FIG. 30A). The primer is either introduced together with the hairpins, or can be a sequence already transcribed within each cell. As this approach doesn't target every cell, the applications may be used to primarily for recording. For example, PER can be used to record multiplexed signal information at a single-cell level, and the synthesized transcripts can be recovered and sequenced. Since the 3' ends of the hairpins already typically have an inverted dT base, in some instances, they also have some protection against degradation within the cell.

A second approach incorporates the PER hairpin sequences into a plasmid or cell's genome, so that they may be transcribed into RNA hairpins for use with RNA PER (FIG. 30B). This expression approach has the benefit of creating entire populations with intracellular PER synthesis, if the cells with the components successfully incorporated are selected for. Because the coverage is much greater, and since the PER cascade components are passed down through generations, recording of cellular components can happen over a longer time frame, relative to the first approach. Any programmed behavior also has greater coverage. PolyT tails can be used on the 3' ends of hairpins, as they have been already demonstrated as effective inhibitors of undesired hairpin extension.

Reliable stop sequences will prevent a strand displacing RNA polymerase from continuing past it, which is required for the displacement of the newly synthesized strand from the hairpins. In some embodiments, a sequence motif (e.g., tetraplex (quadruplex) and triplex structures) that folds a structure at the stop junction to inhibit polymerization may be used. In other embodiments, a strong binding protein (e.g., dCas9, whose RNA binding handle is a hairpin structure that could directly be included as the stem loop portion of all hairpins) that binds to a specific sequence motif shared among all hairpin stems to hinder polymerization may be used.

Example 11. Molecular Clocks for Measuring Time

To maximize PER multiplexing capabilities, a large set of operational signal detection modules are compiled for a wide range of single-stranded nucleic acids such as DNA and mRNA, double stranded DNA, and small molecules and proteins (FIGS. 12A-12F). For example, a hairpin's primer binding region is exposed only when the cognate signal (e.g., calcium ion concentration) is present in solution, either with a protector strand or a crosslinker. Because each hairpin defines the transition between states of a primer strand, inhibiting the hairpin when the required signal is not present effectively halts the primer at its current state. For detecting single-stranded DNA and RNA, a modified toehold exchange reaction[58,59] is used, where the protector strand (e.g., sequence x2' x1' 1 in FIG. 12A) is in excess concentration to the hairpin concentration to reduce the potential for leakage.

Detecting double-stranded DNA is done by using an asymmetric PCR method to attach cognate toehold pairs onto the ends of the duplex. This method is further extended to detect proteins and small molecules, by using an aptamer sequence to occlude the hairpin's primer binding region only when the signal is not present. Finally, UV irradiation is detected through the use of CNVK crosslinker.[57] All of these signal detection mechanisms are reversible, which means both that signals are not sequestered indefinitely from the solution they may be operating in and that changes in signal concentrations are reflected by changes in hairpin binding site exposure.

To measure time, a telomerase subcircuit is used as a clock by tracking the distribution in sequence extension steps (FIG. 13). Because the signals detected do not change the kinetic properties of the system, such as the "on" rates for primer exchange elongation steps, the number of telomerase steps the strands in solution undergo between detecting signals indicates the amount of time that those telomerase subcircuits were active. Overall, the system acts as a synthetic stopwatch, encoding the amount of time elapsed between detecting two signals by connecting the telomerase with two input modules. Furthermore, the timescales across which time is measured can be adjusted by changing the hairpin concentration, which effectively changes the speed of the reactions, as well as the amount of dNTPs in solution.

Methods. Reaction incubation conditions remain the same as in Example 4, dNTPs are initially be used at 100 µM concentration, and hairpin concentrations are varied from 10 nM to 1 µM, with the concentration of the telomerase hairpin lower than that of the others. dNTP concentrations are varied to match the desired kinetics, so that the dNTP concentration is low enough to promote high fidelity polymerization but high enough to not be substantially consumed through the operation of the system. Concentrations of input signals are varied to optimize the signal detection modules and find the right compromise between specificity and yield. Primers are incubated at 100 nM and labeled as described above with the Cy5 dye to enable screening on denaturing polyacrylamide (PAGE) gels. Proper ladder synthesis between the detected molecular events can be visualized by the distribution of band lengths on PAGE gels and compared against benchmark reactions that were incubated with identical reaction conditions for specific amounts of time. Because the resolution of the gel can make exact distribution fitting difficult for longer sequences, they are further validated using next generation sequencing.

Example 12. Molecular Timers for Programmable Temporal Actuation

The delay circuit described in this example involves a set of sequential elongation steps between a signal detection event and actuation, which are programmed to take place over a certain period of time (FIGS. 14A-14C). By having primers traverse several reaction states before actuating, time delays are created and tuned by changing either the number of reactions or the concentrations of hairpins and therefore speeds of the reactions. This modularity permits actuation after a wide range of time delays (e.g., actuating on the minutes to days timescales).

Due to the ability to copy arbitrary sequences on the primer exchange hairpins, primer exchange reaction systems are capable of outputting many arbitrary single-stranded signals as output. This single-stranded signal can be used to interact with a strand displacement circuit in solution or hybridize with complementary RNA molecules. In some instances, this output activates a toehold switch[58] that activates protein synthesis. Alternatively, the sensing of a toxic signal triggers a toehold switch with one output and then deactivates that same switch with another one after a set amount of time. This permits pulses of output signal in response to an environmental signal, without requiring the output to be indefinitely activated (FIGS. 15A-15D). This level of programmable, temporal control of protein signals has been difficult to scale up with previous technologies and is useful for engineering functional synthetic systems or studying fundamental biological mechanisms, such as reaction kinetics, in a controlled in vitro environment.

Methods. Primer exchange incubation conditions remain the same as in Example 6. Timer circuit delays are evaluated by directly measuring the output over time to verify a proper delay in actuation, such as with a spectrofluorometer measuring the displacement of a fluorophore-labeled strand from its quencher-labeled complement by the output signal over time. Another option for measuring the delay is to monitor fluorescence over time using the activation of a GFP-producing toehold switch over time.

Example 13. Multiplexed Temporal Recording and Actuation

Primer exchange reactions provide a modular framework to actuate in response to different sets of signals, for example, by releasing outputs only if one of two molecules are sensed (OR logic) or only if both are sensed (AND logic) (FIGS. 16A-16I). They are also programmed, in some instances, to detect whether a signal is not present (NOT logic), if after a programmed delay the input has not been detected. These gates are linked together to perform logic on a large set of environmental signals and actuate in the ways described above (FIGS. 17A-17C). These digital logic circuits are responsive to different sets of signals detected at different times and provide the basis for sophisticated signal processing systems that interact with transcriptional and translational networks.

Each module in an integrated system is first be tested separately, as described in Examples 6 and 7. Subsequently, they are combined in a stepwise manner, to ensure each subcircuit in the system maintains its functions and facilitates the debugging required to fix any problems.

Methods. The methods remain the same as those in Examples 6 and 7.

Example 14. Differentiation Through Developmental Self-Assembly

By combining the signal detection modules developed in Examples 6-8 and the triggered structure synthesis developed in Examples 3-5, it is possible to engineer the differentiation of shape formation based on environmental signals (FIGS. 19A-19C). Each signal detector module requires a single hairpin whose primer binding region is exposed only in the presence of a cognate signal. The terminal states of the differentiation tree serve as the triggers for structure formation.

Methods. Methods for reaction incubation and structure evaluation remain the same as those in the above Examples. Using Cy5-labeled primers, proper length distributions of strands for the first steps of developmental self-assembly are verified via denaturing polyacrylamide gel electrophoresis (denaturing PAGE, typically TBE-Urea). Subsequently, the differentiated shapes grown on the primer are evaluated first with non-denaturing agarose gel electrophoresis and then visualized using TEM or AFM imaging. The structures are also be imaged with the DNA-PAINT super-resolution method.

Example 15. Molecular Ticker Tapes for Environmental Recording

The dynamic synthesis reactions of PER cascades can be used to record molecular signal information over time. One powerful example of this is with a molecular ticker tape system, which couples signal-dependent synthesis with continuous PER telomerization reactions to record information about when particular signals are present in a solution (FIGS. 20A-20D). First, a one-signal tracking system was implemented, which can be used to elucidate the kinetics of a single signal over a two-hour period. A description of the experiments and their results is provided below.

Molecular implementation. The molecular implementation of the one-signal system consists of two PER hairpins, one that serves as a molecular "clock" and is present in all experiments at the same constant concentration, and one that serves as the "signal" and patterns the copying of a couple extra bases before the repeated primer sequence (FIGS. 21A-21D). Each different experiment uses a primer that has an experiment-specific barcode sequence before the repeated domain, so all experiments can be pooled together and submitted together in a single sequencing run.

Experimental Overview

Recording. Three recording experiments were performed. In Experiment A, no signal was introduced throughout the two-hour incubation period. This served as a control experiment to verify proper clock reactions took place. Experiment B had a constant signal hairpin concentration of 500 µM throughout the two-hour incubation. This reaction was used as a benchmark for fitting the last experiment, as the relative signal to clock rate could be used to calibrate the concentration curve. Experiment C was run for an hour with no signal, and then 200 µM of signal was introduced halfway through, making the concentration curve a step function.

Recording was done at 37° C. for two hours. Reactions were prepared on ice with 5 µL 10× ThermoPol buffer, 40 units of Bst Large Fragment DNA polymerase, 5 µL 100 mM MgSO4, 5 µL 100 µM solution of combined dATP/dTTP/dCTP, 5 µL 1 µM appropriate primer, 5 µL 50 nM clock hairpin, 5 µL 5 nM signal solution for experiment B only, and water to 50 µL. For reaction C, 1 µL 10 nM was added after 1 hour of incubation. After incubation, reactions were moved to ice and stopped with 10 µL 0.5M EDTA. Pooled reactions were then run through an NEB Monarch PCR & DNA Cleanup Kit to purify the recorded transcripts.

Adaptor tagging. Purified transcripts were then tagged with adaptor sequences on their 5' and 3' ends (FIG. 22). Ligation strands and records were mixed with an excess of splint strands and ligated with T4 DNA ligase in 1×T4 DNA ligase buffer through incubation at 23 C for 1 hour. After ligation, the transcripts were again purified with a DNA cleanup column.

Gel extraction. Purified adaptor-tagged oligos were run on a 15% PAGE denaturing gel (1×TBE) held at 65° C. The gel was run for 15 minutes at 200V and stained with 1× Sybr Gold dye. Gel extraction of adaptor-tagged sequences was performed on a Typhoon FLA 9000 scanner after visualizing the sequence distribution in the Sybr Gold channel. Extracted pieces of the gel were put into and smashed in a 1.5 ml conical tube and then combined with 50 µL 1×TE and spun down. After sequential incubation at −80 C and 90 C for 10 minutes each, components were put into a Freeze 'N Squeeze DNA gel extraction column and spun at 15,000 g for 1 minute. Extracted transcripts were passed through one additional DNA cleanup column before being sequenced.

Transcript sequencing. Illumina® paired-end DNA sequencing was used to sequence transcripts.

Sequence parsing. Sequences were received in FASTQ format and parsed into clock (0) and signal (1) records as follows. First, only sequences where both the initial primer sequence with a valid experimental barcode and the beginning of the 3' adaptor tag could be identified were retrieved, as this indicates that the full record was sequenced and could be applied to one of the experiments performed. Next, every occurrence of the sequence corresponding to the signal hairpin was replaced with a '1' and then every occurrence of the repeated clock domain encoded by the clock hairpin was converted to a '0', with the initial repeat domain on the primer excluded. Only records with perfect binary strings of 0's and '1's were analyzed.

Results

Parsed binary sequences were used to fit concentration curves, and the results of this optimization can be seen in FIGS. 23A-23B.

In this Example, we showed that not only are we able to recover concentration information about signals with in the environment with molecular ticker tapes, we can also recover kinetic information about how these signal change over time. This type of temporal recording could have profound impact on our ability to study biological phenomena in a multiplexed and quantitative manner. Moreover, 200 pM of signal was easily detectable with our sequencing data, indicating another potential application of this recording technology: highly sensitive target detection. If we can further scale the detectable limit down to smaller concentrations, this technology could be applied to the multiplexed detection of markers at very low concentrations, such as miRNAs in serum or other body fluids.

As another example, by combining the clock and pathway reconstruction systems implemented in Examples 6-8, information about environmental signals can be recorded and then read out over time with high precision. This is achieved through the use of signal detection events encoded into a continuously elongating strand. One telomerization reaction is used as a clock, and the additional reactions record different signals over time (FIGS. 20A-20D). By considering the distribution of clock and signal sequence incorporations over time as a result of the actual signal concentrations, a concentration trace for each signal over absolute time is fit to the data. To fit these data, the reaction rates are measured for each incorporation type by running controlled experiments where only the clock is running and where signal concentrations are varied and only one signal detector module is operating. Because the amount of time the circuit is running and the signal concentrations are known, the distribution of lengths is used to determine the on rate, $k_{on}$, for each individual reaction. These rates are then used to determine the relative concentrations of signal over time based on the number of incorporations in a ticker tape transcript and known reaction rates.

The primer sequences contain unique molecular identifiers (UMIs) on their 5' ends composed of a random sequence of bases. These are used to identify duplicate reads in the sequencing data and reduce bias in the data analysis by preserving as much quantitative information about the time dependence of environmental signals as possible.

Methods. Reaction conditions remain the same as those in Examples 6-8. Each Cy5 labeled primer is also labeled with 15 nucleotide unique molecular identifier (UMIs), so that the transcripts are amplified through a PCR reaction and read out with next generation sequencing methods. With 15 nucleotide UMIs, there are 1,073,741,824 possibilities, so it is very unlikely that reads with identical UMIs in the up to 20 million reads from sequencing come from different primers even with nucleotide bias. Data is analyzed using specialized scripts to parse, sort, and fit the data to time traces.

For recording signals that affect polymerase kinetics, for example spikes in calcium concentration, an external clock for benchmarking may be used. For example, a crosslinked hairpin may be used to detect UV irradiation of specific wavelengths, which can be pulsed after specific intervals of time and recorded using the detector introduced in FIG. 12D.

Example 16. Motion of Molecular Moors in 1D

The 1D track for testing the basic operation of the crawlers is built on a structurally well-defined rigid DNA nanostructure. A simple DNA origami rectangle, or a DNA brick system is used.[52,53] The following parameters are modified: (1) incubation time, (2) concentrations of the primer, polymerase, and nucleotide monomers, (3) the binding strengths of different domains (primer, information-encoding site, etc.), (4) the spatial interval between adjacent sites on a track, and (5) the release condition. A time scale of 1-2 hours is used, which permits near-completion of reactions. Multiple variations of the incubation time, including seconds to minutes, are also tested to better understand the kinetics of the reactions. A primer concentration of 100 nM and a dNTP concentration of 10-100 nM is tested. The binding strengths of different domains are modified by changing the lengths and GC-contents of the domains, as well as by introducing extra auxiliary components such as bulges for biasing reaction equilibrium when needed. Tracks with different spatial intervals are created by assembling nanostructures with varied distances between track anchor points. A simple two-site track is first tested to characterize the basic distance-dependent performance. Different release strategies as discussed above, such as manually adding "reverse primers" at the end of incubation, embedding a release signal site next to the final track site, or heat-mediated dissociation, are also tested.

Additionally, different total lengths of the tracks are tested to measure any performance degradation over long travel distances. Different track compositions are tested as well. Fully addressed tracks, with sequential instructions (e.g., primer binding sites a*, b* and c*, in order, as shown in FIG. 31A) guide the crawlers along the prescribed paths. Tracks with repeated primers (e.g., consider all primer pairs unified as a-a* in FIG. 31A) allow the crawlers to choose the starting point, and the direction to proceed.

To characterize the assembly of the track structures, direct nanoscale imaging methods, such as atomic force microscopy and super-resolution imaging, are used. For the operation of the crawlers, at the initial investigation stage, mostly qualitative characterizations based on gel electrophoresis are performed. Gel electrophoresis allows fast profiling of reaction products by sorting DNA molecules by their sizes. Comparing the reaction mixes before and after a given step allows assessing the conversion of reactants to products. All complete reactions are visible as bands having lengths corresponding to the lengths of three single records joined together (with auxiliary parts). For incorrect products, depending on the scale of the reaction and the yield, a product amplification step using the polymerase chain reaction (PCR) is added before the gel characterization. Measuring the intensities of gel bands enables an estimation of the reaction yields. In cases of small-scale product formation, quantitative real-time PCR (qPCR) allows an estimation of the amount of products by analyzing the amplification traces over time and extrapolating back to the initial state. Unique identification of molecules with randomized DNA sequences, combined with single-molecule analysis tools, such as next-generation sequencing, are used to show the catalytic and repeated recording behavior of the crawlers, by detecting the generation of multiple records over a single track.

Example 17. Motion of Molecular Motors in 2D

This Example demonstrate the following properties: (1) full angle of motions of the crawlers in 2D space, (2) the ability of the crawlers to roam around and "choose" a path to follow, (3) the ability of the crawlers to collectively gather information about the 2D track.

The 2D tracks are built on a structurally well-defined rigid DNA nanostructure. Tracks with different spatial arrangements are created by assembling nanostructures with varied positions of track anchor points. A simple three-site track with an angle (such as in the "L" shape) is used to test the behavior of the crawlers at junction points. Both types of molecular motor systems (crawler and walker) are tested. Some parameters, such as incubation time and concentrations are adjusted to accommodate the combinatorial number of possible paths. Similarly, different track compositions are tested. Fully addressed tracks, with sequential instructions guide the movement of the crawlers along the prescribed 2D paths. In the cases of tracks with repeated (a-a*, then a-a*, etc.) or alternating (a-a*, then b-b*, then a-a*, etc.) primers, the molecules have freedom to choose the path to follow at junction points (FIGS. 31B and 32B). The right hand sides of FIGS. 31B and 32B show example trajectories of the molecular motors for the two systems, respectively. Different track paths followed by the crawlers are reflected as different lengths and identities of the generated records To characterize the assembly of the track structures, direct nanoscale imaging methods such as atomic force microscopy and super-resolution imaging are used. To characterize the results and demonstrate the key capabilities of the crawlers, multiple characterization methods are used. First, gel electrophoresis shows the formation of records with the correct lengths and the formation of multiple types of records in the cases of tracks with redundant primers. With fully prescribed tracks, gel bands appear having lengths that correspond to the predefined number of track sites. With tracks with redundant primers, where the crawlers are allowed to freely roam around, a distribution of gel bands having lengths spanning across different lengths are visible; in the case of the crawlers, the maximum length observed correspond to the number of track sites. As with 1D tracks, PCR amplification of the records is optionally added before the gel characterization, depending on the scale of reaction and record generation yield. Second, PCR is used to selectively amplify specific kinds of records and detect the formation of the specified records. For example, PCR primers complementary to the primers/primer-binding regions of the first and last track sites are used to selectively amplify the full records. Third, a next-generation sequencing method is used to directly examine the identity of the generated records. Combinations of these characterization methods allow confirmation that all track points are visited repeatedly by the molecular crawlers through multiple kinds of paths.

Example 18. Inspection of Quantitative Information

Molecular motors can roam around given tracks, and copy and "record" the information from the track sites. For generality of this capability, unknown tracks are assumed, with each site labeled with redundant primers (all sites having the same primers). From the lengths of the records generated, quantitative information about the track size and the number of steps taken by the molecules is obtained.

The counting capability of the molecular motors is first tested on DNA nanostructure tracks with a defined number of track sites. For example, tracks with 3 points and 5 points on a 1D arrangement are tested for characterization and optimization of the performance (FIG. 33A). A more complicated 2D track, such as a circle, is also tested to examine the ability of successful counting behavior on a generalized track. From a track with redundant primers, the crawlers generate records with a distribution of lengths, with the maximum length indicating the maximum possible number of track sites (see schematic plot in FIG. 33B), as the sites once visited cannot be revisited until the whole crawler is released from the track. The walkers generate records with a distribution of lengths reflecting the number of steps taken by the walkers. Next, the molecular motor systems are implemented in biological systems (FIG. 28B). For example, targeting of specific molecular complexes is tested. Targeting of nuclear pore complexes with their antibodies coupled with DNA anchors to which "track" sites are attached are used to collect the quantitative information (see, e.g., FIG. 33C for test platform). The dimension of the nuclear pore complexes is relevant and ideal as a test system, because the distance between neighboring subunits is ~30 nm. An orthogonal system is used for obtaining quantitative information, such as direct imaging in super-resolution (FIG. 31C) or counting based on analysis of kinetic traces of stochastic imaging, termed qPAINT (reliably applied to the same system shown in FIG. 31C), as a reference for comparison of the readouts and the relative performance of different methods.

Example 19. Inspection of Identity Information

As the molecular motors copy and report the information from the tracks, if the track sites contained unique information such as unique DNA sequences, the records generated by the crawlers will contain the identity information of each site. Thus, beyond the quantitative information, unique identity information can also be obtained (FIG. 33D).

To demonstrate the records containing the identity information of the sites, multiple characterization methods are used. First, gel electrophoresis coupled with selective PCR amplification of specific kinds of records reveals the generation of specific records. Second, direct examination of the sequence information, based on next-generation sequencing methods, reveals the molecular identities of the generated records.

Example 20. Reconstruction of Molecular Landscapes

Properties of the molecular motors: (1) recording the identity information of given molecular targets and (2) repeated recording along the same targets through multiple kinds of paths, enables the motors to examine and report the landscape of targets. The collective information gathered by the actions of multiple crawlers are used to analyze the geometric arrangement of the target sites, and to reconstruct the molecular landscapes.

Collection of information along a given molecular landscape is tested on DNA nanostructure tracks with a defined arrangement of track sites (FIG. 33E). The crawlers can take different paths at each round of inspection and recording. The records generated after each round reflect a collection of proximity information of the neighboring molecular sites. Direct examination of the records through next-generation sequencing methods enable assignment of each record to a possible path along the landscape. Some proximity information overlaps with information from different records. Records generated around junction points contain proximity information from multiple pairs of track sites. Compiling all the proximity information enables the collection of information of neighboring points and junction points and thus permits reconstruction of the molecular landscape.

Example 21. Molecular Distance Recording

DNA rods (10 nM) of four different lengths (Rod38, Rod49, Rod59, Rod70 and a negative control were used in the molecular recording experiment described in this example. Results from the experiment are shown in FIG. 38A. The number (e.g., Rod38) indicates the length of the double stranded region in base pairs. The DNA rods were independently incubated with precursors (100 nM), catalytic hairpins (1 µM), dATPs (10 µM), dTTPs (10 µM) and Bst, Large Fragment DNA polymerase (0.26 U/µL) in 1× Thermopol buffer (3 mM Mg$^{2+}$), for 4 h at 37° C. The products of the reaction were run on a 15% PAGE gel (0.5×TBE, 8M Urea) at 65° C. and visualized with a Typhoon gel scanner. Results show that records produced correspond to the distance being measured. Some gel bands are labeled with their corresponding DNA records.

DNA rods (concentration 100 µM) of three different lengths (5.4 nm, 12.6 nm and 19.7 nm) were separately incubated with precursors (100 µM), catalytic hairpins (200 nM), dATPs (100 uM), dTTPs (100 µM) and dCTPs (100 µM) and BST Large Fragment DNA polymerase (0.4 U/uL) in Thermopol buffer (supplemented with 5 mM MgSO$_4$) for 30 min at 37° C. Then the solution was treated with Exo I DNA exonuclease (0.1 U/µL) to digest unreacted and unfinished single stranded products. The records produced were amplified by PCR (5 prime Cy5 dye-labeled Primers—250 nM, dNTPs—200 µM, Vent Exo-—0.5 U/µL, Thermopol buffer—1×, 18 cycles, Standard PCR protocol with annealing temperature 46° C.). The results of the PCR reaction were run on a 12% PAGE gel (0.5×TBE, 8M Urea, 200V, 65° C.) and visualized with a Typhoon gel scanner. The results are shown in FIG. 38B. The records produced correspond to the distance being measured. Some gel bands are labeled with their corresponding DNA records to assist with interpreting the gel.

Example 22. Validation of Molecular Ruler Technology on a DNA Nanostructure

DNA nanostructures are used to precisely position DNA targets at known, fixed distances (FIG. 35A) and experiments show that molecular rulers can record these distances.

Example 23. Single Molecule. Multiplexed and High-Throughput Measurement on Complex 2D Geometry Structural mimics of the nuclear pore complex (NPC) are produced by precisely placing eight barcoded DNA targets at the vertices of a regular octagon on a DNA nanostructure (FIG. 35B). Then, the molecular ruler is used to record distances. The distances and the corresponding encoded barcodes are read out using next-generation sequence technology. Molecular rulers are then used to record low copy numbers (104 to 106) of the NPC-mimics to correspond to in situ conditions in typical biological experiments.

Example 24. Apply Molecular Ruler to the Nuclear Pore Complex Infixed U2OS Cells Nucleoporin Nup98 in fixed U2OS cells (human bone osteosarcoma cells) are labeled with a custom DNA-conjugated monoclonal antibody (#2598. Cell Signaling). Super-resolution studies revealed that this labeling results in eight clusters in an octagonal arrangement, with a distance between adjacent clusters of about 30 nm. The molecular ruler is used to record distances between clusters with a resolution of under 4 nm. Gel electrophoresis read-out reveals the expected four distinct diagonal distances and their variances. NGS read-out reveals single molecule distances, enabling the study of the heterogeneity of NPCs.

Methods

DNA synthesis and purification. All oligos were ordered from IDT, either unpurified or HPLC-purified. Purified RNA molecules were ordered purified with RNase-free HPLC. Some unpurified oligos were purified in-house by running 100 µL of 100 µM unpurified oligo through a Qiagen MinElute PCR purification column and washed per kit instructions. Column-bound oligos were eluted to 15 µL and concentrations were measured using a Nanodrop and their oligoanalyzer (www.idtdna.com/site/order/oligoentry) extinction coefficients. Oligos were ordered pre-suspended in 1×TE buffer at 100 µM, and these concentrations were assumed for all dilutions, with the exception of MinElute purified oligos. All oligos were diluted in 1×TE to working concentrations of 10 µM, with stock and working solutions of DNA stored at −20° C. and RNA stored at −80° C.

PER incubation. All PER experiments were incubated at 37° C. for the indicated amount of time, usually with 1× ThermoPol buffer (20 mM Tris-HCl, 10 mM, $(NH_4)_2SO_4$, 10 mM KCl, 2 mM $MgSO_4$, and 0.1% TritonrX-100), 10 mM $MgSO_4$, and 10-100 µM of the appropriate dNTPs. Typically, 20 µL reactions were quenched by heat inactivation of the enzyme at 80° C. for 20 minutes and loaded with 10 µL formamide. For RNA-sensitive samples, reactions were instead quenched with EDTA. For the label-free biosensor, reactions were not quenched but loaded directly after incubation. Some experiments were preincubated for 15 minutes to allow the solution to equilibrate.

Gel electrophoresis. Most experiments used 15% TBE-Urea PAGE denaturing gels that were run at 200V for 35 minutes at 65 C and scanned with the Cy5 and FAM channels. Gels were also stained with Sybr Gold for several minutes and subsequently imaged with the Sybr Gold channel. Some experiments used different gel conditions.

AFM. AFM imaging was performed on a Nanoscope V machine.

Sequence design. Most sequences were designed using in-house optimization code paired with command line NUPACK executables. The NUPACK web application was also used to analyze constructs.

Example 25. Crawler System

A series of tests for one of the molecular motor systems, the crawlers, was performed to confirm the basic operations (FIGS. 43A-43C). A three-point track along a triangular alignment on a DNA nanostructure platform was designed. The top panel of FIG. 43A depicts a schematic of the design, and the bottom panel of FIG. 43A shows the molecular detail of a crawler after crawling over the three target sites. Following completion of the crawling process, the crawlers become the full record of length 118 nt. When amplified by PCR and run on a denaturing gel, the final records appeared at the expected length range (FIG. 43B). The crawlers were also visualized using an atomic force microscope (AFM). The left panel of FIG. 43C shows the target probes before the primers initiating the crawling reaction were added, where the probes appear as dots. After the recording reaction of about 1 hour, crawlers connected the three track sites together as shown in the right panel of FIG. 43C, and thus appear accordingly in the AFM images. These test results demonstrate the basic operation of the crawler system for each step: (1) primer binding. (2) primer extension by a polymerase, (3) strand displacement by the template, (4) interaction with a neighboring site, (5) additional extension by a polymerase, (6) autonomous release of the records.

REFERENCES, EACH OF WHICH IS INCORPORATED HEREIN IN ITS ENTIRETY

1. B. Yurke, A. J. Turberfield, A. P. Mills, Jr., F. C. Simmel, and J. L. Neumann. A DNA-fueled molecular machine made of DNA. Nature, 406:605-608, 2000.
2. R. M. Dirks and N. A. Pierce. Triggered amplification by hybridization chain reaction. PNAS, 101:15275-15278, 2004.
3. G. Seelig, D. Soloveichik, D. Y. Zhang, and E. Winfree. Enzyme-free nucleic acid logic circuits. Science, 314 (5805):1585-1588, 2006.
4. L. Qian and E. Winfree. Scaling up digital circuit computation with DNA strand displacement cascades. Science, 332:1196-1201, 2011.
5. W. B. Sherman and N. C. Seeman. A precisely controlled DNA biped walking device. Nano Letters. 4:1203-1207, 2004.
6. P. Yin, H. M. T. Choi, C. R. Calvert, and N. A. Pierce. Programming biomolecular self-assembly pathways. Nature, 451:318-322, 2008.
7. T. Omabegho, R. Sha, and N. Seeman. A bipedal DNA Brownian motor with coordinated legs. Science, 2009.
8. Ralf Jungmann, Christian Steinhauer, Max Scheible, Anton Kuzyk, Philip Tinnefeld, and Friedrich C Simmel. Singlemolecule kinetics and super-resolution microscopy by fluorescence imaging of transient binding on DNA origami. Nano letters, 10(11):4756-4761, 2010.
9. Ralf Jungmann, Maier S Avendailo, Johannes B Woehrstein, Mingjie Dai, William M Shih. and Peng Yin. Multiplexed 3d cellular super-resolution imaging with DNA-paint and exchange-paint. Nature methods, 11 (3): 313-318, 2014.
10. J. Chen and N. C. Seeman. The synthesis from DNA of a molecule with the connectivity of a cube. Nature, 350:631-633, 1991.
11. P. W. K. Rothemund. Folding DNA to create nanoscale shapes and patterns. Nature, 440(7082):297-302, 2006.
12. Y. He, T. Ye, M. Su, C. Zhang, A. E. Ribbe, W. Jiang, and C. D. Mao. Hierarchical self-assembly of DNA into symmetric supramolecular polyhedra. Nature, 452:198-201, 2008.
13. Y. Ke, J. Sharma, M. Liu, K. Jahn, Y. Liu, and H. Yan. Scaffolded DNA origami of a DNA tetrahedron molecular container. Nano. Lett., 9:2445-2447, 2009.
14. E. S. Andersen, M. Dong, M. M. Nielsen, K. Jahn, R. Subramani, W. Mamdouh, M. M. Golas, B. Sander, H. Stark, C. L. P. Oliveira, J. S. Pedersen, V. Birkedal, F. Besenbacher, K. V. Gothelf, and J. Kjetns. Self-assembly of a nanoscale DNA box with a controllable lid. Nature, 459:73-76, 2009.
15. S. Douglas, H. Dietz, T. Liedl, B. Hogberg, F. Gratf, and W. Shih. Self-assembly of DNA into nanoscale three-dimensional shapes. Nature, 459:414-418, 2009.
16. H. Dietz, S. Douglas. and W. Shih. Folding DNA into twisted and curved nanoscale shapes. Science, 325:725-730, 2009.
17. T. Liedl, B. Hogberg, J. Tytell, D. E. Ingber, and W. M. Shih. Self-assembly of three-dimensional prestressed tensegrity structures from DNA. Nature Nanotech., 5:520, 2010.
18. D. Han, S. Pal, J. Nangreave, Z. Deng, Y. Liu, and H. Yan. DNA origami with complex curvatures in three-dimensional space. Science, 332:342-346, 2011.

19. S. H. Park, P. Yin, Y. Liu, J. H. Reif, T. H. LaBean, and H. Yan. Programmable DNA self-assemblies for nanoscale organization of ligands and proteins. Nano Lett., 5:729-733, 2005.
20. F. Aldaye, A. Palmer, and H. Sleiman. Assembling materials with dna as the guide. Science, 321:1795-1799, 2008.
21. H. Yan, S. H. Park, G. Finkelstein, J. H. Reif, and T. H. LaBean. Dna-templated self-assembly of protein arrays and highly conductive nanowires. Science, 301(5641): 1882-1884, 2003.
22. CJ. Delebecque, A. B. Lindner, P. A. Silver, and F. A. Aldaye. Organization of intracellular reactions with rationally designed RNA assemblies. Science, 333:470-474, 2011.
23. A. Kuzyk, R. Schreiber, Z. Fan, G. Pardatscher, E.-M. Roller, A. Hogele, F. C. Simmel, A. O. Govorov, and T Liedl. Dna-based self-assembly of chiral plasmonic nanostructures with tailored optical response. Nature, 483:311-314, 2012.
24. H. M. T. Choi, Trinh Chang, J. Y., Padilla L. A., S. E. J. E., Fraser, and N. A. Pierce. Programmable in situ amplification for multiplexed imaging of mRNA expression. Nature Biotechnol, 28:1208, 2010.
25. C. Lin, R. Jungmann, A. M. Leifer, C. Li, D. Levner, G. M. Church, W. M. Shih, and P. Yin. Submicrometre geometrically encoded fluorescent barcodes self-assembled from DNA. Nature Chemistry. 4:832-839, 2012.
26. Jinglin Fu, Minghui Liu, Yan Liu, Neal W Woodbury, and Hao Yan. Interenzyme substrate diffusion for an enzyme cascade organized on spatially addressable DNA nanostructures. Journal of the American Chemical Society, 134(12):5516-5519, 2012.
27. Wei Sun, Etienne Boulais, Yera Hakobyan, Wei Li Wang, Amy Guan, Mark Bathe, and Peng Yin. Casting inorganic structures with DNA molds. Science, 346(6210): 1258361, 2014.
28. M. J. Berardi, W. M. Shih, S. C. Harrison, and J. J. Chou. Mitochondrial uncoupling protein 2 structure determined by NMR molecular fragment searching. Nature, 476:109-113, 2011.
29. S. Venkataraman, R. M. Dirks, C. T. Ueda, and N. A. Pierce. Selective cell death mediated by small conditional RNAs. Poc Natil Acad Sci USA, 107:16777, 2010.
30. Lisa M Hochrein, Maayan Schwarzkopf, Mona Shahgholi, Peng Yin, and Niles A Pierce. Conditional dicer substrate formation via shape and sequence transduction with small conditional RNAs. Journal of the American Chemical Society, 135(46):17322-17330, 2013.
31. S. M. Douglas, I. Bachelet, and G. M. Church. A logic-gated nanorobot for targeted transport of molecular payloads. Science, 335:831-834, 2012.
32. Qiao Jiang, Chen Song, Jeanette Nangreave, Xiaowei Liu, Lin Lin, Dengli Qiu, Zhen-Gang Wang, Guozhang Zou, Xingjie Liang, Hao Yan, et al. DNA origami as a carrier for circumvention of drug resistance.
Journal of the American Chemical Society, 134(32): 13396-13403, 2012.
33. T. J. Fu and N. C. Seeman. DNA double-crossover molecules. Biochemistry, 32:3211-3220, 1993.
34. E. Winfree, F. Liu, L. A. Wenzler, and N. C. Seeman. Design and self-assembly of two-dimensional DNA crystals. Nature, 394:539-544, 1998.
35. S. Douglas, A. H. Marbleston, S. Teerapittayanon, A. Vazquez, G. M. Church, and W. Shih. Rapid prototyping of 3D DNAorigami shapes with caDNAno. Nucleic Acids Research, 37:5001-5006, 2009.
36. Carlos Ernesto Castro, Fabian Kilchherr, Do-Nyun Kim, Enrique Lin Shiao, Tobias Wauer, Philipp Wortmann, Mark Bathe, and Hendrik Dietz. A primer to scaffolded DNA origami. Nature methods, 8(3):221-229, 2011.
37. P. W Rothemund, A. Ekani-Nkodo, N. Papadakis, A. Kumar, D. K. Fygenson, and Winfree E. Design and characterization of programmable DNA nanotubes. JACS, 126:16344-163452, 2005.
38. P. Yin, R. Hariadi, S. Sahu, H. M. T. Choi, S. H. Park, T. H. LaBean, and J. H. Reif. Programming molecular tube circumferences. Science, 321:824-826, 2008.
39. J. P. Zheng, J. Birktoft, Y. Chen, T. Wang, R. J. Sha, P. Constantinou, S. Ginell, C. D. Mao, and N. Seeman. From molecular to macroscopic via the rational design of a self-assembled 3d dna crystal. Nature, 461:74-77, 2009.
40. P. W. K. Rothemund, N. Papadakis, and E. Winfree. Algorithmic self-assembly of DNA Sierpinski triangles. PLoS Biology, 2:2041-2053, 2004.
41. A. Chworos, I Severcan, A. Y. A. Y. Koyfman, P. Weinkam, E. Emin Oroudjev, H. G. Hansma, and L Jaeger. Building programmable jigsaw puzzles with RNA. Science, 306:2068-2072, 2004.
42. I. Severcan, Geary C., Chworos A., Voss N., Jacovetty E., and Jaeger L. A polyhedron made of trunas. Nature Chemistry, 2:772-779, 2010.
43. D. Soloveichik, G. Seelig. and E. Winf'ee. Dna as a universal substrate for chemical kinetics. Proceedings of the National Academy of Sciences of the United States of America, 107:5393-5398, 2010.
44. David Yu Zhang, Sherry Xi Chen, and Peng Yin. Optimizing the specificity of nucleic acid hybridization. Nature chemistry, 4(3):208-214, 2012.
45. Sherry Xi Chen, David Yu Zhang, and Georg Seelig. Conditionally fluorescent molecular probes for detecting single base changes in double-stranded DNA. Nature chemistry, 5(9):782-789, 2013.
46. J. Kim, J. J. Hopfield, and E. Winfree. Neural network computation by in vitro transcriptional circuits. In 18th Neural Information Processing Systems (NIPS), 2004.
47. Lulu Qian. Erik Winfree, and Jehoshua Bruck. Neural network computation with DNA strand displacement cascades. Nature, 475(7356):368-372, 2011.
48. Jongmin Kim and Erik Winfree. Synthetic in vitro transcriptional oscillators. Molecular systems biology, 7(1):465, 2011.
49. Joshua I Glaser, Bradley M Zamft, Adam H Marblestone, Jeffrey R Moffitt, Keith Tyo, Edward S Boyden, George Church, and Konrad P Kording. Statistical analysis of molecular signal recording. PLoS Comput. Biol, 9:e1003145, 2013.
50. Chris Thachuk, Erik Winfree, and David Soloveichik. Leakless dna strand displacement systems. In DNA Computing and Molecular Programming, pages 133-153. Springer, 2015.
51. Ryosuke Iinuma, Yonggang Ke, Ralf Jungmann, Thomas Schlichthaerle, Johannes B Woehrstein, and Peng Yin. Polyhedra self-assembled from DNA tripods and characterized with 3d dna-paint. Science, 344(6179):65-69, 2014.
52. D. Wei, M. Dai, and P. Yin. Complex shapes self-assembled from modular molecular components. Nature, 485:623-626, 2012.
53. Y. Ke, L. L. Ong, W. M. Shih, and P. Yin. Three-dimensional structures self-assembled from DNA bricks. Science, 2012.
54. D. Han and P. Yin. Replicable single-stranded DNA origami. in preparation, 2015.

55. John P Sadowski, Colby R Calvert. David Yu Zhang, Niles A Pierce, and Peng Yin. Developmental self-assembly of a DNA tetrahedron. ACS nano, 8(4):3251-3259, 2014.
56. Simon Fredriksson, Mats Gullberg. Jonas Jarvius, Charlotta Olsson, Kristian Pietras, Signin Margrét Gústafsdóttir, Arne Östman, and Ulf Landegren. Protein detection using proximity-dependent dna ligation assays. Nature biotechnology, 20(5):473-477, 2002.
57. Yoshinaga Yoshimura and Kenzo Fujimoto. Ultrafast reversible photo-cross-linking reaction: Toward in situ DNA manipulation. Organic letters, 10(15):3227-3230, 2008.
58. Alexander A Green, Pamela A Silver, James J Collins, and Peng Yin. Toehold switches: de-novo-designed regulators of gene expression. Cell, 159(4):925-939, 2014.
58. David Yu Zhang and Erik Winfree. Control of DNA strand displacement kinetics using toehold exchange. J Am Chem Soc, 131(47):17303-14, 2009.
59. International Publication No. WO 2012/058488 A1 (International Application No. PCT/US2011/058178, filed 27 Oct. 2011).
60. Rothemund, Paul W. K. Folding DNA to create nanoscale shapes and patterns. Nature 440, 297-302, 2006.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of producing a single-stranded nucleic acid, comprising: combining in reaction buffer
   (a) a first catalytic molecule comprising (i) an unpaired 3' toehold domain, (ii) a paired domain comprising a stopper, and (iii) a linkage domain,
   (b) a second catalytic molecule comprising (i) an unpaired 3' toehold domain, (ii) a paired domain comprising a stopper, and (iii) a linkage domain, wherein the unpaired 3' toehold domain of the second catalytic molecule binds to a sequence in the paired domain of the first catalytic molecule;
   (c) a primer that binds to the unpaired 3' toehold domain of the first catalytic molecule,
   (d) a polymerase having strand displacement activity, and
   (e) deoxyribonucleotide triphosphates (dNTPs),
   thereby forming a reaction mixture; and
   incubating the reaction mixture under conditions that result in nucleic acid polymerization, strand displacement and annealing, for a time sufficient to produce a single-stranded nucleic acid record that is longer than the primer.

2. The method of claim 1, wherein the linkage domain of (a) is a loop domain and/or the linkage domain of (b) is a loop domain.

3. The method of claim 1, wherein the step of combining in reaction buffer further comprises
   (f) a third catalytic molecule comprising (i) an unpaired 3' toehold domain, (ii) a paired domain comprising a stopper, and (iii) a linkage domain, wherein the unpaired 3' toehold domain of the third catalytic molecule binds to a sequence in the paired domain of the second catalytic molecule.

4. The method of claim 1, wherein the primer is linked to a detectable molecule.

5. The method of claim 1, wherein the linkage domain of (a) and/or the linkage domain of (b) comprise covalently crosslinked nucleotides.

6. The method of claim 1, wherein the linkage domain of (a) is a stable paired domain and/or the linkage domain of (b) is a stable paired domain.

7. The method of claim 1, wherein the stopper of the first catalytic molecule and/or the stopper of the second catalytic molecule is a synthetic non-DNA linker, a three-carbon linkage, adenylation, an azine, a digoxigenin, a cholesteryl-TEG, I-LINKER, 3-cyanovinylcarbazole, or a non-natural nucleotide sequence.

8. The method of claim 1, wherein the domains of (a) (i) and/or (a) (ii) comprise tandem repeat sequences.

9. The method of claim 1, wherein the unpaired 3' toehold domain of the first catalytic molecule and/or the unpaired 3' toehold domain of the second catalytic molecule is 5-40 nucleotides in length.

10. The method of claim 1, wherein the primer is 10-50 nucleotides in length.

11. The method of claim 1, wherein the unpaired 3' toehold domain of the first catalytic molecule is 5-40 nucleotides in length, the unpaired 3' toehold domain of the second catalytic molecule is 5-40 nucleotides in length, and the primer is 10-50 nucleotides in length.

12. The method of claim 1, wherein the first catalytic molecule is a catalytic hairpin molecule and/or the second catalytic molecule is a catalytic hairpin molecule.

13. The method of claim 1, wherein at least one of the catalytic molecules is attached to a target biomolecule.

14. The method of claim 13, wherein the first catalytic molecule is attached to a first target biomolecule and the second catalytic molecule is attached to a second target biomolecule, wherein the first and second target biomolecule are different biomolecules.

15. The method of claim 3, wherein the step of combining in reaction buffer further comprises
   (g) a plurality of catalytic molecules, each of the catalytic molecules of the plurality comprising (i) an unpaired 3' toehold domain, (ii) a paired domain comprising a stopper, and (iii) a linkage domain, wherein the unpaired 3' toehold domain of each of the catalytic molecules of the plurality binds to a sequence in the paired domain of another catalytic molecule.

16. The method of claim 1, wherein the polymerase is phi29 DNA polymerase, Bst DNA polymerase, or Bsu DNA polymerase.

\* \* \* \* \*

SEQUENCE LISTING

```
<160> NUMBER OF SEQ ID NOS: 7

<210> SEQ ID NO 1
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 1
atctcttatt                                                          10

<210> SEQ ID NO 2
<211> LENGTH: 69
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: G is iisodG
<220> FEATURE:
<221> NAME/KEY: misc_feature
<222> LOCATION: (24)..(24)
<223> OTHER INFORMATION: T is iBiodT
<220> FEATURE:
<221> NAME/KEY: misc_feature
<222> LOCATION: (32)..(32)
<223> OTHER INFORMATION: Modified by a methyl group
<220> FEATURE:
<221> NAME/KEY: misc_feature
<222> LOCATION: (33)..(33)
<223> OTHER INFORMATION: C is iMe-isodC
<220> FEATURE:
<221> NAME/KEY: misc_feature
<222> LOCATION: (60)..(60)
<223> OTHER INFORMATION: C is iMe-isodC
<220> FEATURE:
<221> NAME/KEY: misc_feature
<222> LOCATION: (69)..(69)
<223> OTHER INFORMATION: T is 3InvdT

<400> SEQUENCE: 2
```

```
acatactcat ctcggcgctg gtttttccag cgccgagatg agtatgtagt tagagatgtc    60
acgagatgt                                                            69
```

<210> SEQ ID NO 3
<211> LENGTH: 69
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: G is iisodG
<220> FEATURE:
<221> NAME/KEY: misc_feature
<222> LOCATION: (24)..(24)
<223> OTHER INFORMATION: T is iBiodT
<220> FEATURE:
<221> NAME/KEY: misc_feature
<222> LOCATION: (32)..(32)
<223> OTHER INFORMATION: Modified by a methyl group
<220> FEATURE:
<221> NAME/KEY: misc_feature
<222> LOCATION: (33)..(33)
<223> OTHER INFORMATION: C is iMe-isodC
<220> FEATURE:
<221> NAME/KEY: misc_feature
<222> LOCATION: (69)..(69)
<223> OTHER INFORMATION: T is 3InvdT

<400> SEQUENCE: 3

```
acatactcat ctccgcgctg gtttttccag cgcggagatg agtatgtagt tagagatgtg    60
acgagatgt                                                            69
```

<210> SEQ ID NO 4
<211> LENGTH: 69
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: G is iisodG
<220> FEATURE:
<221> NAME/KEY: misc_feature
<222> LOCATION: (24)..(24)
<223> OTHER INFORMATION: T is iBiodT
<220> FEATURE:
<221> NAME/KEY: misc_feature
<222> LOCATION: (32)..(32)
<223> OTHER INFORMATION: Modified by a methyl group
<220> FEATURE:
<221> NAME/KEY: misc_feature
<222> LOCATION: (33)..(33)
<223> OTHER INFORMATION: C is iMe-isodC
<220> FEATURE:
<221> NAME/KEY: misc_feature
<222> LOCATION: (59)..(59)
<223> OTHER INFORMATION: Modified by a methyl group
<220> FEATURE:
<221> NAME/KEY: misc_feature
<222> LOCATION: (60)..(60)
<223> OTHER INFORMATION: Modified by a methyl group
<220> FEATURE:
<221> NAME/KEY: misc_feature
<222> LOCATION: (61)..(61)
<223> OTHER INFORMATION: Modified by a methyl group
<220> FEATURE:
<221> NAME/KEY: misc_feature
<222> LOCATION: (69)..(69)
<223> OTHER INFORMATION: T is 3InvdT

<400> SEQUENCE: 4

```
acatactcat ctcggcgctg gtttttccag cgccgagatg agtatgtagt tagagatgtg    60
acgagatgt                                                             69
```

<210> SEQ ID NO 5
<211> LENGTH: 10
<212> TYPE: DNA
<213> ORGANISM: Artificial Sequence
<220> FEATURE:
<223> OTHER INFORMATION: Synthetic polynucleotide
<400> SEQUENCE: 5

```
ttctcttatt                                                            10
```

<210> SEQ ID NO 6
<211> LENGTH: 43
<212> TYPE: DNA
<213> ORGANISM: Artificial Sequence
<220> FEATURE:
<223> OTHER INFORMATION: Synthetic polynucleotide
<400> SEQUENCE: 6

```
actaaattca gggccttttg gccctgaatt tagtaataag aga                       43
```

<210> SEQ ID NO 7
<211> LENGTH: 57
<212> TYPE: DNA
<213> ORGANISM: Artificial Sequence
<220> FEATURE:
<223> OTHER INFORMATION: Synthetic polynucleotide
<400> SEQUENCE: 7

```
ugugcaaauc uaugcaaaac ugaatagtgg gaggctagct acaacgagcg gacattt        57
```